United States Patent [19]

Yabe et al.

[11] Patent Number: 5,562,602

[45] Date of Patent: Oct. 8, 1996

[54] INSERT COVER PORTION OF ENDOSCOPE COVER, INSERT COVER PORTION HAVING CHANNELS OF ENDOSCOPE COVER, ENDOSCOPE-COVER-TYPE ENDOSCOPE, ENDOSCOPE-COVER-SYSTEM ENDOSCOPE AND ENDOSCOPE APPARATUS

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji; Yosuke Yoshimoto, Tama; Yasuyuki Futatsugi, Hachioji, all of Japan

[73] Assignee: Olympus Optical Co., Ltd., Tokyo, Japan

[21] Appl. No.: 53,489

[22] Filed: Apr. 28, 1993

[30] Foreign Application Priority Data

| Mar. 15, 1993 | [JP] | Japan | 5-011197 U |
| Mar. 15, 1993 | [JP] | Japan | 5-054357 |
| Mar. 15, 1993 | [JP] | Japan | 5-054358 |

[51] Int. Cl.$^6$ .................. A61B 1/00; A61B 1/005
[52] U.S. Cl. ................... 600/121; 600/122; 600/124; 600/125
[58] Field of Search ............... 128/4, 6, 844; 604/163, 171, 263; 359/510; 206/303, 305, 306, 363, 368, 316.1; 600/121, 122, 124, 125

[56] References Cited

U.S. PATENT DOCUMENTS

| Re. 33,854 | 3/1992 | Adair | 128/6 |
| Re. 34,110 | 9/1992 | Opie . | |
| 3,162,190 | 12/1964 | Del Gizzo . | |
| 4,241,828 | 12/1980 | Bourdelle et al. | 206/306 |
| 4,408,692 | 10/1993 | Sigel et al. | 206/438 |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,878,485 | 11/1989 | Adair | 128/6 |
| 4,886,049 | 12/1989 | Darras | 128/4 |
| 4,907,395 | 3/1990 | Opie | 53/434 |
| 4,991,564 | 2/1991 | Takahashi | 128/4 |
| 4,991,565 | 2/1991 | Takahashi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |
| 5,237,984 | 8/1993 | Williams, III et al. | 128/4 |
| 5,239,981 | 8/1993 | Anapliotis | 128/4 |
| 5,251,613 | 10/1993 | Adair | 128/6 |
| 5,301,657 | 4/1994 | Lafferty et al. | 128/6 |

FOREIGN PATENT DOCUMENTS

| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-13105 | 2/1991 | Japan . |
| 3-37030 | 2/1991 | Japan . |
| 3-37029 | 2/1991 | Japan . |
| 3-29635 | 2/1991 | Japan . |
| 3-29634 | 2/1991 | Japan . |
| 3-221024 | 9/1991 | Japan . |
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |
| 3-101901 | 10/1991 | Japan . |
| 3-101902 | 10/1991 | Japan . |
| 4-325138 | 11/1992 | Japan . |

*Primary Examiner*—Richard J. Apley
*Assistant Examiner*—Beverly M. Flanagan

*Attorney, Agent, or Firm*—Armstrong, Westerman, Hattori, McLeland & Naughton

[57] ABSTRACT

An insert cover portion having channels including an air-supply tubular passage, a water-supply tubular passage and a suction tubular passage sidewards extending from a joint adjacent to an operator in a direction of the longitudinal axis of the insert cover portion, the insert cover portion having channels further including an external tubular passage extending outwardly. The insert cover portion has the operation facility realized by considering to prevent hindering of the operation by various tubular passages extending from the joint.

5 Claims, 30 Drawing Sheets

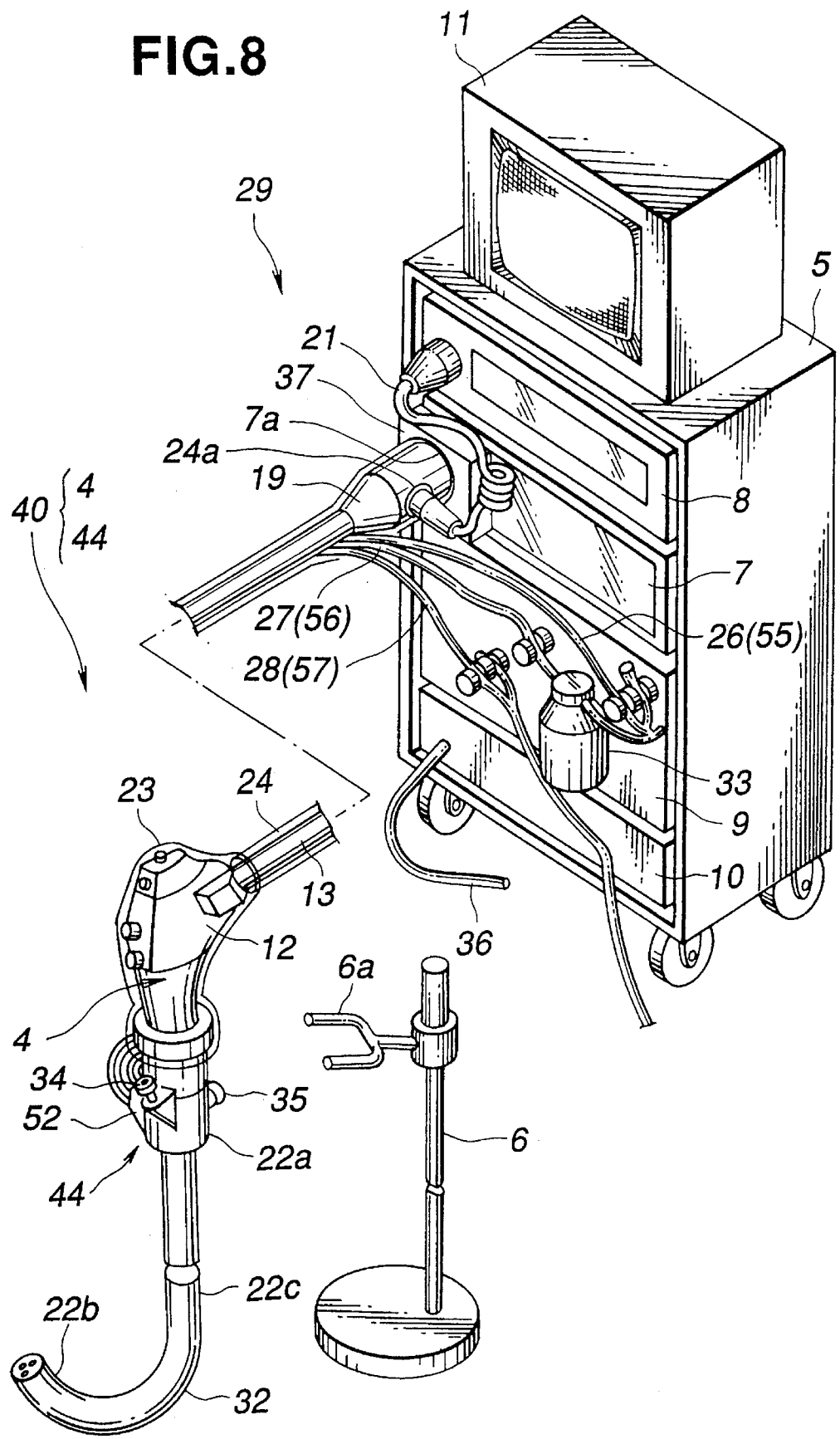

FIG. 9
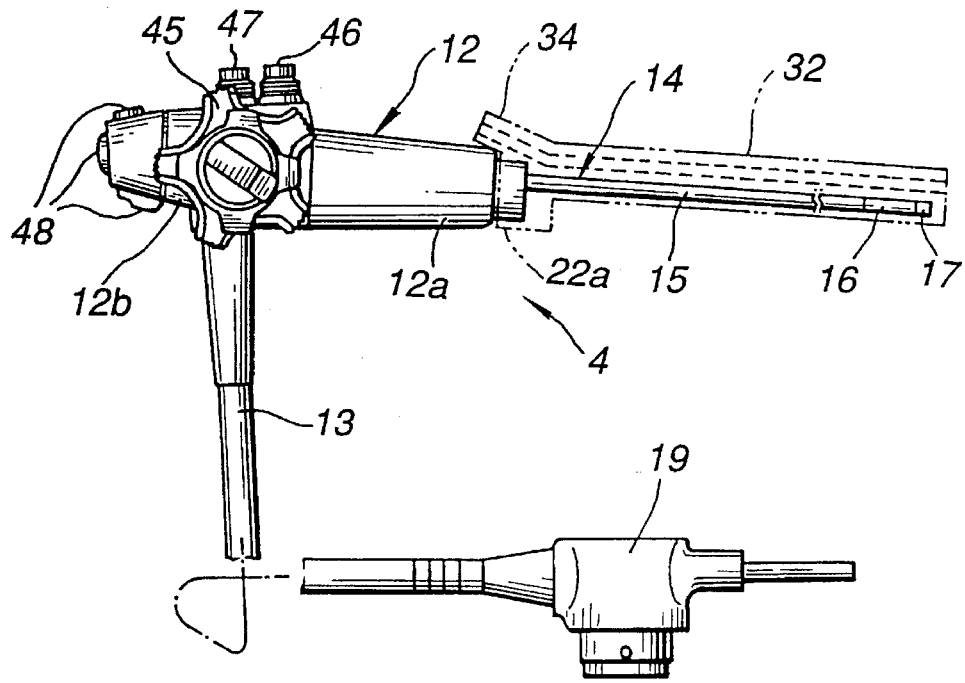
FIG.10(a)
FIG.10(b)
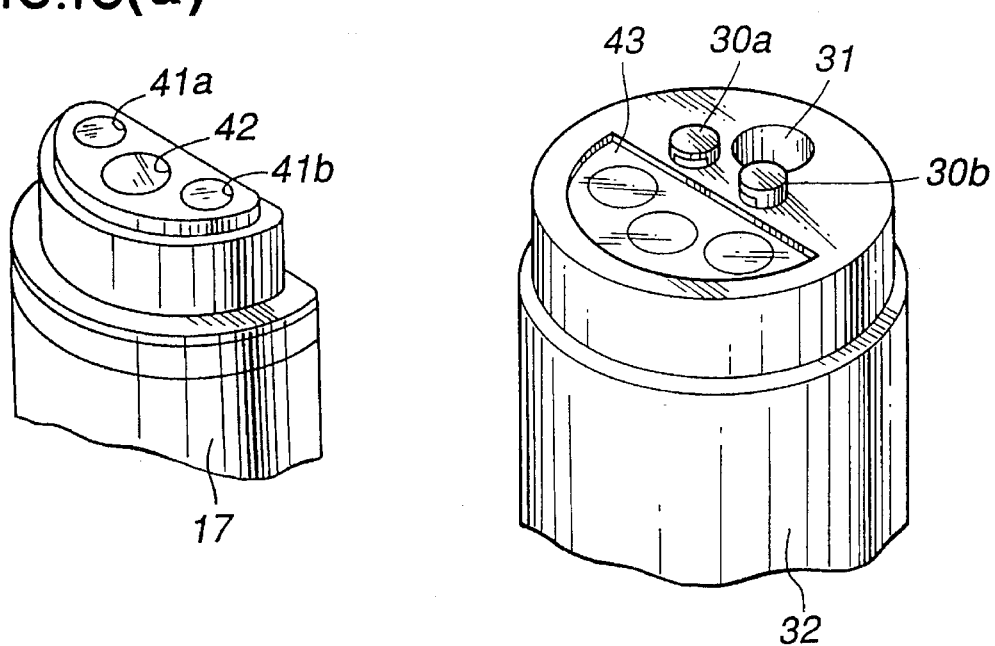

(a)

INSERT COVER PORTION OF ENDOSCOPE COVER, INSERT COVER PORTION HAVING CHANNELS OF ENDOSCOPE COVER, ENDOSCOPE-COVER-TYPE ENDOSCOPE, ENDOSCOPE-COVER-SYSTEM ENDOSCOPE AND ENDOSCOPE APPARATUS

BACKGROUND OF THE INVENTION

1. Field of the Invention

The present invention relates to improvements in an insert cover portion of an endoscope cover, an insert cover portion having channels of an endoscope cover, an endoscope-cover-type endoscope, an endoscope-cover-system endoscope and an endoscope apparatus capable of facilitating the preparation for an inspection to be performed prior to the next inspection of a medical case.

2. Description of the Related Art

The inspection using an endoscope must use a clean endoscope that has been sufficiently cleaned and disinfected prior to performing the inspection.

The endoscope is cleaned and disinfected after it has been used in the body cavity of a patient, resulting in taking an excessively long time. Accordingly, a disposable-type endoscope-cover-system endoscope for performing the inspection has been suggested in place of the conventional repeated-use-type endoscope.

The endoscope-cover-system endoscope is composed of an endoscope cover for covering an insertion portion of the endoscope and a cover-type endoscope to be inserted into the endoscope cover. Examples of the endoscope-cover-system endoscope have been disclosed in, for example, Japanese Patent Publication No. 2-54734 and U.S. Pat. No. 3,162,190.

As a general rule, the cover-type endoscope having the endoscope cover fastened thereto comprises an insertion portion that includes an imaging system or an observation optical system and a light guide fiber.

Although channels for a curing tool and an air-supply/water-supply tube can be contaminated with body fluid, they cannot easily be cleaned and disinfected because of their thin and elongated shapes. Accordingly, some endoscope covers have a tube including a channel for a curing tool and an air-supply/water-supply tube, the two end portions of which are opened.

The insert of the endoscope-cover-type endoscope must be cleaned and disinfected prior to performing an operation. The endoscope is inserted into the body cavity of a patient in a manner that the insert of the endoscope is covered with the endoscope cover. After the endoscope has been used, the endoscope cover is removed and disposed of. By disposing of the endoscope for each patient as described above, the necessity of cleaning and disinfecting the endoscope can be eliminated. The endoscope can therefore be successively used while eliminating the necessity of repeatedly cleaning and disinfecting the endoscope.

The endoscope cover is generally composed of a plurality of cover members. The endoscope cover is, for example, composed of an insert cover portion for covering the insert of the endoscope, a control-unit cover for covering a control unit, and a cord-cover for covering a universal cord.

The insert cover portion of the endoscope cover has a portion for covering a leading unit and a portion for covering a unit adjacent to an operator, the two portions of the insert cover portion being hermetically connected to each other by a soft cover outer coat. Furthermore, the insert cover portion includes a lumen into which the endoscope-cover-type endoscope (hereinafter called a cover-type endoscope) is inserted. Furthermore, the insert cover portion has channels connected to an opening portion of the leading unit, the channels acting to supply air and water and to insert the forceps or the like.

The trailing portions of the channels are connected to an external fluid control apparatus so that operations required to perform the operations with the endoscope, such as the air supply, the water supply and suction operations, are performed through each of the foregoing channels.

Each of the channels is connected to the portion of the insert cover portion for covering the unit adjacent to the operator, followed by again extending substantially in parallel to a direction of the longitudinal axis of the insert cover portion. Then, each of the channels is arranged along the universal cord, followed by connecting it to the external fluid control apparatus.

However, the portion for covering the unit adjacent to the operator, from which each of the foregoing channels extends as described above, has a forceps insertion port of the forceps channel. The foregoing channels extending toward the control unit excessively hinder the operation by using the forceps at the time of inserting/drawing the forceps.

What is worse in addition to the operation by using the forceps, the presence of a plurality of the channels adjacent to the hand of the operator holding the control unit deteriorates the handling facility at the time of rotating and twisting the control unit.

Although it is ideal to insert the forceps while minimizing bends of the passage, through which the forceps is inserted, for the purpose of making the forceps to straightly approach the insertion portion, the foregoing structure cannot allow the foregoing object to be realized in terms of the impossibility present in the layout.

The insert cover portion has a length, that is substantially the same as the length of the insert, in order to cover the insert of the endoscope. Although the length of the insert of the endoscope varies depending upon the way of usage, a soft insert is formed into a relatively long shape. Also the outer diameter of the insert cover varies, for example, a small diameter or a large diameter to be adaptable to the outer diameter of the insert of the endoscope.

Also a cover-type endoscope fastened to the foregoing insert cover portion must exhibit excellent insertion facility in order to relieve the pain of the patient and to shorten the time required to complete the inspection. In particular, there is a tendency that the deeper the insert is inserted, the more the insertion becomes difficult.

While making a consideration about this fact occurring with the foregoing conventional insert cover, the attained insertion facility has been unsatisfactory when it is used in a tract organ having many bends because it can easily be kinked at an intermediate position.

In addition to the handling and insertion facilities to be satisfied, the cover-type endoscope must satisfy the following requirements in terms of maintaining cleanness that is the first object of fastening of the endoscope cover.

Similarly to the conventional cover-less endoscope, the cover-type endoscope has a warping mechanism for warping a warp-enabled portion provided for the insert. The warping mechanism has an arrangement that its warp-enabled portion is warped in accordance with the amount of the operation of an angle knob disposed in the control unit of the cover-type endoscope.

Hitherto, the control unit of an endoscope has been made to be a contamination area (contamination is allowed) and has been used as a recourse (repeatedly used) portion, while the insertion cover portion of the endoscope cover has been made to be a clean area (no contamination is allowed) and has been used as a disposable (disposed after the use) portion.

The angle knob provided in the control unit is always operated by the hand (usually the left hand) that holds the control unit. On the other hand, the hand (usually the right hand), that holds the insert, operates the angle knob, resulting in a necessity of performing the inspection in such a manner that the hand, that holds the insert, cannot be contaminated via the angle knob.

In order to keep clean the hand that holds the insert, the angle knob provided for the control unit of the endoscope must be operated by the hand that holds the control unit.

However, great skill is required to operate the angle knob by only the hand that holds the control unit, resulting in complications to occur.

When the inspection using the endoscope is performed, a curing tool, such as a forceps, is sometimes used in addition to the foregoing warping operation. Therefore, the operation must be performed carefully in such a manner that the hand, that holds the insert, does not touch the outer wall of the control unit, which is the contamination area.

Even if the angle knob can be operated by the hand that holds the insert, the operation must be performed carefully to prevent an undesirably touch with the outer wall of the control unit at the time of operating the angle knob.

However, it is a complicated work to pay attention not to touch the outer wall of the control unit in the vicinity of the angle knob when the angle knob is operated by the hand holding the insert cover portion, into which the insert of the endoscope has been inserted, or when the curing tool, such as a forceps, is inserted/drawn by the hand holding the insert cover portion.

When the angle knob is operated, great skill is required and it is a complicated work to operate the angle knob by only the hand that holds the control unit.

A variety of endoscope-cover-type endoscopes are available to be adaptable to the subjects of use and the purposes. Hence, many kinds of corresponding endoscope covers are available, resulting in a possibility that an insert cover portion, that is not the corresponding type, might be erroneously attached.

Some cover-type endoscopes are arranged to have an ocular portion which enables an observation with the naked eyes to be performed. However, the mechanism for adjusting the diopter is covered with the endoscope cover in a state where the cover-type endoscope is covered with the endoscope cover, resulting in a difficulty to occur when the diopter is adjusted from the outer portion of the cover. Hence, even if the difference in the diopter is present among a plurality of observers, the observation is limited by the diopters in a predetermined range.

Since the cord cover portion is scarcely contaminated, it is wasteful to exchange the used cord cover portion for a new one at each operation.

OBJECTS AND SUMMARY OF THE INVENTION

An object of the present invention is to provide an insert cover portion having channels exhibiting excellent operation facility to prevent hindering of the operation by various channels extending from the unit adjacent to an operator.

Another object of the present invention is to provide an insert cover portion having channels of an endoscope cover which is capable of easily removing a substance clogged in the channel and which can be cleaned.

Another object of the present invention is to provide an endoscope apparatus exhibiting excellent facility of exchanging a cord cover portion for covering a universal cord of an endoscope.

Another object of the present invention is to provide an endoscope apparatus exhibiting economy because a cord cover portion, that does not need to be exchanged, cannot be damaged, and therefore, it can be repeatedly used.

Another object of the present invention is to provide an endoscope-cover-system endoscope capable of improving the performance of causing the curing tool to target a subject without using a curing-tool raising frame.

Another object of the present invention is to provide an insert cover portion of an endoscope cover which cannot be easily kinked at the time of insertion, and therefore, the insertion facility of which can be improved.

Another object of the present invention is to provide an insert cover portion of an endoscope cover which is capable of preventing the irregular running and twisting of the tubular passage occurring at the time of the warping operation or insertion.

Another object of the present invention is to provide an endoscope-cover-system endoscope capable of adapting to difference in the diopter among observers even if the observes have different diopters, and therefore, capable of performing an observation at a proper diopter.

Another object of the present invention is to provide an endoscope-cover-system endoscope capable of preventing erroneous fastening of an insert cover portion that is not adaptable to an employed endoscope-cover-type endoscope.

Another object of the present invention is to provide an endoscope-cover-system endoscope with which the hand holding the insert does not touch a control unit, which is an unclean area, without paying any special attention at the time of operating the angle knob or inserting/removing a curing tool with the foregoing hand.

Another object of the present invention is to provide an endoscope-cover-type endoscope with which the hand holding the insert covered with a cover does not touch the portions which are touched by the other hand that charges in unclean areas to perform a warping operation while exhibiting excellent warping operation facility.

According to a preferred aspect of the present invention, there is provided an insert cover portion having channels of an endoscope cover for covering at least an insert of an endoscope-cover-type endoscope, the insert cover portion having channels of an endoscope cover comprising: a leading unit member; a unit member adjacent to an operator; a soft tubular member for establishing a hermetical connection between the leading unit member and the unit member adjacent to the operator; and channels passing through a portion from the leading unit member to an intermediate position of the unit member adjacent to the operator which are connected by the tubular member, the channels passing sidewards with respect to a direction of the longitudinal axis of the insert cover portion at the intermediate position of the unit member adjacent to the operator to project outwardly.

The other features and advantages of the present invention will be apparent from the detailed description below.

BRIEF DESCRIPTION OF THE DRAWINGS

FIGS. 1 to 5(a)–(b) relate to a first embodiment of the present invention;

FIG. 1 is an overall schematic view which illustrates an endoscope apparatus to which a cover-type endoscope is connected;

FIG. 2 is a schematic view which illustrates the cover-type endoscope;

FIG. 4 is a side-elevational cross sectional view which illustrates the leading portion of the cover-system endoscope;

FIG. 5(a) is an enlarged view and FIG. 5(b) is a cross sectional view which illustrates the cover-system endoscope;

FIGS. 6(a)–(b) and 7 relate to a second embodiment of the present invention;

FIG. 6(a)–(b) is a perspective view which illustrates a leading portion of a cover;

FIG. 6(b) is a cross sectional view taken along line b—b of FIG. 6(a);

FIGS. 8 to 12 relate to a third embodiment of the present invention;

FIG. 8 is an overall schematic view which illustrates an endoscope apparatus to which a cover-type endoscope is connected;

FIG. 9 is a schematic view which illustrates the cover-type endoscope;

FIGS. 10(a) and 10(b) are perspective views of the leading portions of the cover-type endoscope and an insert cover portion;

FIG. 11 is a side elevational cross sectional view which illustrates the leading portion of the cover-system endoscope;

FIG. 13 is a side elevational view which illustrates a cover-system endoscope;

FIG. 14 is a cross sectional view taken along line 14—14 of FIG. 13;

FIG. 15 is a side elevational cross sectional view which illustrates a cover-system endoscope;

FIG. 16 is an assembly drawing which illustrates the endoscope, a control unit cover and an angle knob;

FIG. 17 is a perspective view which illustrates the control-unit cover portion;

FIG. 18 is a cross sectional view which illustrates an ocular portion cover;

FIG. 19 is a cross sectional view which illustrates a channel according to a modification;

FIG. 20 is a cross sectional view which illustrates the channel according to the modification;

FIG. 21 is a cross sectional view which illustrates the channel according to the modification;

FIG. 22 is an overall schematic view which illustrates an endoscope apparatus to which a cover-type endoscope is connected;

FIGS. 23(a) and 23(b) are schematic views which illustrate the cover-type endoscope, and the installation of an angle knob;

FIG. 24 is a side elevational cross sectional view which illustrates the leading portion of the cover-system endoscope;

FIG. 25 is a structural view which illustrates the cover-type endoscope to which a control-unit cover is fastened;

FIG. 26 illustrates installation of the control-unit cover portion and the angle knob;

FIG. 27 is a cross sectional view which illustrates the structure of a warp-control mechanism;

FIG. 28 is a structural view which illustrates a modification of the endoscope control unit and the insert cover portion;

FIG. 29 illustrates installation of the universal cord cover portion;

FIG. 30 is a side elevational view which illustrates a state where the universal cord cover portion is contracted;

FIG. 31 is a schematic view which illustrates an insert cover portion;

FIG. 32 is a schematic view which illustrates a cover-system endoscope;

FIG. 33 is a cross sectional view which illustrates the structure of a warp control mechanism;

FIG. 34 illustrates the operation of the angle knob;

FIG. 35 illustrates the action of the guard portion at the time of inserting/drawing a curing tool;

FIG. 37 is an overall schematic view which illustrates an endoscope apparatus to which a cover-type endoscope is connected;

FIG. 38 is a schematic view which illustrates the cover-type endoscope;

FIG. 39 illustrates installation of an angle knob;

FIG. 40 is a side elevational cross sectional view which illustrates the leading portion of the cover-system endoscope;

FIG. 41 is a cross sectional view which illustrates the structure of a warp control mechanism.

DETAILED DESCRIPTION OF THE PREFERRED EMBODIMENTS

Figure 1:
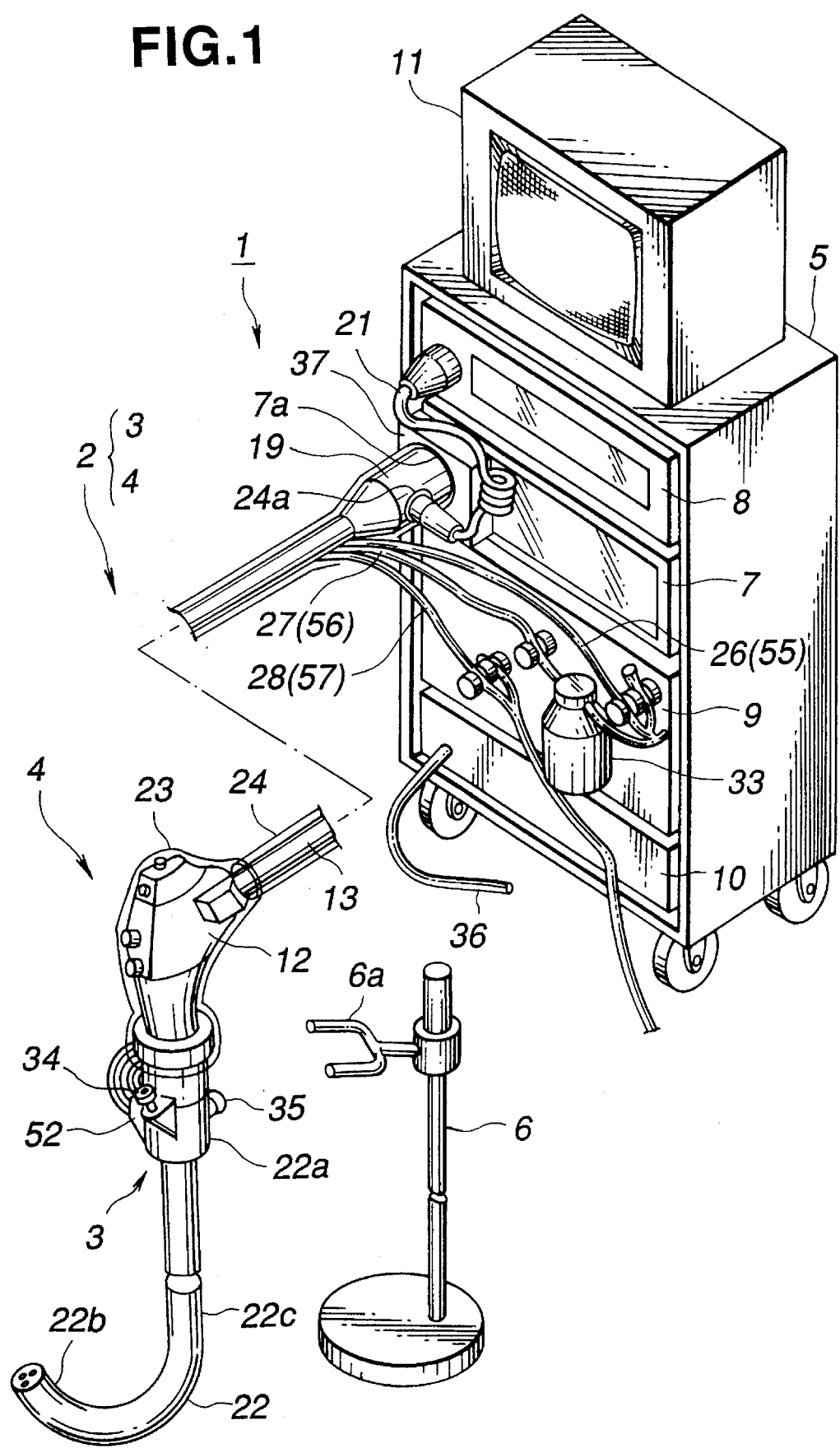
Figure 2:
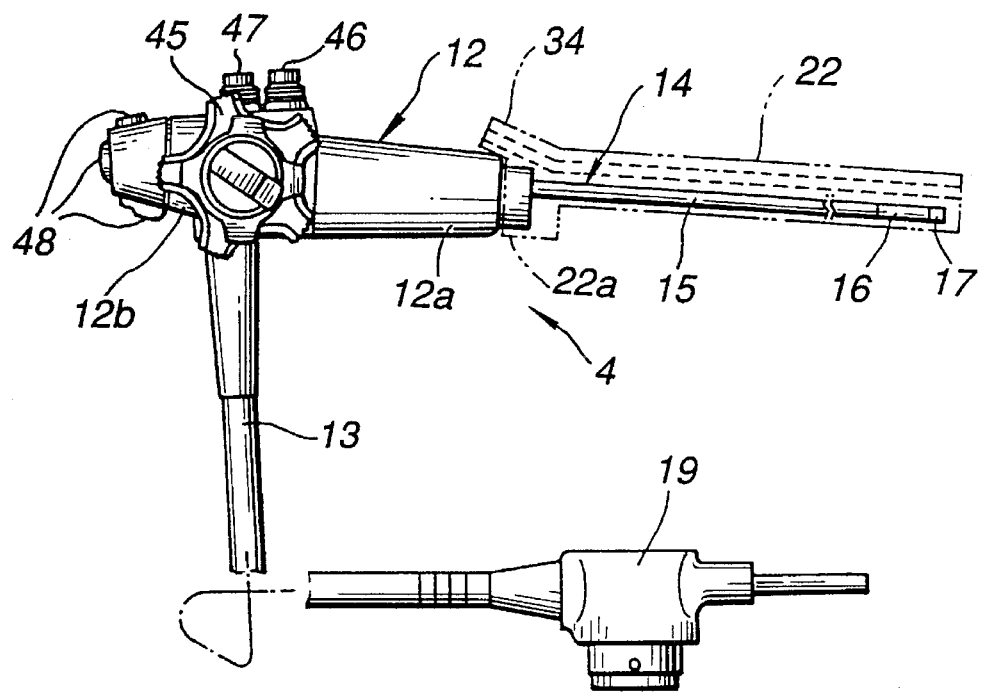
Figure 3A:
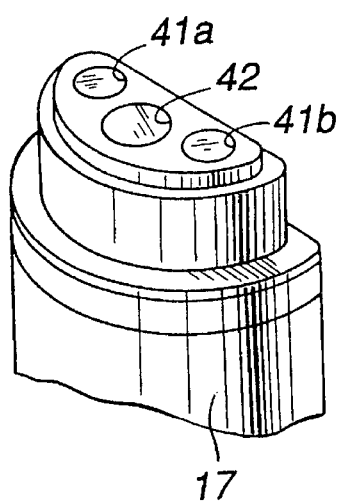
FIGS. 3(a) and 3(b) are perspective view which illustrates leading portions of the cover-type endoscope and an insert cover portion.
Figure 3B:
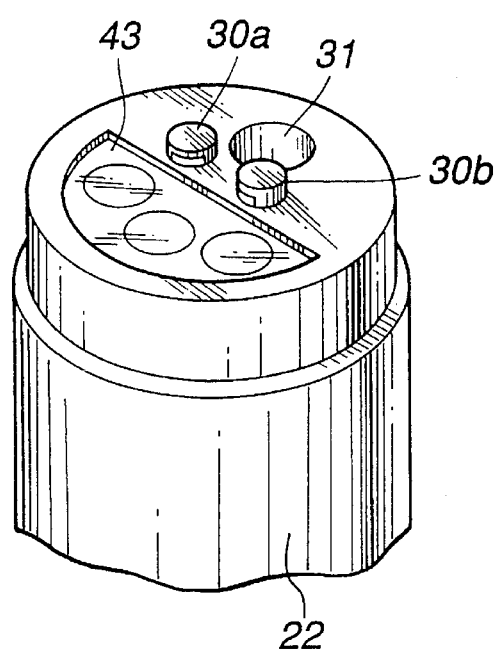
Figure 4:
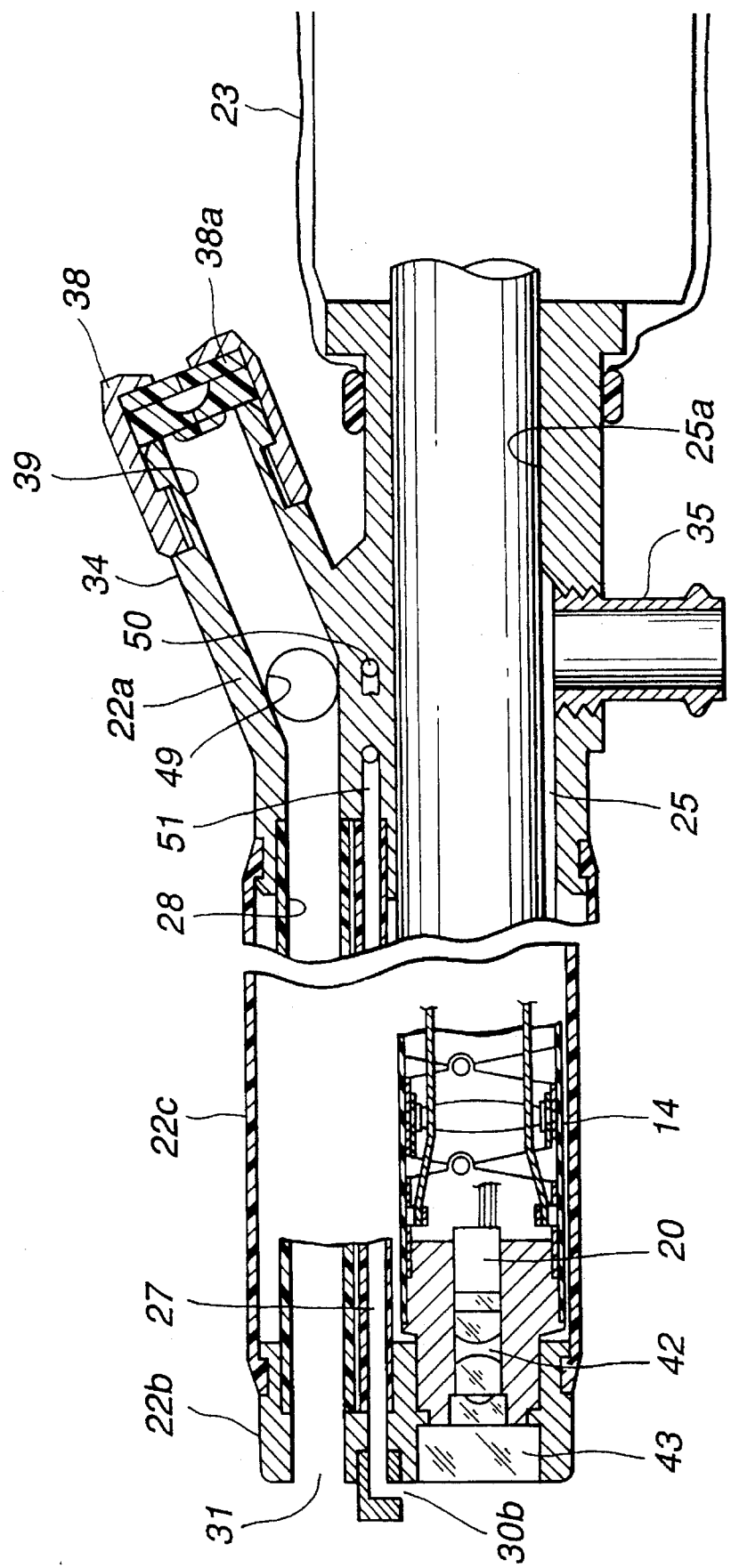
Figure 5A:
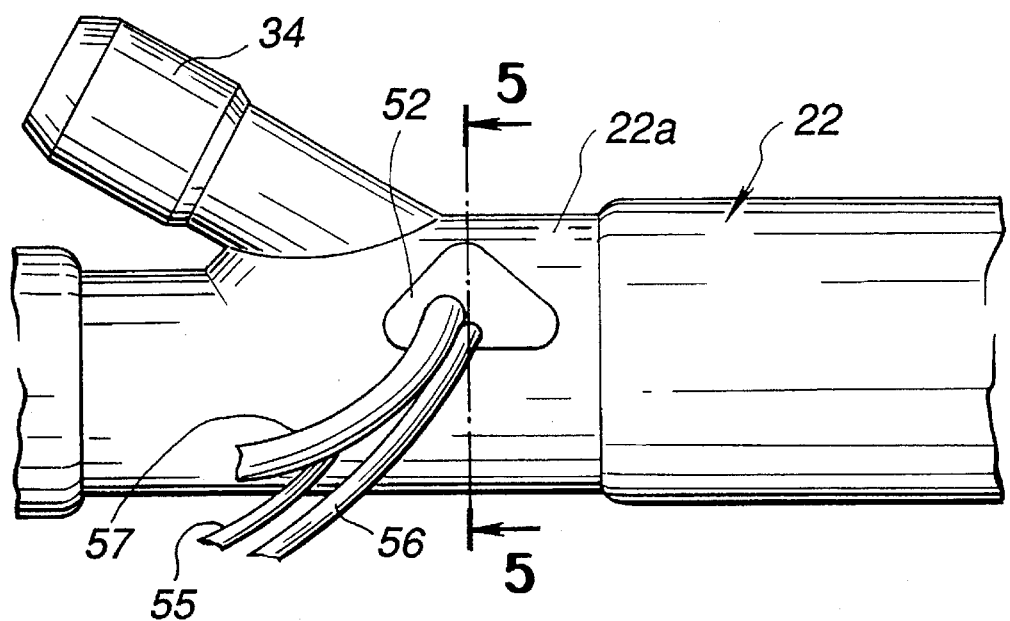

FIGS. 1 to 5(a)–(b) relate to a first embodiment of the present invention. FIG. 1 is an overall schematic view which illustrates an endoscope apparatus to which a cover-type endoscope is connected. FIG. 2 is a schematic view which illustrates the cover-type endoscope. FIG. 3 is a perspective view which illustrates leading portions of the cover-type endoscope and an insert cover portion. FIG. 4 is a side-elevational cross sectional view which illustrates the leading portion of the cover-system endoscope. FIG. 5(a) is an enlarged view and FIG. 5(b) is a cross sectional view which illustrate the cover-system endoscope.

An endoscope apparatus 1 shown in FIG. 1 is an apparatus to which an endoscope-cover-system endoscope (hereinafter abbreviated a "cover-type endoscope") 2 having channels can be attachably/detachably connected.

The cover-system endoscope 2 is constituted by combining an endoscope cover (hereinafter abbreviate to a "cover") 3 having channels and an endoscope-cover-type endoscope (hereinafter abbreviated to a "cover-type endoscope") 4 having channels. The cover-type endoscope 4 is an electronic-type endoscope.

The cover 3 covers an insert and the like of the cover-type endoscope 4 to eliminate the necessity of cleaning and disinfecting the endoscope to be performed after an inspection has been completed.

The endoscope apparatus 1 comprises the cover-system endoscope 2, a cart 5 accommodating various peripheral devices to which the cover-system endoscope 2 is connected, and a cover holder 6 for holding the cover-system endoscope 2.

The cart 5 shown in FIG. 1 and accommodating the peripheral devices accommodates, for example, a light source apparatus 7, a video processor 8, a fluid control apparatus 9, and an expander (hereinafter abbreviated to an "expander") 10 for an endoscope-cover having channels. The cart 5 holds a monitor 11 placed on the ceiling plate thereof.

The light source apparatus 7 supplies irradiation light to the cover-type endoscope 4 of the cover-system endoscope 2. The video processor 8 is connected to the electronic-type cover-type endoscope 4 to convert an electric signal supplied from the endoscope 4 into a standard video signal, followed by outputting the video signal to the monitor 11. The monitor 11 receives the video signal to display an image of the endoscope 4.

The fluid control apparatus 9 supplies air/water through tubular passages formed in the cover 3 and serving as channels to be described later. Therefore, the fluid control apparatus 9 has a water-supply source and an air-supply source (omitted from illustration). The tubular passages connected to the air-supply source and the water-supply source are controlled by electromagnetic valves to be opened/closed as desired.

The expander 10 supplies air into the cover 3 to expand it. As a result of the expansion, the cover-type endoscope 4 can easily be fastened to or removed from the cover 3.

As shown in FIG. 2, the cover-type endoscope 4 comprises a control unit 12, a universal cord 13 extending from the side portion of the control unit 12, and an insert 14 connected to the control unit 12. The insert 14 of the cover-type endoscope 4, as shown in FIG. 2, comprises a flexible tube portion 15, a warp-enabled portion 16 that can be warped, and a hard leading portion 17 when viewed from the base portion of the control unit 12 toward the leading portion.

The insert 14 of the cover-type endoscope 4 has a small diameter and has a D-shape cross sectional shape as shown in FIG. 3A. As shown in FIG. 3A, the leading portion 17 of the cover-type endoscope 4 has irradiation optical systems 41a and 41b and an objective optical system 42 disposed therein. It should be noted that the insert 14 of the endoscope 4 may be formed into a cylindrical shape.

At the rear ends of the irradiation optical systems 41a and 41b, light emission ends of light guide fibers (omitted from illustration) are disposed. The light guide fibers are allowed to pass through the insert 14, the control unit 12 and the universal cord 13.

The universal cord 13 has, at an end portion thereof, a connector 19. The connector 19 is attachably/detachably connected to a connector receptor 7a provided for the light source apparatus 7. As a result, irradiation light can be supplied from the light source apparatus 7 to the incidental ends of the light guide fibers.

The connector receptor 7a of the light source apparatus 7 has a cord-cover accommodating case 37 to surround the connector receptor 7a. The cord-cover accommodating case 37 is formed into a box-like shape to accommodate a disposable-type universal cord cover portion to be described later, the cord-cover accommodating case 37 having, in the front surface thereof, an opening through which the connector 19 is allowed to pass.

As shown in FIG. 4, a solid-state image sensing device 20 for converting an incident optical image into an electric signal is disposed at the rear end of the objective optical system 42. The electric signal transmitted from the solid-state image sensing device 20 is received by the video processor 8 via a signal cord 21 extending from the side portion of the connector 19 shown in FIG. 1 and so forth.

As shown in FIG. 2, the control unit 12 has a holding portion 12a at the base portion thereof. Furthermore, a control unit body 12b is connected to the upper portion of the holding portion 12a. The control unit body 12b of the control unit 12 has an angle knob 45, an air-supply/water-supply control switch 46, a suction control switch 47, and a function switch 48 for taking a photograph each disposed therein.

The angle knob 45 is attachably/detachably provided with respect to the control unit body 12b.

As shown in FIG. 1, the cover 3 for covering the cover-type endoscope 4 is composed of an insert cover portion 22, a control-unit cover portion 23, and a universal-cord cover portion 24. The insert cover portion 22 of the cover 3 covers the insert 14 of the cover-type endoscope 4. The control-unit cover portion 23 of the cover 3 covers the control unit 12 of the cover-type endoscope 4 and three tubular passages to be described later. The universal-cord cover portion 24 of the cover 3 covers the universal cord 13 of the cover-type endoscope 4 and three tubular passages to be described later. All portions of the cover 3 are fastened to the cover-type endoscope 4 so that the endoscope-type endoscope 4 is covered with the cover 3 hermetically with respect to water.

The cover holder 6 shown in FIG. 1 has an arm portion 6a that holds the insert cover portion 22 at the time of fastening the insert cover portion 22 to the cover-type endoscope 4. As a result, the endoscope 4 can sanitarily be held because the hand does not touch the cover 3. Furthermore, the operation can easily be performed.

FIG. 4 is a side elevational cross sectional view which illustrates a state where the cover-type endoscope 4 is inserted into the insert cover portion 22 of the cover 3.

The insert cover portion 22 is used to isolate the insert 14 of the cover-type endoscope 4 from the external environment. The insert cover portion 22 is formed into an elongated shape, the insert cover portion 22 having a joint 22a (hereinafter abbreviated to a "joint") for fixing the control unit 12 of the endoscope 4, that is a unit adjacent to the operator, and a leading unit portion 22b that are made of hard material, for example, metal or resin.

The portion between the joint 22a of the insert cover portion 22 and the leading unit portion 22b is hermetically covered with an insert-cover coat 22c made of flexible material.

The insert-cover coat 22c is made of soft resin, such as polyurethane, that exhibits excellent chemical resistance and that is relatively flexible. The cover coat 22c is connected at its leading portion which is received by an edge portion formed around the rear end portion of the leading unit portion 22b. The cover coat 22c is similarly connected in the vicinity of the joint 22a.

Furthermore, the insertion cover portion 22 includes a endoscope insertion channel 25 through which the insert 14 is able to pass, and an air-supply tubular passage 26, a water-supply tubular passage 27 and a suction tubular passage 28 serving as the channels.

The base portion of the endoscope insertion channel 26 has an opening portion 25a for inserting the insert 14, the opening portion 25a being formed at a position of the joint 22a. The opening portion 25a of the endoscope insertion channel 25 is arranged to be engaged with the end portion of the insertion portion 14 adjacent to the operator. It should be noted that the opening portion 25a may be arranged to be connected to the base portion of the endoscope control unit 12. The endoscope insertion channel 25 is closed in the leading unit portion 22b so that the insert 14 of the cover-type endoscope 4 can be isolated hermetically from the outer environment.

The leading unit portion 22b of the insert cover portion 22 has a transparent window 43 at the leading portion of the endoscope insertion channel 26 as shown in FIG. 3B. The window 43 has a size capable of including the irradiation optical systems 41a and 41b and the objective optical system 42 of the cover-type endoscope 4, the window 43 being formed to face the foregoing optical systems 41a, 41b and 42. The window 43 is formed into a shape to be adaptable to the semicircular shape of the leading portion 17 of the endoscope 4.

The leading unit portion 22b of the insert cover portion 22 has an air-supply nozzle 30a, a water-supply nozzle 30b and an opening 31 each of which is opened toward the window 43. The air-supply and water-supply nozzles 30a and 30b respectively are communicated with and connected to the air-supply tubular passage 26 and the water-supply tubular passage 27. The opening 31 is communicated with and connected to the suction tubular passage 28.

As described later, the air-supply tubular passage 26, the water-supply tubular passage 27 and the suction tubular passage 28 are allowed to extend from the side portion of the joint 22a, and their end portions are respectively opened.

As shown in FIG. 1, the air-supply tubular passage 26 is communicated with and connected to the air-supply source (omitted from illustration) of the fluid control apparatus 9. The water-supply tubular passage 27 is communicated with and connected to the foregoing air-supply source via a water-supply tank 33, which is the water-supply source. Furthermore, the suction tubular passage 28 is communicated with and connected to a suction bin (omitted from illustration) and a suction source (omitted from illustration).

A curing tool insertion port 34 and an expansion tube joint 35 project over the side portion of the joint 22a as shown in FIG. 4. The expansion tube joint 35 includes the internal tubular passage that is connected to the endoscope insertion channel 25. An expansion tube 36 connected to the expander 10 is attachably/detachably connected to the expansion tube joint 35.

The curing tool insertion port 34 projects diagonally rearwards with respect to a direction of the longitudinal axis of the insert cover portion 22. The internal tubular passage of the curing tool insert port 34 is opened at the end portion thereof, while another end portion is connected to the suction tubular passage 28. That is, the suction tubular passage 28 also serves as a tubular passage for the curing tool channel at the leading portion thereof. Therefore, the opening 31 is an outlet port for the curing tool.

The curing tool insertion port 34 receives a forceps cap 38 having a packing 38a made of an elastic material.

As shown in FIG. 4, the air-supply tubular passage 26, the water-supply tubular passage 27 and the suction tubular passage 28 are, at their rear end portions, bent in the joint 22a, and respectively include the following connection tubes.

In the rear of the suction tubular passage 28, a curing tool insertion passage 39 connected to the curing tool insertion port 34 is formed. At the branch point of the tubular passage forming the suction tubular passage 28 from the leading unit portion 22b to an intermediate point of the joint 22a and the foregoing curing tool insertion passage 39, a suction connection tube 49 is branched sidewards with respect to the direction of the longitudinal axis of the insertion cover portion 22. That is, the suction tubular passage 28 bents sidewards to extend with respect to the longitudinal axis of the insertion cover portion 22.

Similarly, the rear portions of the air-supply tubular passage 26 and the water-supply tubular passage 27 respectively formed into an air-supply connection passage 50 and a water-supply connection passage 51 extending sidewards in the joint 22a with respect to the longitudinal axis of the insertion cover portion 22. In order to prevent interfere occurring among the tubular passages, the air-supply connection tube 50 of the air-supply tubular passage 26 is bent at a position more rearwards than the water-supply connection tube 51 of the water-supply tubular passage 27.

Figure 5B:
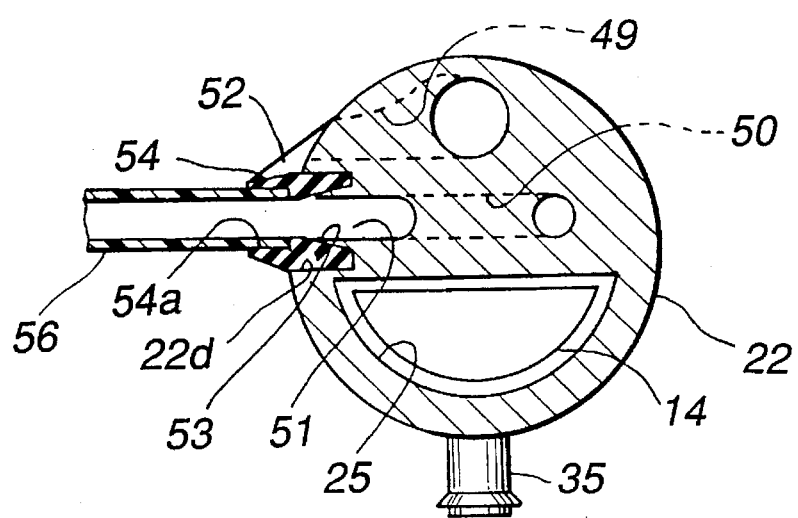

As shown in FIG. 5a which is a side elevational view, the joint 22a of the insert cover portion 22 has a tubular passage integrating connector 52 in the side portion thereof. The tubular passage integrating connector 52 is, in the joint 22a, disposed below the curing tool insertion port 34 at a position different in the circumferential direction. FIG. 5(b) is a cross sectional view taken along line 5—5 of FIG. 5(a).

The tubular passage integrating connector 52 is made of elastic material and is hermetically connected to a joining recess 22d formed in the side portion of the joint 22a as shown in FIG. 5(b). The recess 22d has three connection projections in which the openings of the suction connection tube 49, the air-supply connection tube 50 and the water-supply connection tube 51 are respectively formed. It should be noted that FIG. 5B shows only a connection projection 53 for the water-supply connection tubular passage 51.

The tubular passage integrating connector 52 is hermetically connected to the three connection projections, the tubular passage integrating connector 52 having three tubular passages respectively communicated with their openings. The three tubular passages are formed to penetrate the three joint portions constituting the tubular passage integrating connector 52.

One of the three joint portions is a water-supply tube connection joint portion 54 as shown in FIG. 5B, the water-supply tube connection joint portion 54 being formed into a tapered shape, the outer diameter of which is reduced forwards. Furthermore, the water-supply tube connection joint portion 54 has a recess 54a in the leading portion thereof. The recess 54a has openings of the foregoing penetrating tubular passages.

Other joint portions (omitted from illustration) respectively communicated with the suction connection tube 49 and the air-supply connection tube 50 are formed into the similar shape, the joint portions being integrally accommodated by the joint recess 22d and respectively forming recesses.

The recesses of the tubular passage integrating connector 52 receive and are connected to end portions of an external air-supply tube 55 constituting the air-supply tubular passage 26, an external water-supply tube 56 constituting the water-supply tubular passage 27 and an external suction tube 57 constituting the suction tubular passage 28. The other end portions of the external air-supply tube 55, the external water-supply tube 56 and the external suction tube 57 respectively are, as described above, connected to the air-supply source and the like of the fluid control apparatus 9.

It should be noted that the center of the longitudinal axis of the holding portion 12a is, as shown in FIG. 2, made eccentric in the direction opposing the curing tool insertion port 34 with respect to the central axis of the insert 14. Furthermore, the central axis of the insert cover coat 22c is made eccentric toward the curing tool insertion port 34 with respect to the central axis of the joint 22a.

The control-unit cover portion 23 and the universal-cord cover portion 24 of the cover 3 will now be described. The control-unit cover portion 23 shown in FIG. 1 is formed by making thin and soft resin into a sheet-like shape.

The universal-cord cover portion 24 is formed by a continuously cylindrical soft plastic sheet, the universal-cord cover portion 24 having a length that is several times longer than the overall length of the universal cord 13 of the endoscope that is intended to be used. The universal-cord cover portion 24 has perforations for cutting formed at predetermined intervals around the outer surface thereof. In slightly front of the perforations, a window 24a for connecting the signal cord 21 is formed as shown in FIG. 1.

The cord cover accommodating case 37 accommodates the universal cord cover portions 24 for a plurality of operations in such a manner that the universal cord cover portions 24 are compressed.

The insert cover portion 22 is ejected from a cover package (omitted from illustration) that packages the disinfected components of the cover 3. The cover holder 6 holds the insertion cover portion 22, followed by connecting the expansion tube 36 connected to the expander 10 to the expansion tube joint 35 provided for the insert cover portion 22. While supplying air into the endoscope insertion channel 25 to expand it, the cover-type endoscope 4 is inserted into the endoscope insertion channel 25.

Then, the connector 19 of the endoscope is fastened to the connector receptor 7a of the light source apparatus 7. An end portion of the universal-cord cover portion 24 is ejected from the cord cover accommodating case 37 to draw it to a position near the control unit body 12b, followed by covering the universal cord 13. Since the cutting perforations and the window 24a for connecting the cable are arranged to, at this time, appear in the universal cord cover portion 24 adjacent to the cord cover accommodating case 37, the window 24a is aligned to the connection portion of the connector 19 for connecting the signal cord 21. In this way, the signal cord 21 is connected.

When the universal-cord cover portion 24 is fastened to the cord 13, the external tubes 55, 56 and 57 are also covered with the same. Furthermore, control-unit cover portion 24 is fastened to the endoscope control unit 12, and also the external tubes 55, 56 and 57 are covered with the same. Then, the end portion of the opening of each of the external tubes 55, 56 and 57 is connected to the tubular passage integrating connector 52 of the joint 22a. Thus, the preparation is completed.

The end portions of the openings of the external tubes 55, 56 and 57 must be connected to the air-supply source and so forth of the fluid control apparatus 9. The procedure for covering the external tubular passages 55, 56 and 57 may be performed starting at the control unit.

Then, the insert cover portion 22, into which the insert 14 has been inserted, is inserted into the body cavity of a patient. Since the external tubes 55, 56 and 57 are allowed to extend from the side portion of the joint 22a at this time, the foregoing tubes do not hinder the insertion of, for example, the curing tool through the curing tool insertion port 34. Then, required inspections and curing operations are performed.

After the operation has been completed, the insert cover portion 22 and the control-unit cover 23 are removed, and the signal cord 21 is removed from the connector 19. Then, a clean universal-cord cover 24 is drawn until the perforations of the universal-cord cover portion 24 appear, followed by separating the used universal-cord cover portion 24 by cutting performed at the perforations. Then, the connector 19 is removed from the connector connection portion, followed by drawing and removing the used universal-cord cover portion 24 from the universal cord 13.

Since this embodiment has an arrangement that the tubular passages 26, 27 and 28 are made extend from the joint 22a in the side direction with respect to the longitudinal direction of the insert cover portion 22, the operation facility of the curing tool such as the forceps and facilities in rotating and twisting the control unit 12 can be improved.

Since the tubular passages 26, 27 and 28 can be, in the joint 22a, separated by the tubular passage integrating connector 52 at a position adjacent to the bent portions of the tubular passages 26, 27 and 28 toward the side portions, a substance, such as a substance clogged adjacent to the bent portion, can easily be removed even if the clogging takes place during the operation.

The arrangement of this embodiment that the case for accommodating the universal-cover portion 24 is provided for the connector receptor 7a of the light source apparatus 7 enables the necessity of hanging the universal cord 13 and the connector 19 on a hanger one by one at the time of fastening the cover to be eliminated. Therefore, the handling facility can be improved.

Since the cover accommodating case 37 accommodates the continuous universal cord covers 24 that can be used in a plurality of operations, setting of the cover at each operation does not need to be performed. That is, the universal cord covers 24 and the carrier accommodating case 37 can be collectively exchanged.

Since the holding portion 12a is made eccentric in the direction opposing the curing tool insertion port 34, the hand that holds the control unit 12 and the hand that inserts/removes the curing tool do not interfere with each other at the time of inserting/removing the curing tool. Therefore, the handling facility can be improved.

Although the tubular passages are separated from one another in the joint 22a in the foregoing embodiment, the tubular passages in the insert cover portion 22 may be integrated into a continuous form. Also in this case, the similar effect obtainable from the extension sidewards can be obtained.

Figures 6A, 6B:
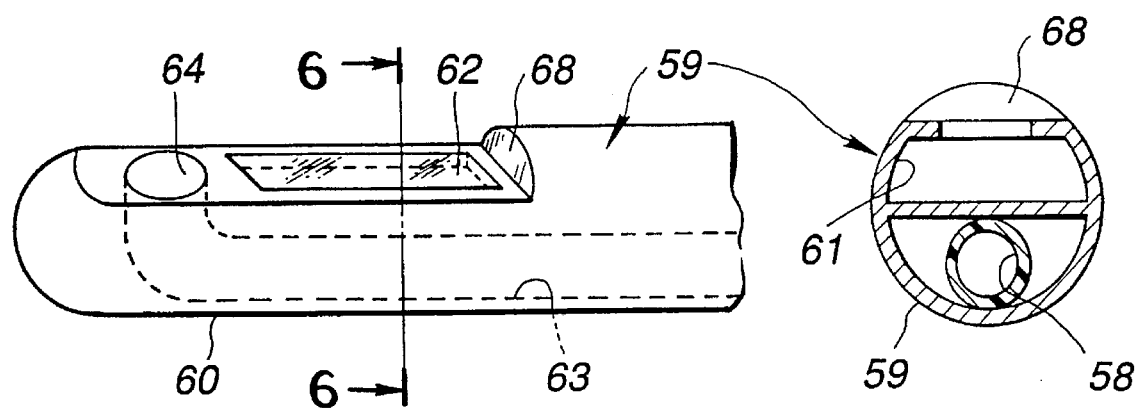
Figure 7A:
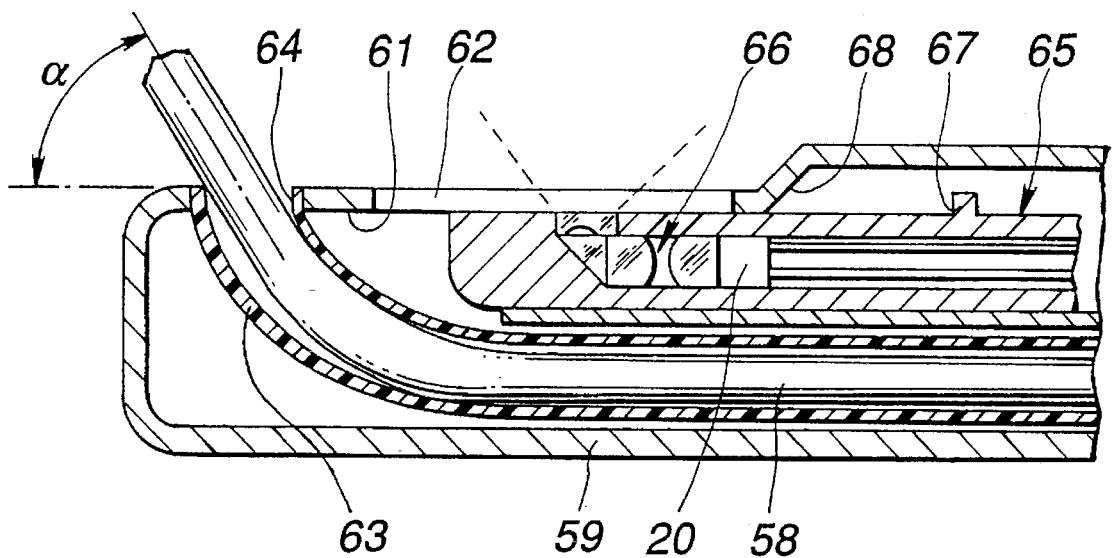
FIGS. 7(a) and 7(b) are side elevational cross sectional views which illustrate the operation of the cover-type endoscope.
Figure 7B:
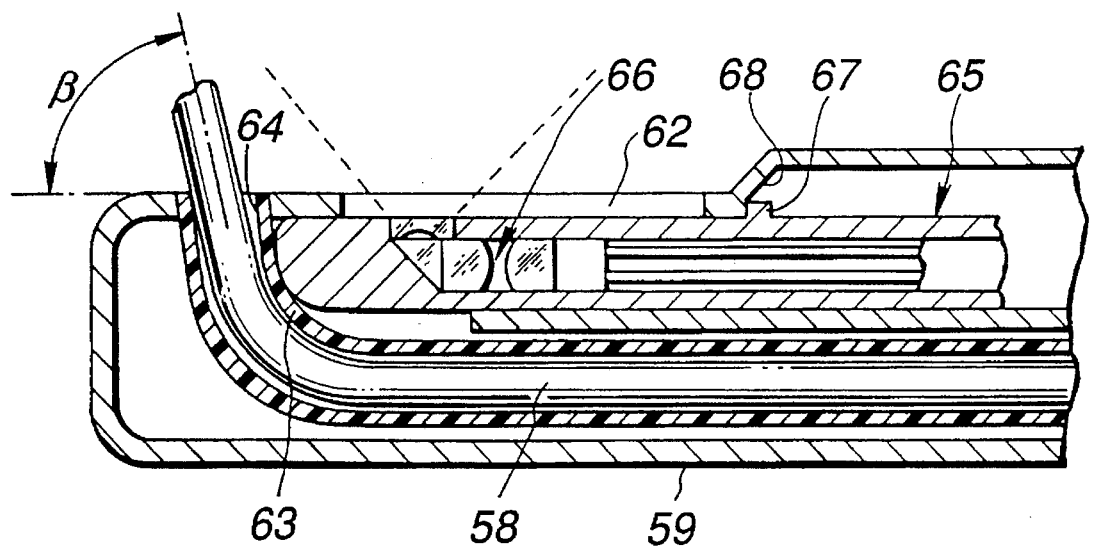

FIGS. 6(a)–(b) and 7 relate to a second embodiment of the present invention. FIG. 6(a) is a perspective view which illustrates a leading portion of a cover. FIG. 6(b) is a cross sectional view taken along line b—b of FIG. 6(a). FIGS. 7(a) and 7(b) respectively are side elevational cross sectional views which illustrate the operation of a cover-type endoscope.

As shown in FIGS. 6(b) and 7, an insert cover portion 59 of the cover according to this embodiment has an endoscope insertion channel 61 running from a leading portion 60 toward the rear position. As shown in FIG. 6(a), the leading portion 60 has, on the side surface thereof facing the endoscope insertion channel 61, an observation window 62. As shown in FIGS. 6(a) and 7, the insert cover portion 59 has, in addition to the endoscope insertion channel 61, a forceps channel 63 formed to pass though the insider thereof. A forceps outlet port 64 of the forceps channel 63 is formed on the same side surface in which the observation window 62 is formed.

Since the rear portion (adjacent to the operator) of the insert cover portion 59 is structured similarly to that according to the first embodiment, its description and drawing are omitted here.

FIGS. 7(a) and 7(b) show the side elevational cross section in a state where the forceps 58 has been inserted into the forceps channel 61 of the insert cover portion 59.

A cover-type endoscope 65 shown in FIGS. 7(a)–(b) includes, in the leading portion thereof, an objective optical system 66 and an irradiation optical system (omitted from illustration). In the rear of the objective optical system 66, the solid-state image sensing device 20 is disposed. The cover-type endoscope 65 has a stopper 67 to project over an intermediate position of the outer surface of the leading portion thereof.

The cover-type endoscope 65 is inserted into the endoscope insertion channel 61 of the insert cover portion 69 to be able to move forwards/rearwards even if the observation is being performed. The observation window 62 is formed to have a size that does not block the visual field of the objective optical system 66 even if the cover-type endoscope 65 is moved forwards/rearwards.

The leading portion 60 of the insert cover portion 59 has an abutting portion 68 adjacent to the endoscope insertion channel 61. As shown in FIGS. 7(a)–(b), the endoscope insertion channel 61 has, in the leading portion thereof, no channel component member disposed between the forceps channel 63 so that the wall of the channel appears outside. The forceps channel 63 is made of soft material.

In the foregoing structure, when the cover-type endoscope 65 is located at a position shown in FIG. 7(a), that is, when the leading portion of the cover-type endoscope 65 is not positioned in contact with the leading portion of the endoscope insertion channel 61, a rising angle of the forceps 58 is made as follows.

The forceps 58 inserted into the forceps channel 63 followed by projecting over the forceps outlet port 64 makes angle α as shown in FIG. 7(a).

When the cover-type endoscope 65 is further inserted by pressure, the leading portion of the cover-type endoscope 65 abuts against the leading portion of the endoscope insertion channel 61, that is, the side wall of the forceps channel 63 as shown in FIG. 7(b). It causes the portion of the forceps channel 63 adjacent to the forceps outlet port 64 to be further pushed forwards, resulting in angle β to be made by the forceps 69 that projects over the forceps outlet port 64 as shown in FIG. 7(b). That is, the angle β is made larger than the angle α. When a projection 67 of the endoscope abuts against the abutting portion 68 of the cover portion, the angle β is made largest.

When the cover-type endoscope 65 is slid in a range in which the directions α and β of the forceps 58 can be changed, the side portion can always be observed. That is, the endoscope 65 is arranged to have a visual field direction which is made sidewards.

This embodiment has an arrangement that the rising angle can be changed in accordance with the forward/rearward movement of the endoscope, enabling the direction in which the forceps is projected to be changed. As a result, the performance of targeting the curing tool, such as the forceps, can be improved.

Furthermore, the arrangement of the this embodiment restricts the abutting force by the projection 67 and the cover abutting portion 68 of the endoscope, preventing the endoscope 65 to break through the forceps channel 63.

The present invention is not limited to the electron-type endoscope. For example, it can be adapted to any kind of endoscopes, such as an optical fiber endoscope or an ultrasonic endoscope.

Figure 11:
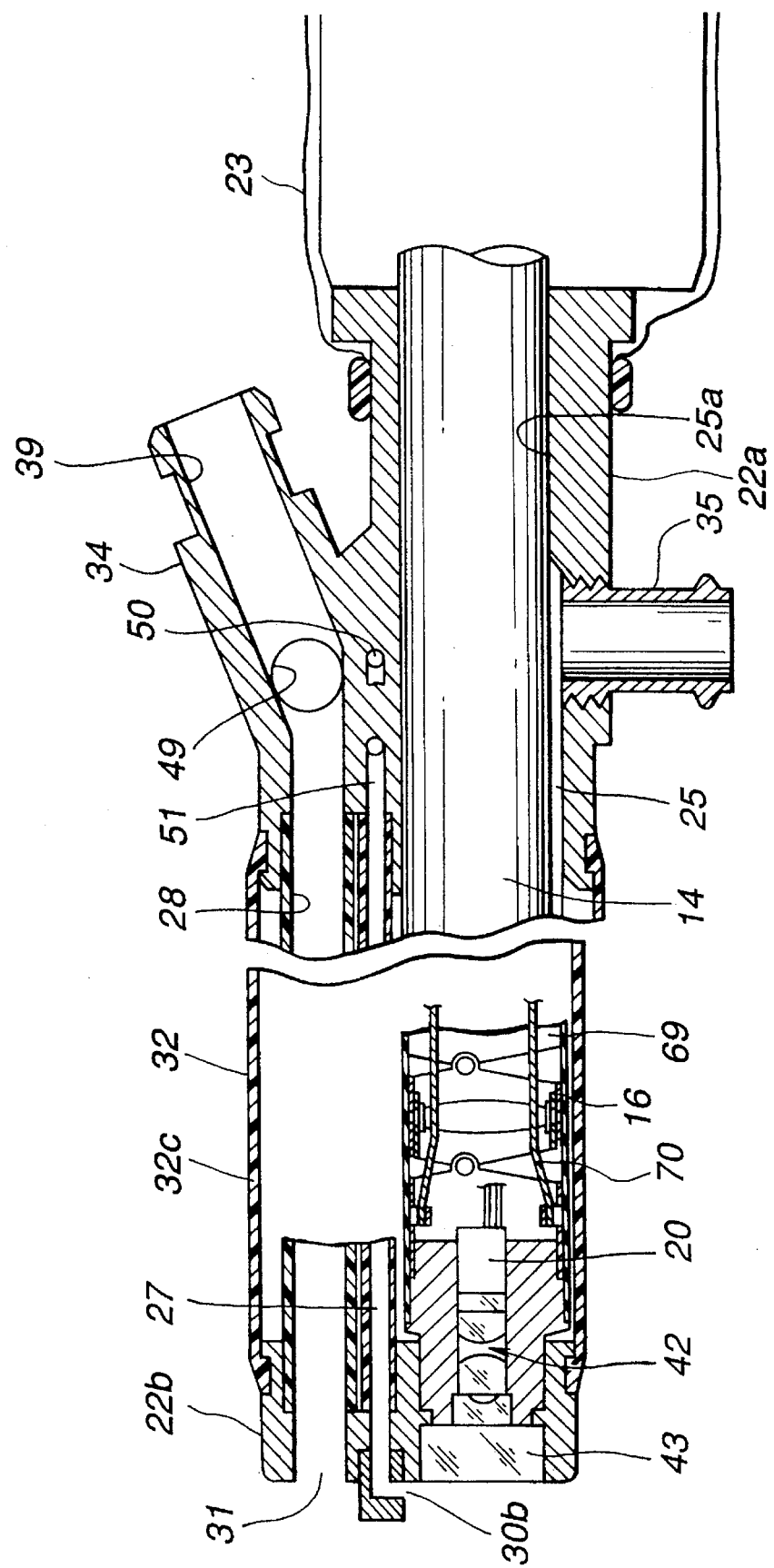
Figure 12A:
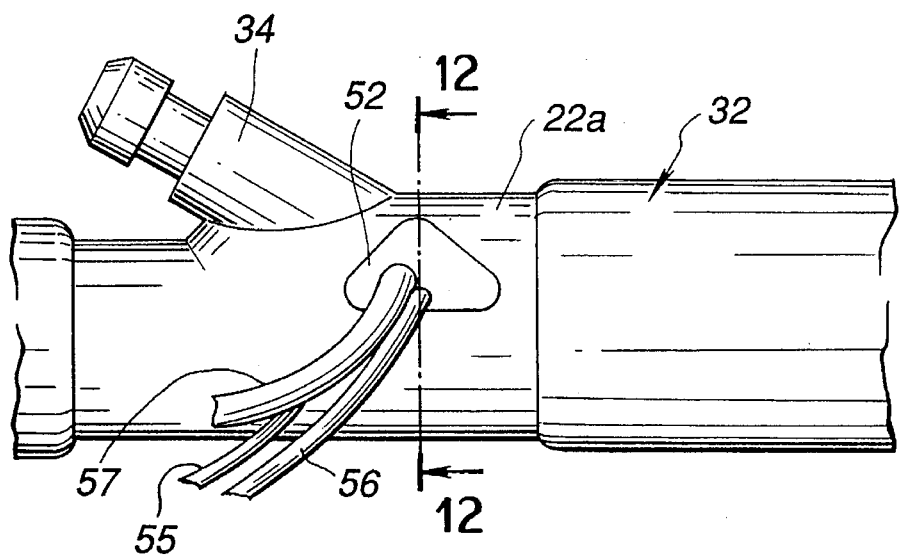
FIG. 12(a) is a side elevational view and FIG. 12(b) is a cross sectional view which illustrate the cover-system endoscope.

FIGS. 8 to 12(a)–(b) relate to a third embodiment of the present invention. FIG. 8 is an overall schematic view which illustrates an endoscope apparatus to which a cover-type endoscope is connected. FIG. 9 is a schematic view which illustrates a cover-type endoscope. FIG. 10(a) is a perspective view of the leading portions of the cover-type endoscope and FIG. 10(b) is an insert cover portion. FIG. 11 is a side elevational cross sectional view which illustrates the leading portion of the cover-system endoscope. FIG. 12(a) is a side elevational view and FIG. 12(b) is a cross sectional view which illustrate the cover-system endoscope.

An endoscope 29 shown in FIG. 8 is an apparatus to which an endoscope-cover-system endoscope (hereinafter abbreviated a "cover-type endoscope") 40 having channels can be attachably/detachably connected.

The cover-system endoscope 40 is constituted by combining an endoscope cover (hereinafter abbreviate to a "cover") 44 having channels and an endoscope-cover-type endoscope (hereinafter abbreviated to a "cover-type endoscope") 4 having channels. The cover-type endoscope 4 is an electronic-type endoscope.

The cover 44 covers an insert and the like of the cover-type endoscope 4 to eliminate the necessity of cleaning and disinfecting the endoscope to be performed after an inspection has been completed.

The endoscope apparatus 29 comprises the cover-system endoscope 40, a cart 5 accommodating various peripheral devices to which the cover-system endoscope 40 is connected, and a cover holder 6 for holding the cover-system endoscope 40.

The cart 5 shown in FIG. 8 and accommodating the peripheral devices accommodates, for example, a light source apparatus 7, a video processor 8, a fluid control apparatus 9, and an expander (hereinafter abbreviated to an "expander") 10 for an endoscope-cover having channels. The cart 5 holds a monitor 11 placed on the ceiling plate thereof.

The light source apparatus 7 supplies irradiation light to the cover-type endoscope 4 of the cover-system endoscope 40. The video processor 8 is connected to the electronic-type cover-type endoscope 4 to convert an electric signal supplied from the endoscope 4 into a standard video signal, followed by outputting the video signal to the monitor 11. The monitor 11 receives the video signal to display an image of the endoscope 4.

The fluid control apparatus 9 supplies air/water through tubular passages formed in the cover 44 and serving as channels to be described later. Therefore, the fluid control apparatus 9 has a water-supply source and an air-supply source (omitted from illustration). The tubular passages connected to the air-supply source and the water-supply source are controlled by electromagnetic valves to be opened/closed as desired.

The expander 10 supplies air into the cover 44 to expand the cover 44. As a result of the expansion, the cover-type endoscope 4 can easily be fastened to or removed from the cover 44.

As shown in FIG. 9, the cover-type endoscope 4 comprises a control unit 12, a universal cord 13 extending from the side portion of the control unit 12, and an insert 14 connected to the control unit 12. The insert 14 of the cover-type endoscope 4, as shown in FIG. 9, comprises a flexible tube portion 15, a warp-enabled portion 16 that can be warped, and a hard leading portion 17 when viewed from the base portion of the control unit 12 toward the leading portion.

The insert 14 of the cover-type endoscope 4 has a small diameter and has a D-shape cross sectional shape as shown in FIG. 10(a). As shown in FIG. 10(a), the leading portion 17 of the cover-type endoscope 4 has irradiation optical systems 41a and 41b and an objective optical system 42 disposed therein. It should be noted that the insert 14 of the endoscope 4 may be formed into a cylindrical shape.

At the rear ends of the irradiation optical systems 41a and 41b, light emission ends of light guide fibers (omitted from illustration) are disposed. The light guide fibers are allowed to pass through the insert 14, the control unit 12 and the universal cord 13.

The universal cord 13 has, at an end portion thereof, a connector 19. The connector 19 is attachably/detachably connected to a connection receptor 7a provided for the light source apparatus 7. As a result, irradiation light can be supplied from the light source apparatus 7 to the incidental ends of the light guide fibers.

The connector receptor 7a of the light source apparatus 7 has a cord-cover accommodating case 37 to surround the connector receptor 7a. The cord-cover accommodating case 37 is formed into a box-like shape to accommodate a disposable-type universal cord cover portion to be described later, the cord-cover accommodating case 37 having, in the front surface thereof, an opening through which the connector 19 is allowed to pass.

As shown in FIG. 11, a solid-state image sensing device 20 for converting an incident optical image into an electric signal is disposed at the rear end of the objective optical system 42. The electric signal transmitted from the solid-state image sensing device 20 is received by the video processor 8 via a signal cord 21 extending from the side portion of the connector 19 shown in FIG. 8 and so forth.

The warp-enabled portion 16 of the cover-type endoscope 4 includes a plurality of warping blocks 69 combined rotatively. End portions of the warp controlling wires 70 are connected to the leading block among the warping blocks 69, while the other end portions of the same are fixed to the control unit 12.

As shown in FIG. 2, the control unit 12 has a holding portion 12a at the base portion thereof. Furthermore, a control unit body 12b is connected to the upper portion of the holding portion 12a. The control unit 12b of the control unit 12 has an angle knob 45, an air-supply/water-supply control switch 46, a suction control switch 47, and a function switch 48 for taking a photograph each disposed therein.

The angle knob 45 is attachably/detachably provided with respect to the control unit body 12b.

As shown in FIG. 8, the cover 44 for covering the cover-type endoscope 4 is composed of an insert cover portion 32, a control-unit cover portion 23, and a universal-cord cover portion 24. The insert cover portion 32 of the cover 44 covers the insert 14 of the cover-type endoscope 4. The control-unit cover portion 23 of the cover 44 covers the control unit 12 of the cover-type endoscope 4 and three tubular passages to be described later. The universal-cord cover portion 24 of the cover 44 covers the universal cord 13 of the cover-type endoscope 4 and three tubular passages to be described later. All portions of the cover 44 are fastened to the cover-type endoscope 4 so that the endoscope-type endoscope 4 is covered with the cover 44 hermetically with respect to water.

The cover holder 6 shown in FIG. 8 has an arm portion 6a that holds the insert cover portion 32 at the time of fastening the insert cover portion 32 to the cover-type endoscope 4. As a result, the endoscope 4 can sanitarily be held because the hand does not touch the cover 44. Furthermore, the operation can easily be performed.

FIG. 11 is a side elevational cross sectional view which illustrates a state where the cover-type endoscope 4 is inserted into the insert cover portion 32 of the cover 44.

The insert cover portion 32 is used to isolate the insert 14 of the cover-type endoscope 4 from the external environment. The insert cover portion 32 is formed into an elongated shape, the insert cover portion 22 having a joint 2a (hereinafter abbreviated to a "joint") for fixing the control unit 12 of the endoscope 4, that is a unit adjacent to the operator, and a leading unit portion 22b that are made of hard material, for example, metal or resin.

The portion between the joint 22a of the insert cover portion 32 and the leading unit portion 22b is hermetically covered with an insert-cover coat 32c made of flexible material. The insert cover coat 32c is, at the leading portion thereof, connected to be received by an edge portion formed around the outer surface of the rear portion of the leading unit portion 22b. The insert cover coat 32c is similarly connected in a portion adjacent to the joint 22a.

Furthermore, the insertion cover portion 32 includes a endoscope insertion channel 25 through which the insert 14 is able to pass, and an air-supply tubular passage 26, a water-supply tubular passage 27 and a suction tubular passage 28 serving as the channels.

The insert-cover coat 32c is made of resin, such as polyurethane, that exhibits excellent chemical resistance and that is relatively flexible. The cover coat 32c is made of mixing a plurality of resins having difference hardness while changing the mixture ratio of the resins. The mixture ratio is change in a direction of the longitudinal axis of the insert cover portion 32. For example, the insert cover coat 32c is formed to have the hardness that is gradually raised from its leading portion toward the base portion. That is, the insert cover coat 32c has different flexibility between its leading portion and its base portion.

The way of changing the flexibility of the insert cover coat 32 is arbitrarily determined in accordance with the subject internal organ. For example, the insert cover coat 32 for an endoscope for the large intestine is formed softest at its position that corresponds to the warp-enabled portion 16, the insert cover coat 32 being made slightly harder than the hardness of the foregoing portion in a portion from the warp-enabled portion 16 to a predetermined rearward position, for example, to a position about 30 cm distant from the leading portion. The hardness is further raied from the foregoing predetermined position to the base portion.

The deeper the leading portion of the insert cover portion 32, into which the cover-type endoscope 4 has been inserted, is inserted into, for example, the body, the more the insertion force acting on the portion, such as the cover portion 32, adjacent to the operator tends in comparison to the force acting on the leading portion. That is, it means a fact that the portion adjacent to the operator can be easily kinked in comparison to the leading portion.

The foregoing structure has an arrangement that the flexibility is changed to have the hardness of the insert cover coat 32 that is raised toward the portion adjacent to the operator. Therefore, the insert cover portion 32 cannot easily be bent and kinked than the leading portion when it approaches the portion adjacent to the operator.

The embodiment has the arrangement that the leading portion of the cover portion 32 corresponding to the position of the warp-enabled portion 16 is more flexible than the rear portion even if the insert cover portion 32 is fastened to the cover-type endoscope 4. Therefore, the cover-type endoscope 4 can easily be inserted. In particular, it can easily be inserted even into the body cavity that has many bends.

The insert cover portion 32 according to the present invention can be protected from bending that starts at its leading portion even if the leading portion is inserted deeply into the body. Therefore, occurrence of a kink can be prevented, and, accordingly, the insertion operation can easily be performed.

Since this embodiment has an arrangement that the portion of the insert cover portion 32 corresponding to the warp-enabled portion 16 is so soft that the warp can be easily realized.

By changing the flexibilities of the tubular passages 26, 27 and 28 similarly to the cover coat 32, a further satisfactory effect can be obtained.

Namely, the material of each of the suction tubular passage 28 also serving as the channel for the curing tool, the air-supply tubular passage and the water-supply tubular passage is made of material obtained by mixing a plurality of resins that have different hardness, and their mixture ratio is changed to form the foregoing element.

The endoscope insertion channel 25 has, in the base portion thereof, an opening 25a for inserting the insert 14 in the joint 22a. The opening 25a of the endoscope insertion channel 25 is arranged to receive the end portion of the insert 14 adjacent to the operator. It should be noted that the opening 25a may be arranged to receive the base portion of the endoscope control unit 12. The endoscope insertion channel 25 is closed in the leading unit portion 22b so that the insert 14 of the cover-type endoscope 4 can be hermetically isolated from the outer environment.

The leading unit portion 22b of the insert cover portion 32 has, at the leading portion of the endoscope insertion channel 25, a transparent window 43 as shown in FIG. 10B. The window 43 has a size capable of including the irradiation optical systems 41a and 41b and the objective optical system 42 of the cover-type endoscope 4, the window 43 being formed to face the foregoing optical systems 41a, 41b and 42. The window 43 is formed into a shape to be adaptable to the semicircular shape of the leading portion 17 of the endoscope 4.

The leading unit portion 22b of the insert cover portion 32 has an air-supply nozzle 30a, a water-supply nozzle 30b and an opening 31 each of which is opened toward the window 43. The air-supply and water-supply nozzles 30a and 30b respectively are communicated with and connected to the air-supply tubular passage 26 and the water-supply tubular passage 27. The opening 31 is communicated with and connected to the suction tubular passage 28.

As described later, the air-supply tubular passage 26, the water-supply tubular passage 27 and the suction tubular passage 28 are allowed to extend from the side portion of the joint 22a, and their end portions are respectively opened.

As shown in FIG. 8, the air-supply tubular passage 26 is communicated with and connected to the air-supply source (omitted from illustration) of the fluid control apparatus 9. The water-supply tubular passage 27 is communicated with and connected to the foregoing air-supply source via a water-supply tank 33, which is the water-supply source. Furthermore, the suction tubular passage 28 is communicated with and connected to a suction bin (omitted from illustration) and a suction source (omitted from illustration).

A curing tool insertion port 34 and an expansion tube joint 35 project over the side portion of the joint 22a as shown in FIG. 11. The expansion tube joint 35 includes the internal tubular passage that is connected to the endoscope insertion channel 25. An expansion tube 36 connected to the expander 10 is attachably/detachably connected to the expansion tube joint 35.

The curing tool insertion port 34 projects diagonally rearwards with respect to a direction of the longitudinal axis of the insert cover portion 32. The internal tubular passage of the curing tool insert port 34 is opened at the end portion thereof, while another end portion is connected to the suction tubular passage 28. That is, the suction tubular passage 28 also serves as a tubular passage for the curing tool channel at the leading portion thereof. Therefore, the opening 31 is an outlet port for the curing tool.

The curing tool insertion port 34 receives a forceps cap 38 having a packing 38a made of an elastic material.

As shown in FIG. 11, the air-supply tubular passage 26, the water-supply tubular passage 27 and the suction tubular passage 28 are, at their rear end portions, bent in the joint 22a, and respectively include the following connection tubes.

In the rear of the suction tubular passage 28, a curing tool insertion passage 39 connected to the curing tool insertion port 34 is formed. At the branch point of the tubular passage forming the suction tubular passage 28 from the leading unit portion 22b to an intermediate point of the joint 22a and the foregoing curing tool insertion passage 39, a suction connection tube 49 is branched sidewards with respect to the direction of the longitudinal axis of the insertion cover portion 32. That is, the suction tubular passage 28 bents sidewards to extend with respect to the longitudinal axis of the insertion cover portion 32.

Similarly, the rear portions of the air-supply tubular passage 26 and the water-supply tubular passage 27 respectively formed into an air-supply connection passage 50 and a water-supply connection passage 51 extending sidewards in the joint 22a with respect to the longitudinal axis of the insertion cover portion 32. In order to prevent interfere occurring among the tubular passages, the air-supply connection tube 50 of the air-supply tubular passage 26 is bent at a position more rearwards than the water-supply connection tube 51 of the water-supply tubular passage 27.

Figure 12B:
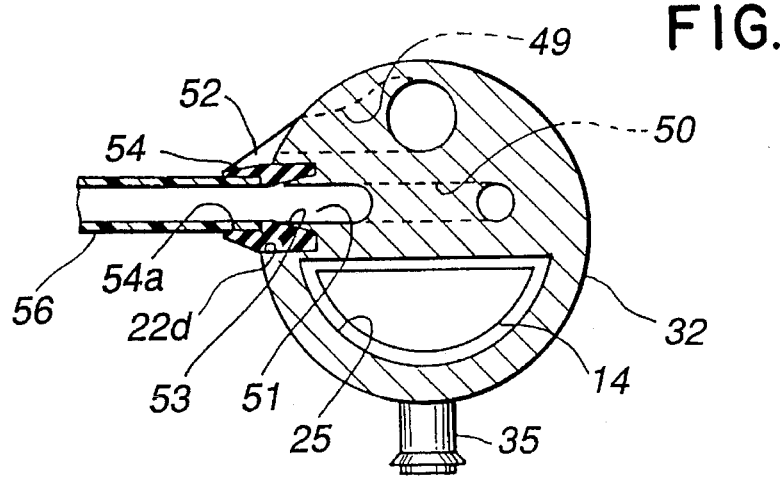

As shown in FIG. 12(a) which is a side elevational view, the joint 22a of the insert cover portion 32 has a tubular passage integrating connector 52 in the side portion thereof. The tubular passage integrating connector 52 is, in the joint 22a, disposed below the curing tool insertion port 34 at a position different in the circumferential direction. FIG. 12(b) is a cross sectional view taken along line 12—12 of FIG. 12(a).

The tubular passage integrating connector 52 is made of elastic material and is hermetically connected to a joining recess 22d formed in the side portion of the joint 22a as shown in FIG. 12(b). The recess 22d has three connection projections in which the openings of the suction connection tube 49, the air-supply connection tube 50 and the water-supply connection tube 51 are respectively formed. It should be noted that FIG. 12(b) shows only a connection projection 53 for the water-supply connection tubular passage 51.

The tubular passage integrating connector 52 is hermetically connected to the three connection projections, the tubular passage integrating connector 52 having three tubular passages respectively communicated with their openings. The three tubular passages are formed to penetrate the three joint portions constituting the tubular passage integrating connector 52.

One of the three joint portions is a water-supply tube connection joint portion 54 as shown in FIG. 12B, the water-supply tube connection joint portion 54 being formed into a tapered shape, the outer diameter of which is reduced forwards. Furthermore, the water-supply tube connection joint portion 54 has a recess 54a in the leading portion thereof. The recess 54a has openings of the foregoing penetrating tubular passages.

Other joint portions (omitted from illustration) respectively communicated with the suction connection tube 49 and the air-supply connection tube 50 are formed into the similar shape, the joint portions being integrally accommodated by the joint recess 22d and respectively forming recesses.

The recesses of the tubular passage integrating connector 52 receive and are connected to end portions of an external air-supply tube 55 constituting the air-supply tubular passage 26, an external water-supply tube 56 constituting the water-supply tubular passage 27 and an external suction tube 57 constituting the suction tubular passage 28. The other end portions of the external air-supply tube 55, the external water-supply tube 56 and the external suction tube 57 respectively are, as described above, connected to the air-supply source and the like of the fluid control apparatus 9.

It should be noted that the center of the longitudinal axis of the holding portion 12a is, as shown in FIG. 9, made eccentric in the direction opposing the curing tool insertion port 34 with respect to the central axis of the insert 14. Furthermore, the central axis of the insert cover coat 22c is made eccentric toward the curing tool insertion port 34 with respect to the central axis of the joint 22a.

The control-unit cover portion 23 and the universal-cord cover portion 24 of the cover 44 will now be described. The control-unit cover portion 23 shown in FIG. 8 is formed by making thin and soft resin into a sheet-like shape.

The universal-cord cover portion 24 is formed by a continuously cylindrical soft plastic sheet, the universal-cord cover portion 24 having a length that is several times longer than the overall length of the universal cord 13 of the endoscope that is intended to be used. The universal-cord cover portion 24 has perforations for cutting formed at predetermined intervals around the outer surface thereof. In slightly front of the perforations, a window 24a for connecting the signal cord 21 is formed as shown in FIG. 8.

The cord cover accommodating case 37 accommodates the universal cord cover portions 24 for a plurality of operations in such a manner that the universal cord cover portions 24 are compressed.

The insert cover portion 32 is ejected from a cover package (omitted from illustration) that packages the disinfected components of the cover 44. The cover holder 6 holds the insertion cover portion 32, followed by connecting the expansion tube 36 connected to the expander 10 to the expansion tube joint 35 provided for the insert cover portion 32. While supplying air into the endoscope insertion channel 25 to expand it, the cover-type endoscope 4 is inserted into the endoscope insertion channel 25.

Then, the connector 19 of the endoscope is fastened to the connector receptor 7a of the light source apparatus 7. An end portion of the universal-cord cover portion 24 is ejected from the cord cover accommodating case 37 to draw it to a position near the control unit body 12b, followed by covering the universal cord 13. Since the cutting perforations and the window 24a for connecting the cable are arranged to, at this time, appear in the universal cord cover portion 24 adjacent to the cord cover accommodating case 37, the window 24a is aligned to the connection portion of the connector 19 for connecting the signal cord 21. In this way, the signal cord 21 is connected.

When the universal-cord cover portion 24 is fastened to the cord 13, the external tubes 55, 56 and 57 are also covered with the same. Furthermore, control-unit cover portion 24 is fastened to the endoscope control unit 12, and also the external tubes 55, 56 and 57 are covered with the same. Then, the end portion of the opening of each of the external tubes 55, 56 and 57 is connected to the tubular passage integrating connector 52 of the joint 22a. Thus, the preparation is completed.

The end portions of the openings of the external tubes 55, 56 and 57 must be connected to the air-supply source and so forth of the fluid control apparatus 9. The procedure for covering the external tubular passages 55, 56 and 57 may be performed starting at the control unit.

Then, the insert cover portion 32, into which the insert 14 has been inserted, is inserted into the body cavity of a patient. Since the flexibility of the insert cover portion 32 is varied in the direction of the longitudinal axis as described above, the insertion can be performed while preventing the occurrence of the kink. Then, required inspections and curing operations are performed.

After the operation has been completed, the insert cover portion 32 and the control-unit cover 23 are removed, and the signal cord 21 is removed from the connector 19. Then, a clean universal-cord cover 24 is drawn until the perforations of the universal-cord cover portion 24 appear, followed by separating the used universal-cord cover portion 24 by cutting performed at the perforations. Then, the connector 19 is removed from the connector connection portion, followed by drawing and removing the used universal-cord cover portion 24 from the universal cord 13.

Since this embodiment has the arrangement that the flexibility is so changed to raise the hardness of the insert cover coat 32 in a direction toward the operator, the insertion operation can easily be performed. Since the insert cover portion in the warp-enabled portion is soft enough to warp the insert, that is, since the leading portion is made satisfactorily soft, the force required to operate the angle knob 45 can be reduced. Furthermore, this embodiment enables the insertion facility to be improved.

Figure 14:
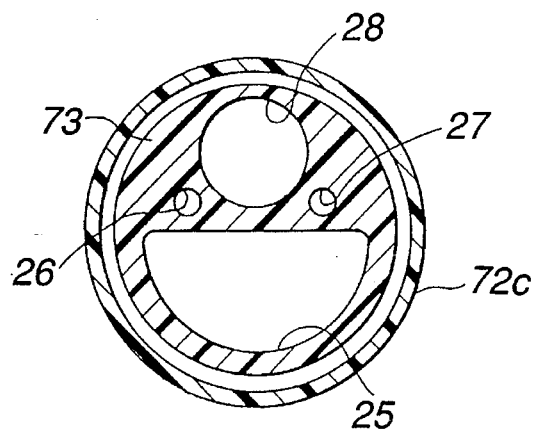
FIGS. 13 to 14 relate to a fourth embodiment of the present invention.
Figure 13:
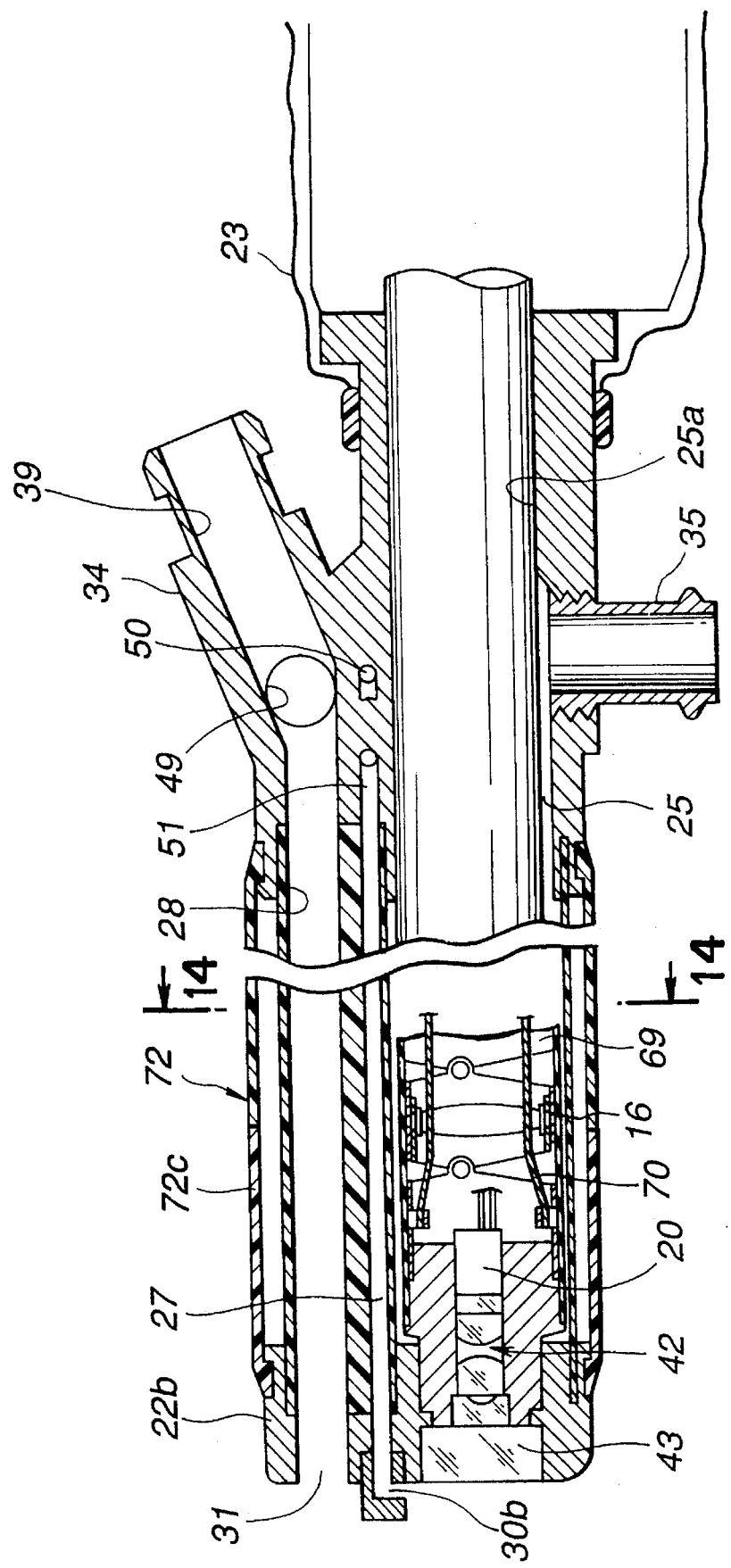

FIGS. 13 to 14 relate to a fourth embodiment of the present invention. FIG. 13 is a side elevational view which illustrates a cover-system endoscope. FIG. 14 is a cross sectional view taken along line 14—14 of FIG. 13.

An insert cover portion 72 according to the fourth embodiment has a cover coat 72c structured different from that according to the third embodiment.

The same structures and operations as those of the third embodiment are given the same reference numerals and their descriptions are omitted here. Therefore, only the different portions will now be described.

As shown in FIG. 13, the portion between the leading unit 22b and the joint 22a is hermetically covered with an insert-cover coat 72c made of flexible material. The insert-cover coat 72c is connected at its leading portion which is received by an edge portion formed around the rear end portion of the leading unit portion 22b. The insert-cover coat 22c is similarly connected in the vicinity of the joint 22a.

Furthermore, a multi-lumen tube 73 is interposed in the cover coat 72c. The multi-lumen tube 73 similarly establishes the connection between the leading unit portion 22b and the joint 22a.

As shown in FIG. 14, the multi-lumen tube 73 integrally forms the leading portions of the tubular passages 26, 27 and 28 and the channel 25. As a result of the thus arranged structure, irregular pass of each of the tubular passages can be prevented, and as well as the assembling facility can be improved, resulting in the reduction in the manufacturing cost.

The cover coat 72c is made of resin having a low hardness from its leading portion to an intermediate position, while the same is made of resin having a high hardness from the foregoing intermediate position toward the operator. The two types of the resins having different hardness are connected by heat welding or ultrasonic welding.

Also the multi-lumen tube 73 has the flexibility that is changed in the longitudinal direction thereof similarly to the third embodiment. That is, the multi-lumen tube 73 is made of a plurality of resins that have different hardness, and the mixture ratio is changed so that the leading portion is made softer than the rear portion.

The way of changing the flexibility of the insert cover coat 72 may be arbitrarily employed similarly to the third embodiment. As an alternative to this, three or more kinds of resins may be connected.

This embodiment enables the hardness (flexibility) to be rapidly changed. Since the other structures, operations and effects are the same as those obtainable from the third embodiment, their descriptions are omitted here.

Figure 15:
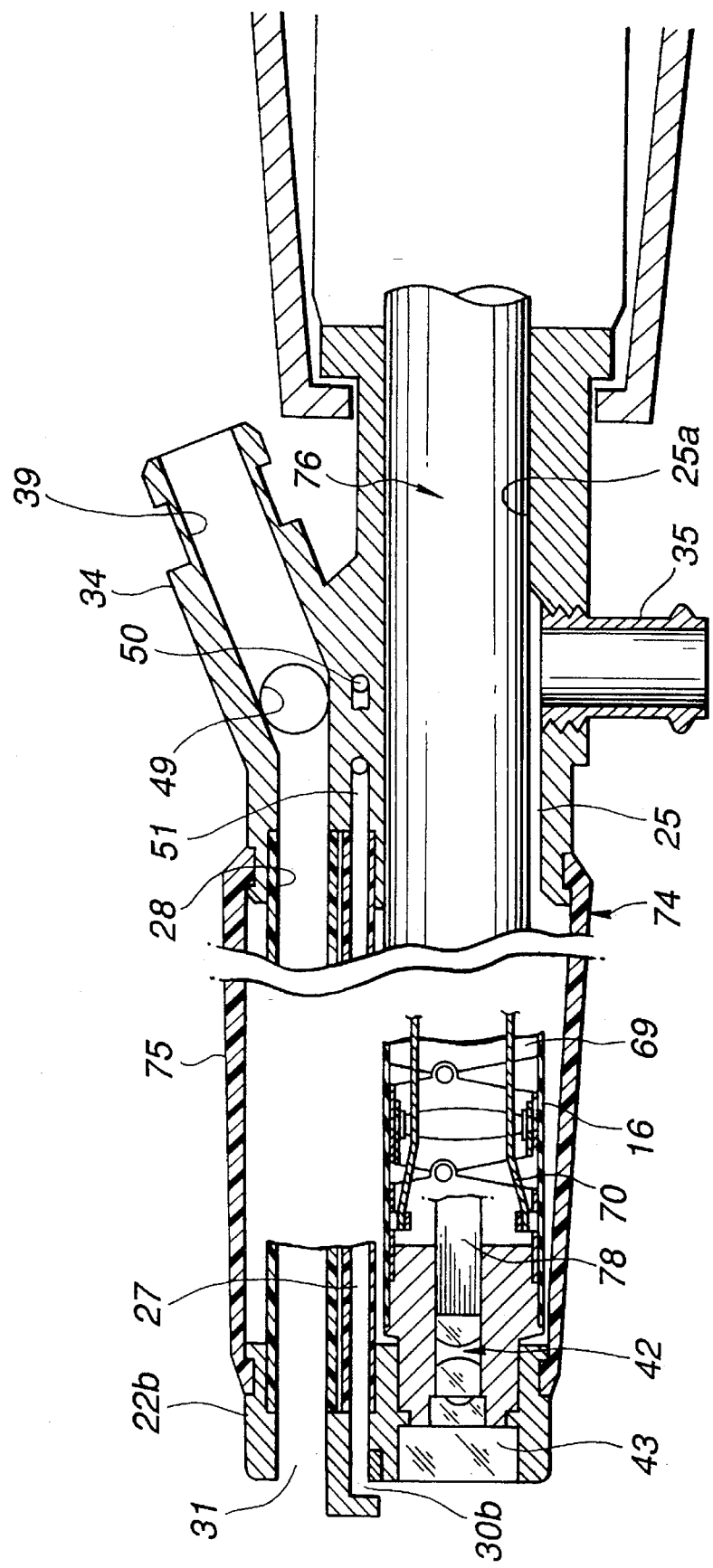
FIGS. 15 to 21 relate to a fifth embodiment of the present invention.
Figure 16:
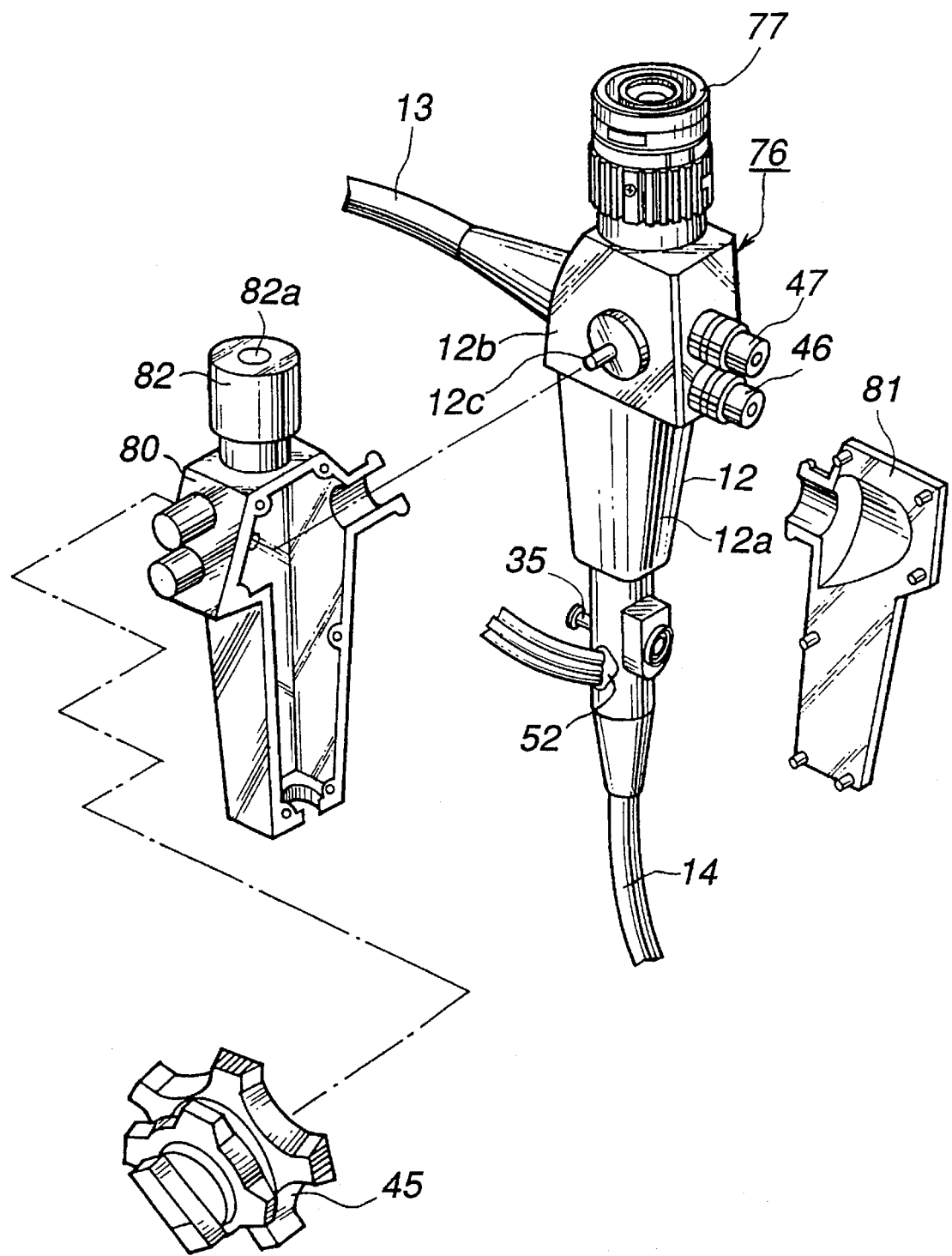
Figure 17:
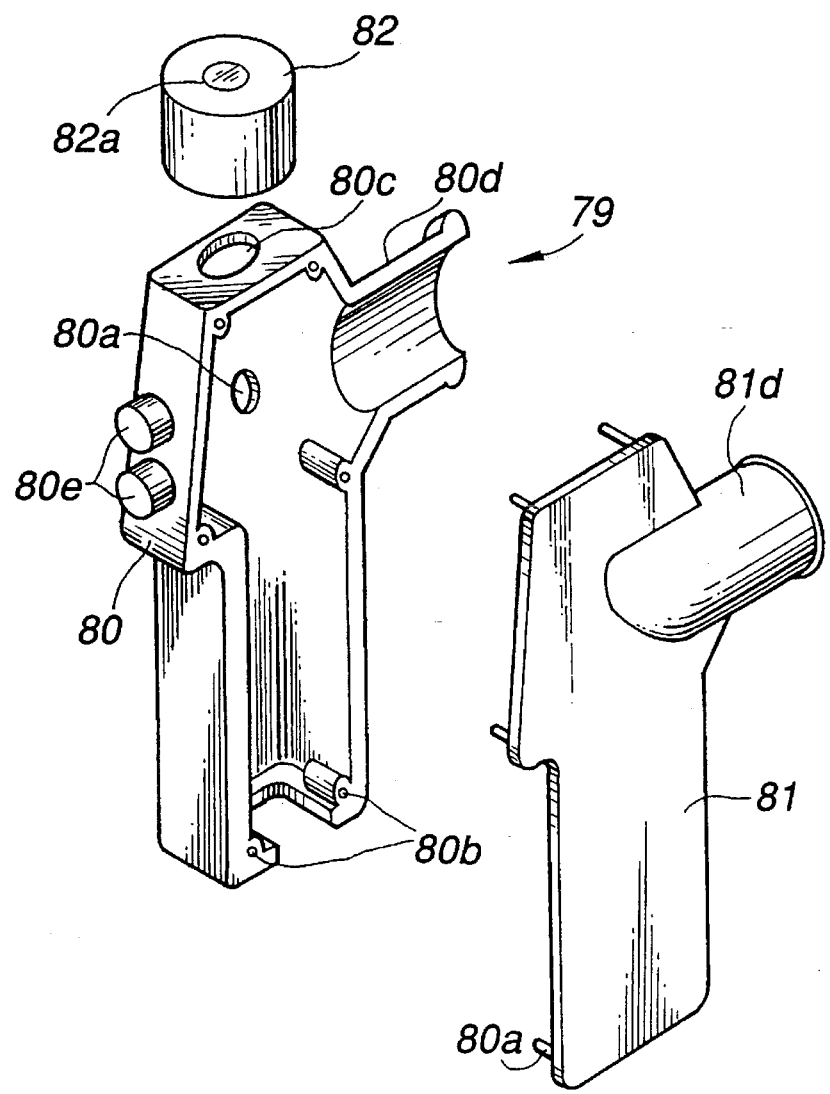
Figure 18:
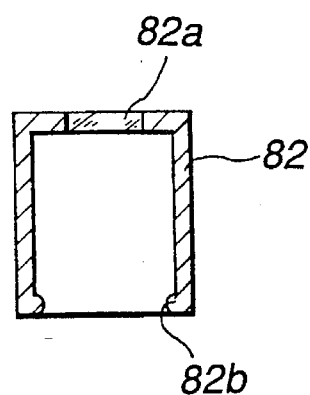
Figure 19:
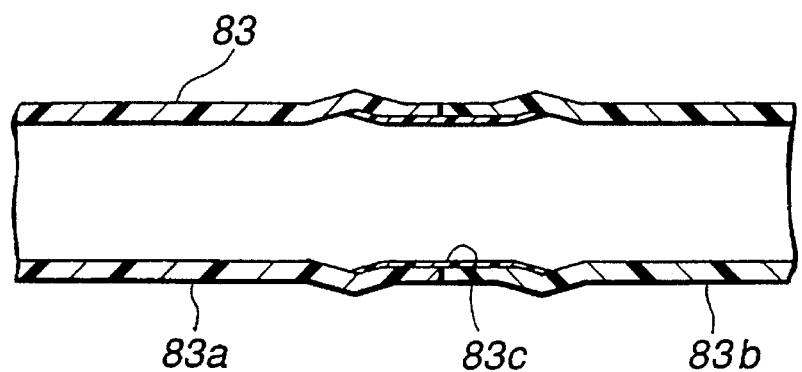
Figure 20:
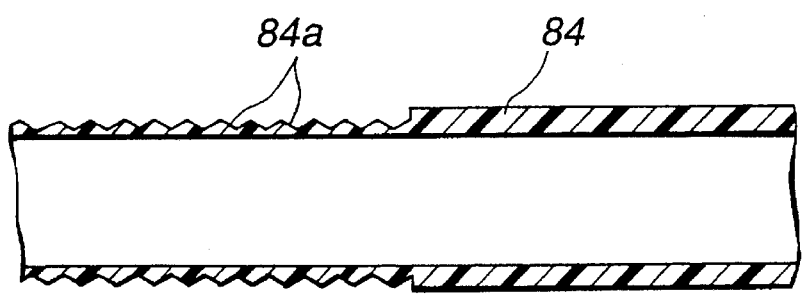
Figure 21:
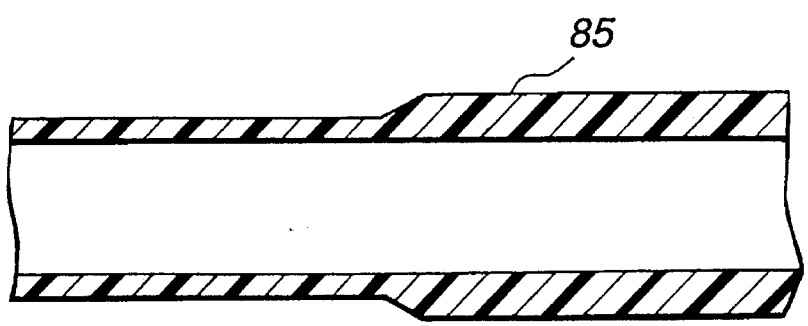

FIGS. 15 to 21 relate to a fifth embodiment of the present invention. FIG. 15 is a side elevational cross sectional view which illustrates a cover-system endoscope. FIG. 16 is an assembly drawing which illustrates the endoscope, the control unit cover and the angle knob. FIG. 17 is a perspective view which illustrates a control-unit cover portion. FIG. 18 is a cross sectional view which illustrates an ocular portion cover. FIG. 19 is a cross sectional view which illustrates a cover coat. FIG. 20 is a cross sectional view which illustrates the cover coat. FIG. 21 is a cross sectional view which illustrates the cover coat.

The fifth embodiment has an arrangement that the electronic endoscope according to the third embodiment is replaced by an optical fiber endoscope. Furthermore, this embodiment employs a cover coat, the thickness of which is changed in the longitudinal direction thereof, in place of the cover coat according to the third embodiment. Furthermore, the structure of the control unit cover portion according to this embodiment is different from that according to the third embodiment.

The same structures and operations as those of the third embodiment are given the same reference numerals and their descriptions are omitted here. Therefore, only the different portions will now be described.

A cover coat 75 of an insert cover portion 74 is made of resin similarly to the third embodiment. The cover coat 75 is arranged to have the thickness that is gradually increased from its leading portion toward the operator so that the flexibility is changed. The way of changing the flexibility is so arranged that the thickness is arbitrarily set in accordance with the applied positions.

A cover-type endoscope 76 shown in FIG. 16 has an ocular portion 77 connected to an end portion of the control unit 12 adjacent to the operator. The control unit 12 has not the function switch 48 according to the third embodiment.

The cover-type endoscope 76 has an image guide 78 disposed in the rear of the objective optical system 43, the image guide 78 being allowed to pass through the insert 14, the control unit 12 and the ocular portion 77. The rear end portion of the image guide 78 is disposed at the leading portion of an ocular optical system (omitted from illustration) of the ocular portion 77.

The angle knob 45 is attachably/detachably fastened to a shaft 12c projecting over the side surface of the control unit 12.

A control unit cover 79 is composed of a first control-unit cover 80 for covering the side portion adjacent to the angle knob 45, a second control-unit cover 81 for covering the opposing side portion, and an ocular portion cover 82 for covering the ocular portion 77 and made of elastic material. The control unit cover 79 is made of material such as plastic or rubber that has elasticity.

The first control-unit cover 80 has a shaft hole 80a, six fixing holes 80b and an ocular-portion through hole 80c. The first control-unit cover 80 has, in the side portion thereof, switch accommodating portions 80e for accommodating the switches 46 and 47 fastened thereto and enabling the switches 46 and 47 to be switched on/off.

The second control-unit cover 81 has six fixing pins 81a to be received by the fixing holes 80b.

The first and second control-unit covers 80 and 81 respectively have projecting cord connection covers 80d and 81d for covering the portion adjacent to the connection portions of the universal cord 13.

The ocular-portion cover 82 has a diopter adjustment lens 82a on the leading surface thereof. The ocular-portion cover 82 has the rear end portion that is engaged to the ocular hole 80c formed in the cover 80.

The control-unit cover portion 79 is arranged so that the first control-unit cover 80 is fastened from the position adjacent to the angle knob 45. After the first control-unit cover 80 has been fastened, the angle knob 45 is fastened to the shaft 12c of the control unit 12. Then, the second control-unit cover 81 is connected to the first cover portion 80, and then the ocular portion 77 is fastened to the endoscope 76. Then, the ocular portion cover 82 is used to cover the ocular portion 77.

FIG. 18 is a cross sectional view which illustrates the ocular-portion cover 82. The ocular-portion cover 82 has elasticity so that it can be fixed to the ocular portion 77 by an interference 82b.

The diopter adjustment lens 82a is adaptable to a plurality of the ocular-portion covers 82 in a range from −8 to +2 diopter so that the user is allowed to select the ocular-portion cover 82 adaptable to the diopter of the user.

This embodiment is adaptable even if the diopter is different among observers. That is, a suitable diopter adjustment lens 82a is selected to perform an observation at the proper diopter.

The first control unit cover 80 and the ocular-portion cover 82 may be formed integrally as shown in FIG. 16. In this case, the diopter adjustment lens 82a is also provided for the ocular portion cover.

FIGS. 19 to 21 are side elevational cross sectional views which illustrate an insertion channel also serving as a suction tubular passage, this arrangement being a modification of the foregoing embodiment. The insertion channel is provided in place of the tubular passage that constitutes the leading portion of the suction tubular passage 28 according to each of the foregoing embodiments.

An insertion channel 83 shown in FIG. 19 establishes the connection between two tubes 83a and 83b having different hardness by a connection tubular member 83c. In place of the connection tubular member 83c, they may be connected to each other by heat welding. Also the insert cover portion may be structured similarly to the structure shown in FIG. 19.

In the foregoing manner, the flexibility of the insertion channel 83 is changed. It should be noted that the air-supply tubular passage 26 and the water-supply tubular passage 27 are structured similarly to the foregoing arrangement. The way of the change is made similarly so that the portion corresponding to the warp-enabled portion of the cover-type endoscope is made to be the softest portion.

An insertion channel 84 shown in FIG. 20 has an arrangement that a multiplicity of grooves 84 are continuously formed on the outer surface of the tube, resulting in a soft structure.

An insertion channel 85 shown in FIG. 21 is so arranged as to have different flexibility by changing the wall-thickness of-the tube.

Since the hardness of the resin is not changed in this embodiment, the cover can be manufactured easily. The residual structures, operations and effects are the same as those of the third embodiment, and, therefore, their descriptions are omitted here.

The present invention is not limited to the channel-provided insert cover portion, but it can be adapted to a channel-less insert cover portion.

Figure 22:
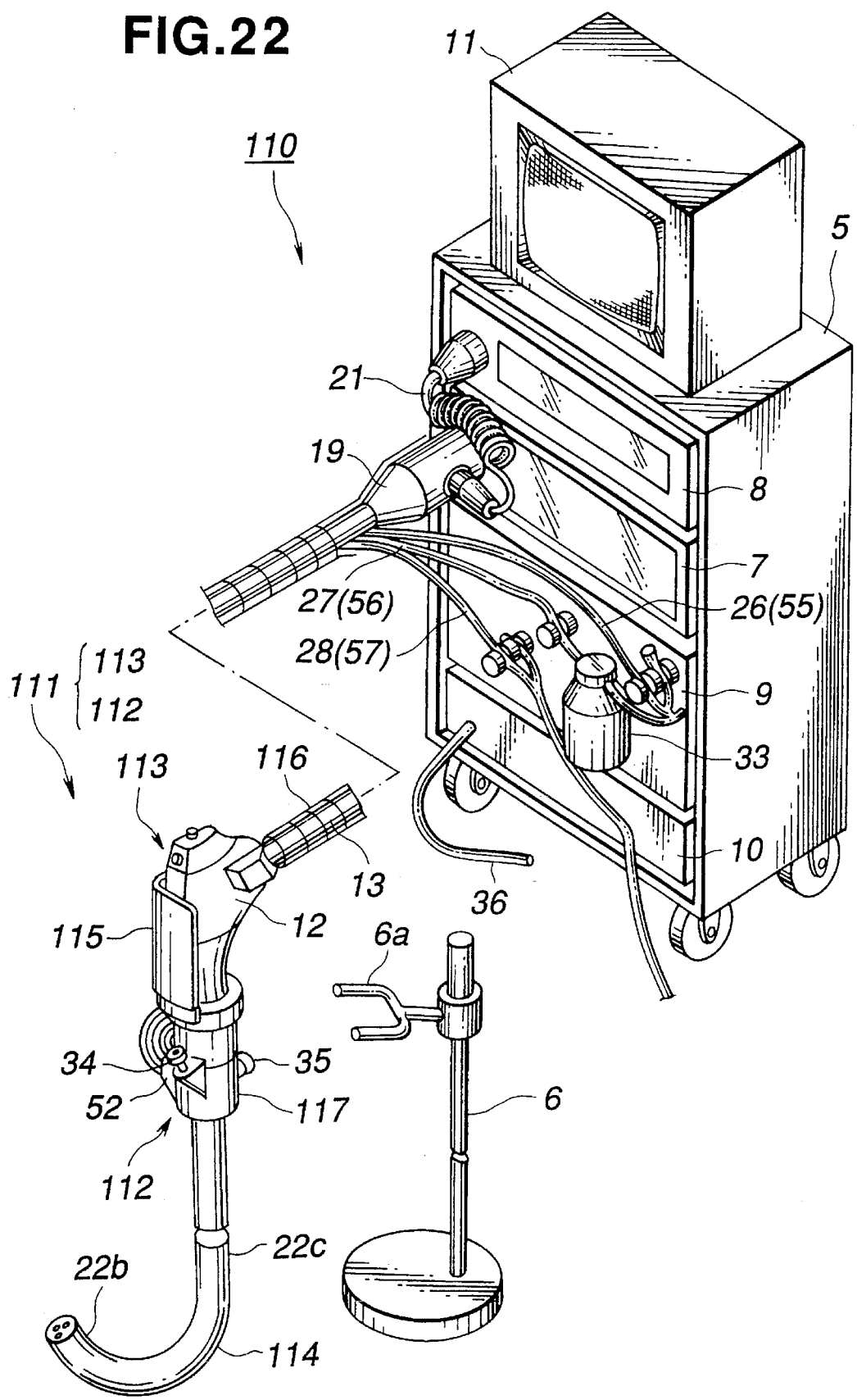
FIGS. 22 to 30 relate to a sixth embodiment of the present invention.
Figure 23:
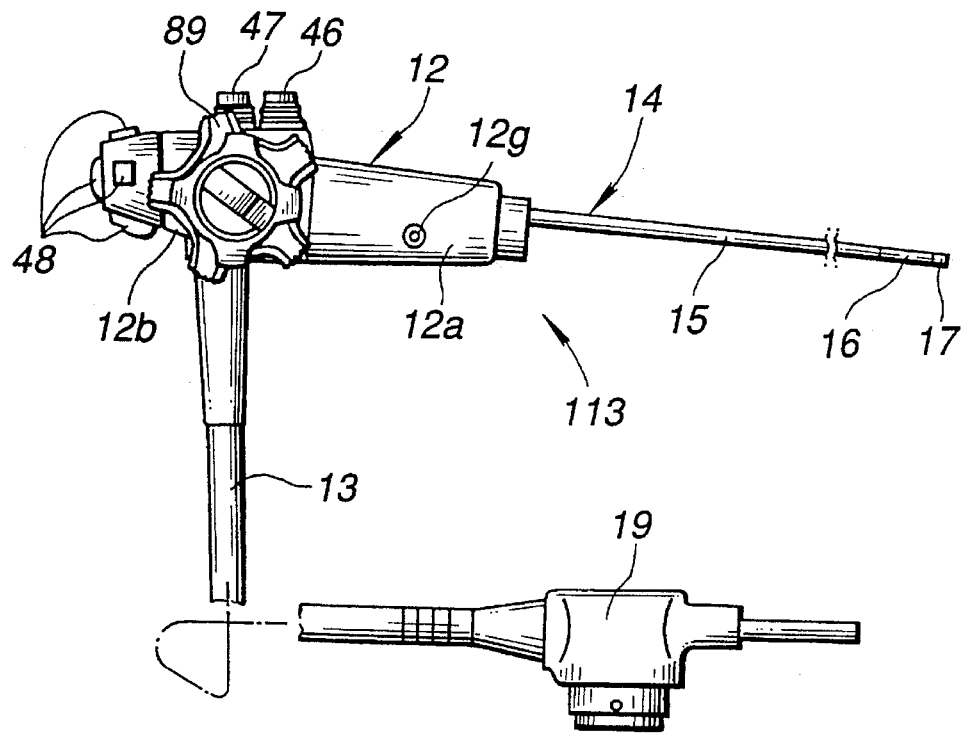
Figure 23:
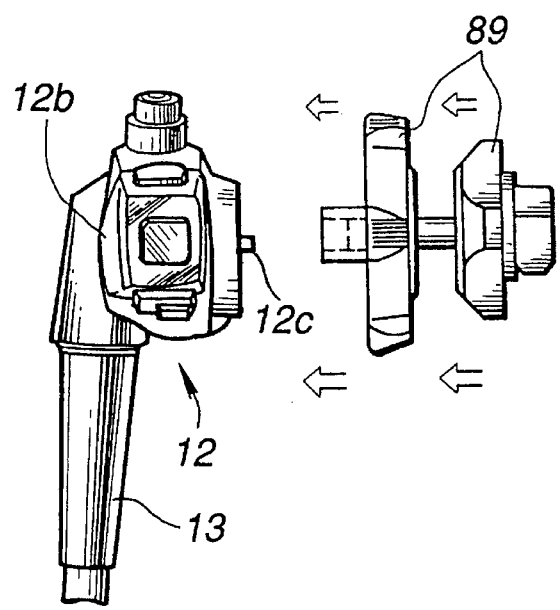
Figure 24:
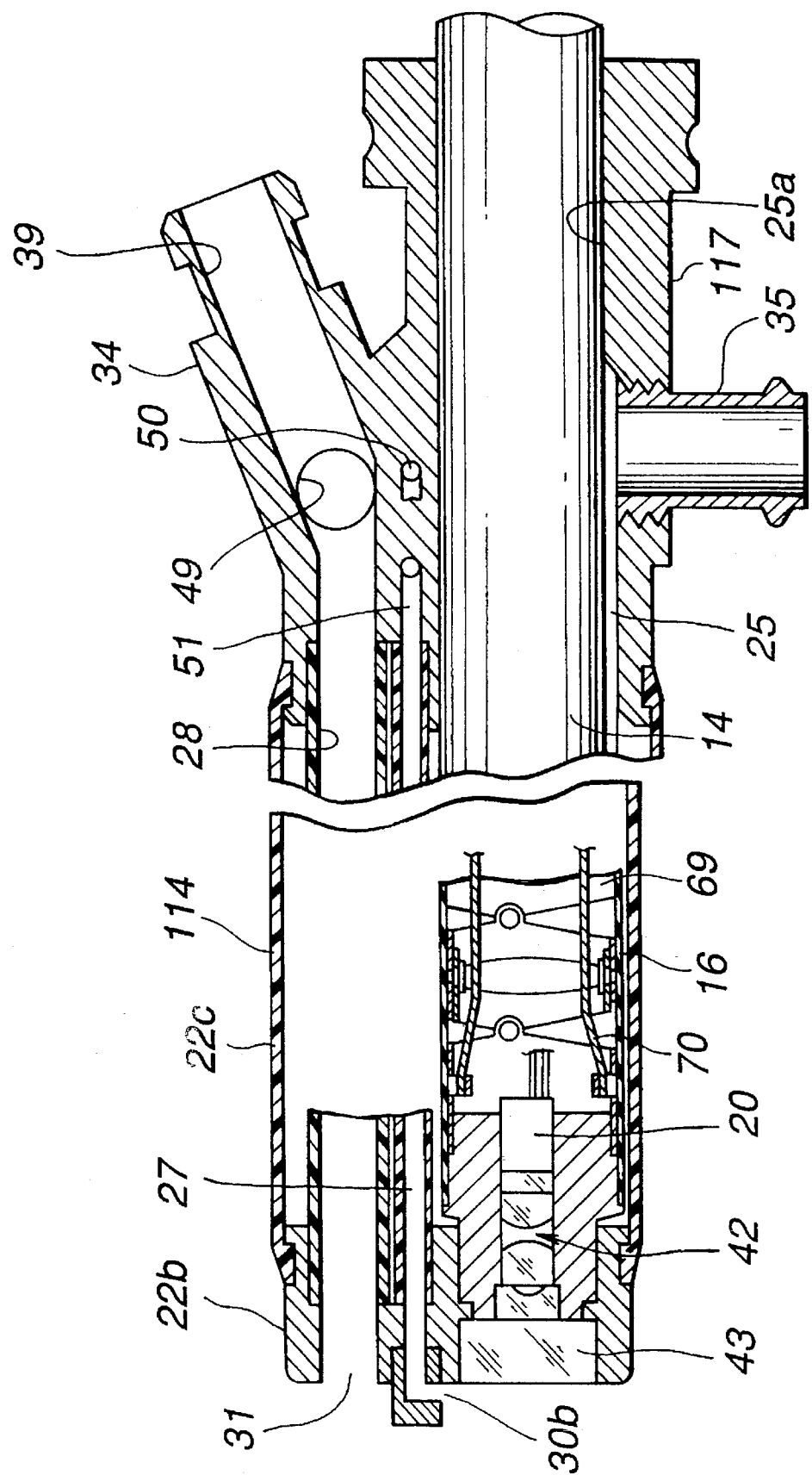
Figure 25:
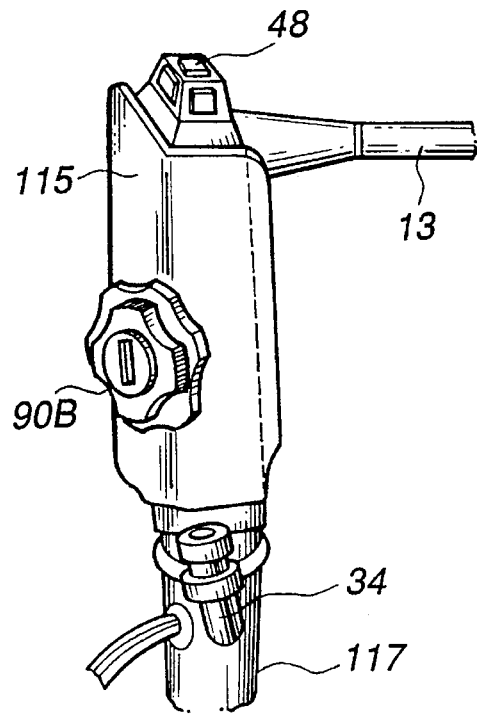
Figure 26:
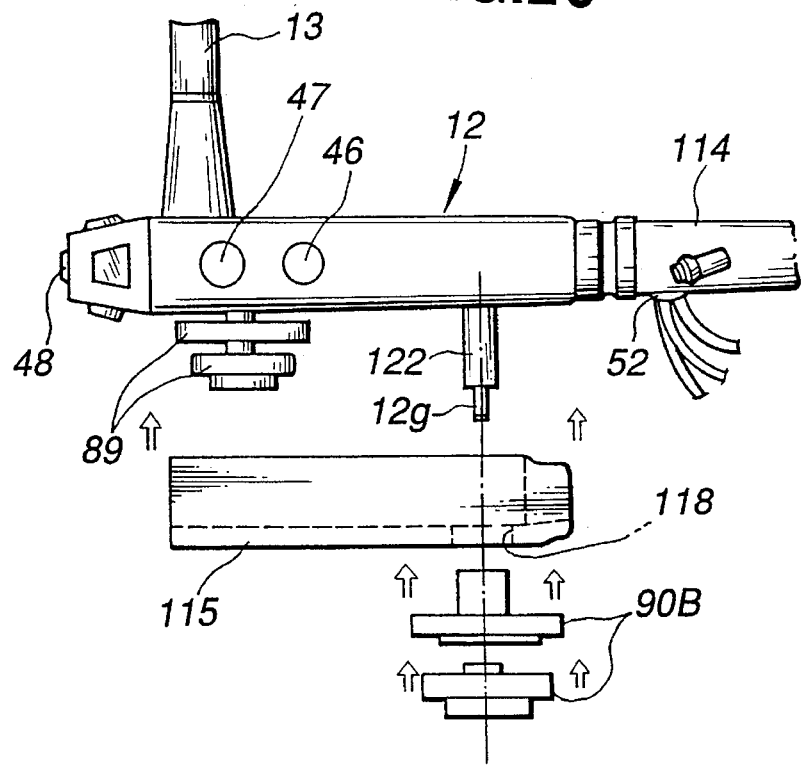
Figure 27:
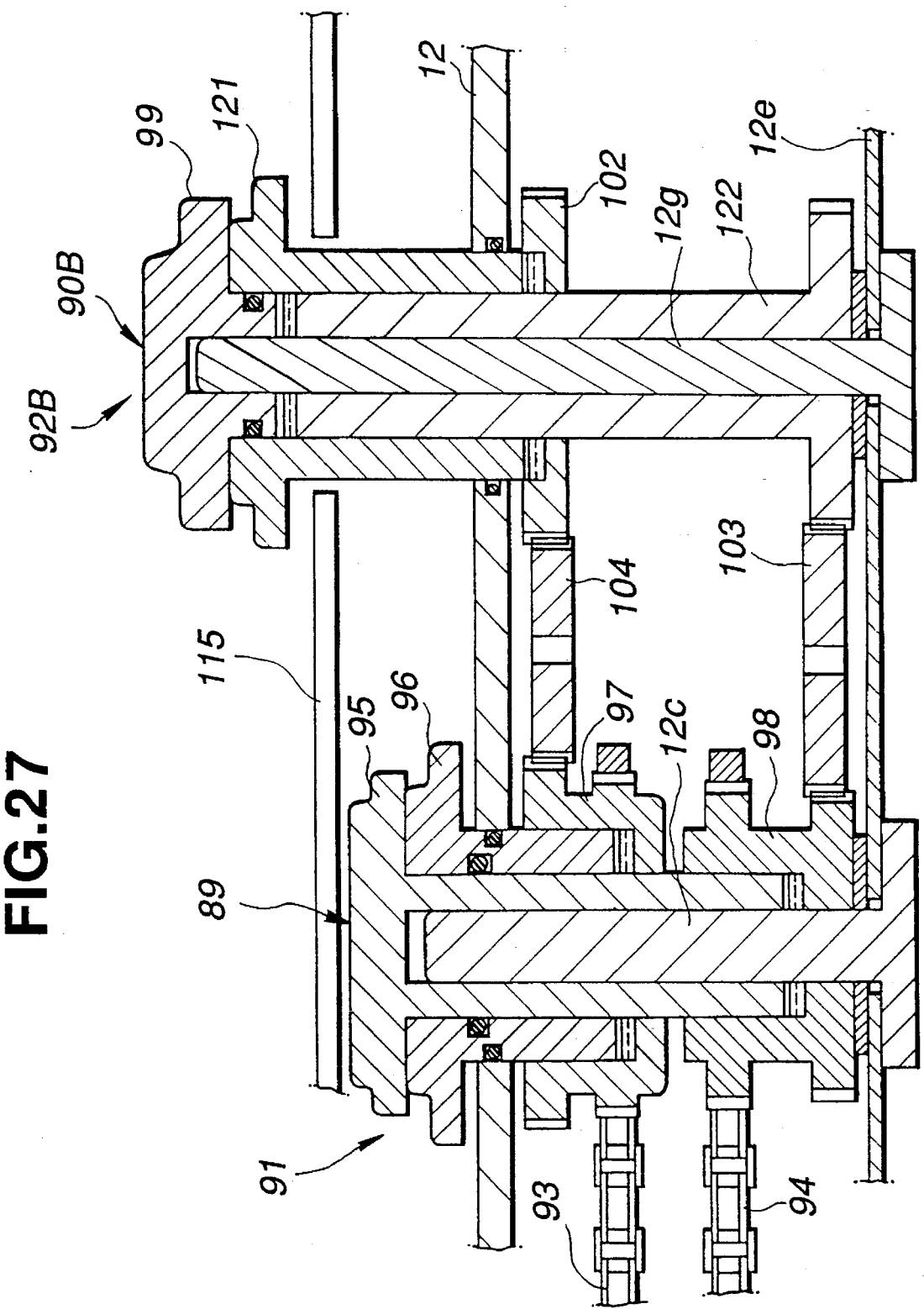
Figure 28:
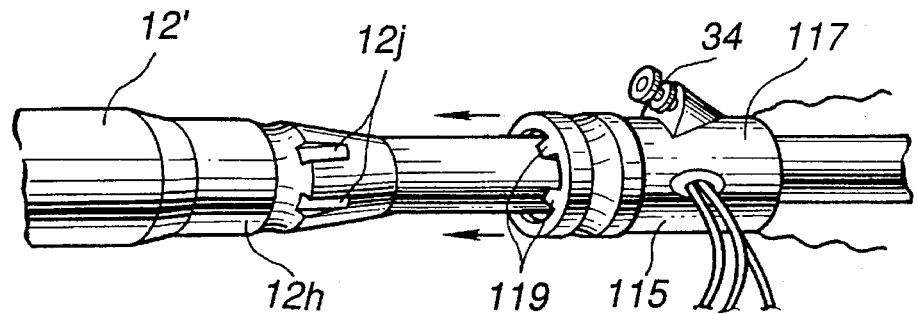
Figure 29:
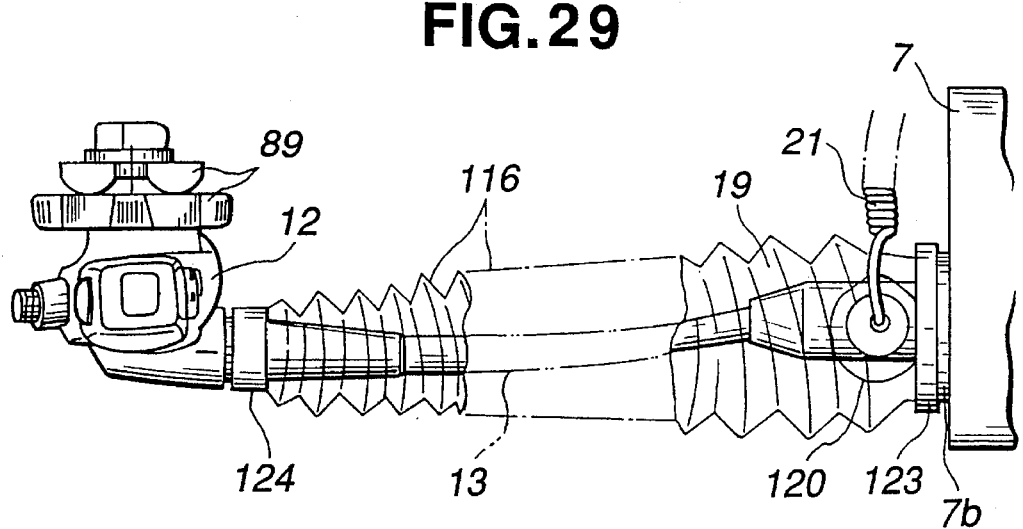
Figure 30:
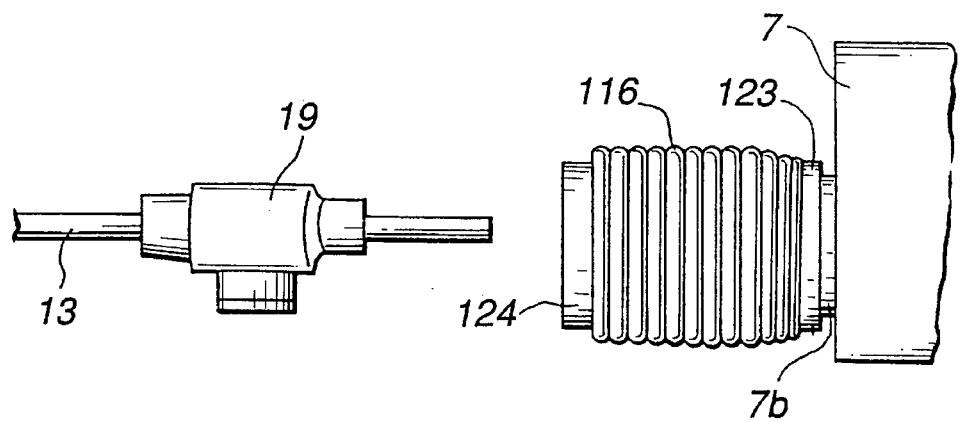

FIGS. 22 to 30 relate to a sixth embodiment of the present invention. FIG. 22 is an overall schematic view which illustrates an endoscope apparatus to which a cover-type endoscope is connected. FIG. 23(a) is a schematic view which illustrates the cover-type endoscope, and FIG. 23(b) is a view which illustrates installation of an angle knob. FIG. 24 is a side elevational cross sectional view which illustrates the leading portion of the cover-system endoscope. FIG. 25 is a structural view which illustrates the cover-type endoscope to which a control-unit cover is fastened. FIG. 26 illustrates installation of the control-unit cover portion and the angle knob. FIG. 27 is a cross sectional view which illustrates the structure of a warp-control mechanism. FIG. 28 is a structural view which illustrates a modification of the endoscope control unit and the insert cover portion. FIG. 29 illustrates installation of the universal cord cover portion. FIG. 30 is a side elevational view which illustrates a state where the universal cord cover portion is contracted.

An endoscope apparatus 110 shown in FIG. 22 is an apparatus to which an endoscope-cover-system endoscope (hereinafter abbreviated a "cover-type endoscope") 111 having channels can be attachably/detachably connected.

The cover-system endoscope 111 is constituted by combining an endoscope cover (hereinafter abbreviate to a "cover") 112 having channels and an endoscope-cover-type endoscope (hereinafter abbreviated to a "cover-type endoscope") 113 having channels. The cover-type endoscope 113 is an electronic-type endoscope.

As shown in FIG. 22, the cover 112 for covering the cover-type endoscope 113 is composed of an insert cover portion 114, a guard portion 115 serving as a shielding member, and a universal cord cover portion 116.

The cover 112 covers an insert 14 of the cover-type endoscope 113 shown in FIG. 23A to eliminate the necessity of cleaning and disinfecting the endoscope to be performed after an inspection has been completed.

The endoscope apparatus 110 comprises the cover-system endoscope 111, a cart 5 accommodating various peripheral devices to which the cover-system endoscope 111 is connected, and a cover holder 6 for holding the cover-system endoscope 111.

The cart 5 shown in FIG. 22 and accommodating the peripheral devices accommodates, for example, a light source apparatus 7, a video processor 8, a fluid control apparatus 9, and an expander (hereinafter abbreviated to an "expander") 10 for an endoscope cover having channels. The cart 5 holds a monitor 11 placed on the ceiling plate thereof.

The light source apparatus 7 supplies irradiation light to the cover-type endoscope 113 of the cover-system endoscope 111. The video processor 8 is connected to the electronic-type cover-type endoscope 113 to convert an electric signal supplied from the endoscope 113 into a standard video signal, followed by outputting the video signal to the monitor 11. The monitor 11 receives the video signal to display an image of the endoscope 113.

The fluid control apparatus 9 supplies air/water through tubular passages formed in the cover 112 and serving as channels to be described later. Therefore, the fluid control apparatus 9 has a water-supply source and an air-supply source (omitted from illustration). The tubular passages connected to the air-supply source and the water-supply source are controlled by electromagnetic valves to be opened/closed as desired.

The expander 10 supplies air into the insert cover portion 114 to expand it. As a result of the expansion, the cover-type endoscope 113 can easily be fastened to or removed from the insert cover portion 114.

As shown in FIG. 23(a), the cover-type endoscope 113 comprises a control unit 12, a universal cord 13 extending from the side portion of the control unit 12, and an insert 14 connected to the control unit 12. The insert 14 of the cover-type endoscope 113, as shown in FIG. 23(a), comprises a flexible tube portion 15, a warp-enabled portion 16 that can be warped, and a hard leading portion 17 when viewed from the base portion of the control unit 12 toward the leading portion.

The insert 14 of the cover-type endoscope 113 has a small diameter and has a D-shape cross sectional shape. The leading portion 17 of the cover-type endoscope 113 has irradiation optical system (omitted from illustration) and an object optical system 42 shown in FIG. 24. It should be noted that the insert 14 of the endoscope 113 may be formed into a cylindrical shape.

At the rear end of the irradiation optical system, light emission ends of light guide fibers (omitted from illustration) are disposed. The light guide fibers are allowed to pass through the insert 14, the control unit 12 and the universal cord 13.

The universal cord 13 has, at an end portion thereof, a connector 19. The connector 19 is attachably/detachably connected to a connector receptor 7*b* provided for the light source apparatus 7. As a result, irradiation light can be supplied from the light source apparatus 7 to the incidental ends of the light guide fibers.

As shown in FIG. 24, a solid-state image sensing device 20 for converting an incident optical image into an electric signal is disposed at the rear end of the objective optical system 42. The electric signal transmitted from the solid-state image sensing device 20 is received by the video processor 8 via a signal cord 21 extending from the side portion of the connector 19 shown in FIG. 22 and so forth.

The warp-enabled portion 16 of the cover-type endoscope 113 includes a plurality of warping blocks 69 combined rotatively. End portions of a pair of warp controlling wires 70 are connected to the leading block among the warping blocks 69, while the other end portions of the same are, in the portion adjacent to the control unit 12, fixed to a chain to be described later. Also another pair of warp controlling wires penetrate the warping blocks 69 to be fixed there while being deviated from each other at an angle of 90° in the circumferential direction. Thus, the warp-enabled portion 16 can be warped in the vertical direction and the lateral direction.

As shown in FIG. 23(*a*), the control unit 12 has a holding portion 12*a* at the base portion thereof. Furthermore, a control unit body 12*b* is connected to the upper portion of the holding portion 12*a*. The control unit body 12*b* of the control unit 12 has an air-supply/water-supply control switch 46, a suction control switch 47, and a function switch 48 for taking a photograph each disposed therein.

The control unit body 12*b* has, on the side surface thereof, an angle knob 89 for the left hand that is attachably/detachably fastened to a knob shaft 12*c* projecting over the body 12*b* as shown in FIG. 23(*b*).

The holding portion 12*a* has, on the side surface thereof, an angle knob 90B for the right hand that is attachably/detachably fastened to a knob shaft 12*g*. In particular, the angle knob 90B for the right hand is made of material, such as polysulfon or denatured PPO, that can be disinfected.

The control unit 12 has the guard portion 115 attachably/detachably fastened thereto. FIG. 26 illustrates a state where the guard portion 115 and the angle knob 25 for the right hand are fastened to the control unit 12.

The guard portion 115 is fastened to the control unit 12, followed by inserting the angle knob 90B into a hole 118 formed in the guard portion 115 so as to be fastened into the hole 118.

The guard portion 115 is fastened while covering the angle knob for the left hand, the air/water supply control switch 46 and the suction control switch 47. FIG. 25 illustrates a state where fastening of the guard portion 115 has been completed.

The cover holder 6 shown in FIG. 22 has an arm portion 6*a* that holds the insert cover portion 114 at the time of fastening the insert cover portion 114 to the cover-type endoscope 113. As a result, the endoscope 114 can sanitarily be held because the hand does not touch the cover 44. Furthermore, the operation can easily be performed.

FIG. 24 is a side elevational cross sectional view which illustrates a state where the cover-type endoscope 113 is inserted into the insert cover portion 114.

The insert cover portion 114 is used to isolate the insert 14 of the cover-type endoscope 113 from the external environment. The insert cover portion 114 is formed into an elongated shape, the insert cover portion 114 having a joint (hereinafter abbreviated to a "joint") 117 for fixing the control unit 12 of the endoscope 113, that is a unit adjacent to the operator, and a leading unit portion 22*b* that are made of hard material, for example, metal or resin.

The portion between the joint 117 of the insert cover portion 114 and the leading unit portion 22*b* is hermetically covered with an insert-cover coat 22*c* made of flexible material. The insert cover coat 22*c* is, at the leading portion thereof, connected to be received by an edge portion formed around the outer surface of the rear portion of the leading unit portion 22*b*. The insert cover coat 32*c* is similarly connected in a portion adjacent to the joint 117.

The insert-cover coat 22*c* is made of resin, such as polyurethane, that exhibits excellent chemical resistance and that is relatively flexible.

The insert cover portion 114 includes an endoscope insertion channel 25 into which the insert 14 can be inserted, and an air-supply tubular passage 26, a water-supply tubular passage 27 and a suction tubular passage 28 serving as channels.

The endoscope insertion channel 25 has, in the base portion thereof, an opening 25*a* for inserting the insert 14 in the joint 117. The opening 25*a* of the endoscope insertion channel 25 is arranged to receive the end portion of the insert 14 adjacent to the operator. It should be noted that the opening 25*a* may be arranged to receive the base portion of the endoscope control unit 12. The endoscope insertion channel 25 is closed in the leading unit portion 22*b* so that the insert 14 of the cover-type endoscope 113 can be hermetically isolated from the outer environment.

The air-supply tubular passage 26, the water-supply tubular passage 27 and the suction tubular passage 28 extend outwardly from the side portion of the joint 117, while their end portions are respectively closed.

The air-supply tubular passage 26, the water-supply tubular passage 27 and the suction tubular passage 28 have their intermediate portions respectively formed into a suction connection tube 49, an air-supply connection tube 50 and a water-supply connection tube 51. The suction connection tube 49, the air-supply connection tube 50 and the water-supply connection tube 51 are communicated with a tubular passage integrating connector 52 fastened to the side portion of the joint 117 shown in FIG. 22. The suction, air-supply and water-supply connection tubes 49, 50 and 51 respectively are communicated with a suction external tube 57, an air-supply external tube 55 and a water-supply external tube 56 via the tubular passage integrating connector 52. The external tubes 55, 56 and 57 are connected to the air supply source or the like as described above.

A curing tool insertion port 34 and an expansion tube joint 35 project over the side portion of the joint 117 as shown in FIG. 24. The expansion tube joint 35 includes the internal tubular passage that is connected to the endoscope insertion channel 25. An expansion tube 36 connected to the expander 10 is attachably/detachably connected to the expansion tube joint 35.

The curing tool insertion port 34 projects diagonally rearwards with respect to a direction of the longitudinal axis of the insert cover portion 114. The internal tubular passage of the curing tool insert port 34 is opened at the end portion thereof, while another end portion is connected to the suction tubular passage 28. That is, the suction tubular passage 28 also serves as a tubular passage for the curing tool channel at the leading portion thereof. Therefore, the opening 31 is an outlet port for the curing tool. Reference numeral 39 represents a tubular passage of the rear portion of the curing channel.

A modification of the structure of the control unit 12 will now be described.

FIG. 28 illustrates a structure which is partially different from the control unit 12 of the cover-type endoscope 113 shown in FIG. 23. FIG. 28 illustrates a state where the insert cover portion 114 is being fastened to the cover-type endoscope 113.

A control unit 12' of the cover-type endoscope 113 has a cut portion 12j in the longitudinal direction at a position corresponding to a cover fastening portion 12h in the base portion of the control unit 12'.

The joint 117 of the insert cover portion 114 has a projection 119 on the inner surface thereof. The cut portion 12j and the projection 119 have the shapes so that they can be engaged to each other. The number, the position and the size are variably prepared to correspond to the type of the endoscope.

A universal cord cover 116 Will now be described.

FIG. 29 illustrates a state where the universal-cord cover 116 is fastened to the cord 13 of the cover-type endoscope. FIG. 30 illustrates a state where the connector 19 has been removed from the light source apparatus 7 and the universal cord cover 116 has been removed from the cord 13.

The universal-cord cover 116 is formed into, for example, a contractive bellows shape. The universal-cord cover portion 116 has an end portion that is attachably/detachably fastened to the connector receptor 7b of the light source apparatus 7.

A joint 123 formed in an end portion of the universal-cord cover portion 116 adjacent to the light source is fastened to the connector receptor 7b of the light source apparatus 7. The connector 19 is fastened to the connector receptor 7b over the cord cover portion 116. The joint 123 formed in an end portion of the cord cover portion 116 adjacent to the light source is fastened to the connector receptor 7b of the light source apparatus 7.

The universal-cord cover portion 116 has a joint 124 disposed at an end portion thereof adjacent to the endoscope, the joint 124 being attachably/detachably fastened to a cord connection portion 13 of the cover-type endoscope 113. The signal cable 21 is fastened to the connector 19 via a side hole 120 formed in the universal-cord cover portion 116.

The structure of a warp control mechanism will now be described.

FIG. 27 illustrates a cross section of a control unit including the angle knob 89 for the left hand, the angle knob 90B for the right hand and their peripheral portion.

The warp control mechanism according to this embodiment comprises a warp control mechanism 91 for the left hand and a warp control mechanism 92B for the right hand as shown in FIG. 26.

The warp control mechanism 91 for the left hand and the warp control mechanism 92B for the right hand respectively include the angle knob 89 for the left hand and the angle knob 90B for the right hand. As a result, the warp-enabled portion 16 is warped upwards (hereinafter called "U"), downwards (hereinafter called "D")/rightwards (hereinafter called "R") and leftwards (hereinafter called "L").

The warp control mechanism 91 for the left hand and the warp control mechanism 92B for the right hand are operated synchronously via two gears to be described later. Furthermore, the warping blocks 69 are rotated vertically or laterally when a UD chain 93 or a RL chain 94 is moved forwards/rearwards.

The end portions of the warp control wires 70 are connected to the two end portions of the UD chain 93 to warp the warp-enabled portion 16 in the UD direction.

The end portions of the warp control wires (omitted from illustration) are connected to the two end portions of the RL chain 94 to warp the warp-enabled portion 16 in the RL direction.

The knob shaft 12d for the left hand and the knob shaft 12g for the right hand are, while keeping a distance, fastened to an internal plate 12e disposed in the control unit 12. The head portions of the knob shaft 12d for the left hand and the knob shaft 12g for the right hand respectively project over the outer wall of the control unit 12. Furthermore, holes are formed around the knob shaft 12d for the left hand and the knob shaft 12g for the right hand, the holes being formed in the outer wall of the control unit 12 to allow the angle knobs 89 and 90B to pass through.

The knob shaft 12g for the right hand has a length to project over the hole 118 formed in the guard portion 115 in a state where the guard portion 115 is fastened to the endoscope 113.

The angle knob 89 for the left hand has a RL knob 95 for the left hand and having a projecting fastening portion to be fastened to the knob shaft 12d for the left hand and a UD knob 96 for the left hand to be fastened around the fastening portion of the RL knob 95 for the left hand.

The RL knob 95 for the left hand and the UD knob 96 for the left hand respectively are engaged to a RL gear 98 for the left hand and a UD gear 97 for the left hand by gears. Furthermore, the RL gear 98 for the left hand and the UD gear for the left hand respectively are fastened to the RL chain 94 and the UD chain 93 attachably/detachably and rotatively.

Therefore, when the RL knob 95 for the left hand is rotated, the RL chain 94 is rotated. When the UD knob 96 for the left hand is rotated, the UD chain 93 is rotated.

Also the warp control mechanism 92B for the right hand is structured substantially similarly to the mechanism 91 for the left hand. The angle knob 90B for the right hand has a RL knob 99 for the right hand and having a projecting fastening portion to be fastened to the knob shaft 12g for the right hand and a UD knob 121 for the right hand to be fastened around the fastening portion of the RL knob 99 for the right hand.

The RL knob 99 for the right hand and the UD knob 121 for the right hand are respectively engaged to the RL gear 122 for the right hand and the UD ger 102 for the right hand by the gears.

The RL gear 98 for the left hand and the RL gear 122 for the right hand respectively are engaged to the RL gear 103 to be synchronously rotated.

The UD gear 97 for the left hand and the UD gear 102 for the right hand respectively are engaged to the UD gear 104 to be synchronously rotated.

In synchronization with the rotations of the RL knob 99 for the right hand and the UD knob 121 for the right hand, the RL chain 94 and the UD chain 93 are rotated, respectively.

The angle knob 89 for the left hand has the RL knob 95 for the left hand and having a projecting fastening portion to be fastened to the knob shaft 12d for the left hand and the UD knob 96 for the left hand to be fastened around the fastening portion of the RL knob 95 for the left hand.

When the angle making operation is performed with the foregoing structure, disinfected gloves are used to perform the warping operation with the angle knob 90B for the right hand. The left hand holds the control unit 12 under the guard portion 115 to operate the angle knob 90B for the left hand, the air-supply/water-supply switch 46 and the suction control switch 47 and the like under the guard portion 115.

A new universal-cord cover portion 116 disinfected, or cleaned is previously fastened to the light source apparatus 7 while being contracted. Then, the connector 19 is allowed to pass through the universal-cord cover portion 116, followed by fastening the joint 123 adjacent to the light source to the connector receptor 7b of the light source apparatus 7. Then, the universal-cord cover portion 116 is extended to fasten the joint 124 adjacent to the endoscope to the cover-type endoscope 113. The signal cable 21 is fastened by making side hole 120 of the universal cord 13 to be received by the connector 19. Therefore, the direct touch of the universal cord 13 can be prevented during use.

Since the universal-cord cover portion is not easily contaminated, it is wasteful to exchange a new one at each operation. The foregoing universal-cord cover portion 116 can be repeatedly attached/detached while preventing occurrence of damage. Therefore, it is economical.

The left hand is used to hold the control unit 12, that is the unclean area, to rotate the RL knob 95 for the left hand and the UD knob 96 for the left hand to perform the warping operation.

The RL knob 95 for the left hand transmits the rotational force to the RL gear 98 for the left hand, resulting in the RL chain 94 is pushed/pulled. The wire (omitted from illustration) is pulled by the RL chain 94, the traction causing the warping blocks 69 connected to the other end portions of the wire to be warped rightwards/leftwards. That is, the warp-enabled portion 16 is warped laterally.

When the UD knob 96 for the left hand is rotated, the rotation force is similarly transmitted to the UD gear 97 for the left hand, the UD chain 93 and the wires 70. In accordance with the direction of the rotation operation, the warp-enabled portion 16 is vertically warped.

Since the right hand holds the insert cover portion 114 and the like that are the clean areas, the angle knob 90B for the right hand is used when the clean hand is used to perform the warping operation. When the RL knob 99 for the right hand is rotated by the right hand, the RL gear 122 for the right hand is rotated, causing the RL gear 103 to be rotated in a direction opposing the direction of the rotation of the RL gear 122 for the right hand. Furthermore, the RL gear 98 for the left hand is rotated in the same direction of the rotation of the RL gear 122 for the right hand. The foregoing rotations cause the RL chain 94 to be pulled, resulting in the warp-enabled portion 16 to be warped laterally.

The clean right hand rotates the UD knob 121 for the right hand, the rotational force being transmitted to the UD gear 102 for the right hand, the UD gear 104 and the UD gear for the left hand in this sequential order. As a result, the warp-enabled portion 16 is warped vertically.

In the case where, for example, the UD knob 96 for the right hand of the foregoing structure is rotated to downwards warp the warp-enabled portion 16, the rightward rotation of the UD knob 121 for the right hand causes the warp-enabled portion 16 to be warped downwards similarly.

Similarly, the rotation of the RL knob 95 for the left hand in the same direction of the rotation of the RL knob 99 for the right hand causes the warp-enabled portion 16 to perform the similar operation.

That is, the lateral/vertical warping operation is performed in such a manner that the warp-enabled portion 16 is warped in the same warping direction if the angle knob 89 for the left hand and the angle knob 90B for the right hand are rotated in the same direction.

The angle knob 90B for the right hand may be used repeatedly or may be made disposable. If the angle knob 90B for the right hand is made disposable, it must be made a medical waste.

According to this embodiment, the unclean left hand does not hold the angle knob 90B for the right hand, resulting in protection of the clean right hand from contamination occurring via the foregoing knob.

According to this embodiment, the angle knob 90B for the right hand and the angle knob 89 for the left hand are arranged to be operated in the same direction and causing the same warping direction to be realized. Therefore, the operator is able to operate them without inconvenience regardless of the hand that holds the foregoing knobs.

Furthermore, the arrangement of this embodiment that the guard portion 115 covers the unclean area when the right hand is used to perform the operation prevents the touch of the right hand with the unclean control unit 12 at the time of making the angle or inserting/drawing a curing tool such as the forceps. Therefore, this embodiment is able to prevent the contamination of the right hand, that holds the insertion portion or the curing tool such as the forceps.

As described above, the touch of the control unit, which is the unclean area, can be prevented without special attention paid by the operator. Therefore, the operator is able to be intent on the desired operation or cure while preventing the contamination of the hand that must be kept clean. That is, the arrangement according to this embodiment exhibits excellent operation facility. Furthermore, this embodiment is able to prevent the touch of the hand, that holds the control unit to be used in the contaminated area, with the angle knob 90B.

Moreover, this embodiment has the arrangement that the universal-cord cover portion 116, which is not frequently contaminated, can be made to belong the light source apparatus 7 to be used again and exchanged. Therefore, it is economical.

The structure shown in FIG. 28 has the arrangement that the insert-cover portion adaptable to the type of the selected cover-type endoscope is used for the cover-type endoscope in such a manner that the joint 117 is assuredly fastened to the cover-type endoscope 113 to align the cut portion 12j with the projection 119. According to this structure, an erroneous assembly, that the cover-type endoscope and non-adaptable type cover are combined, can be prevented.

Figure 31:
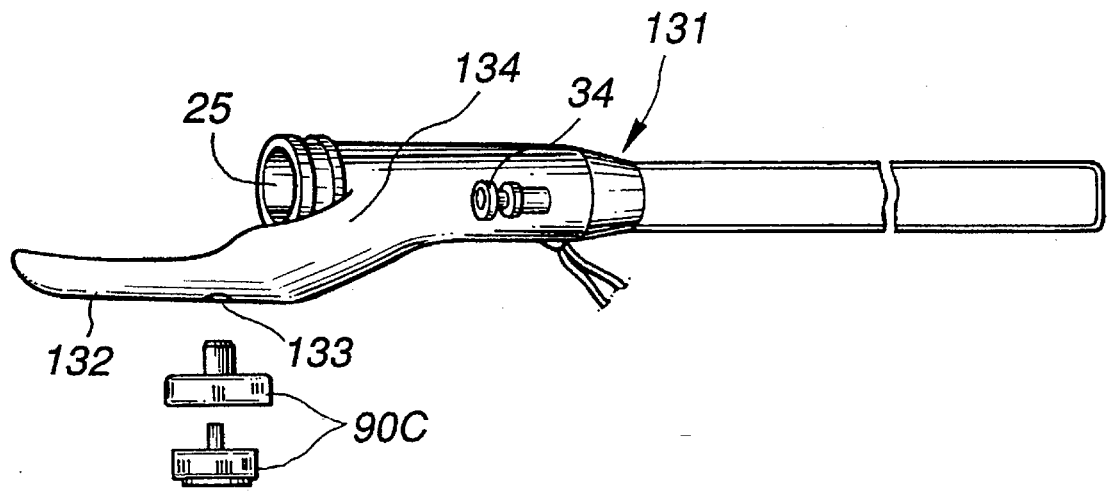
FIGS. 31 to 35 relate to a seventh embodiment of the present invention.
Figure 32:
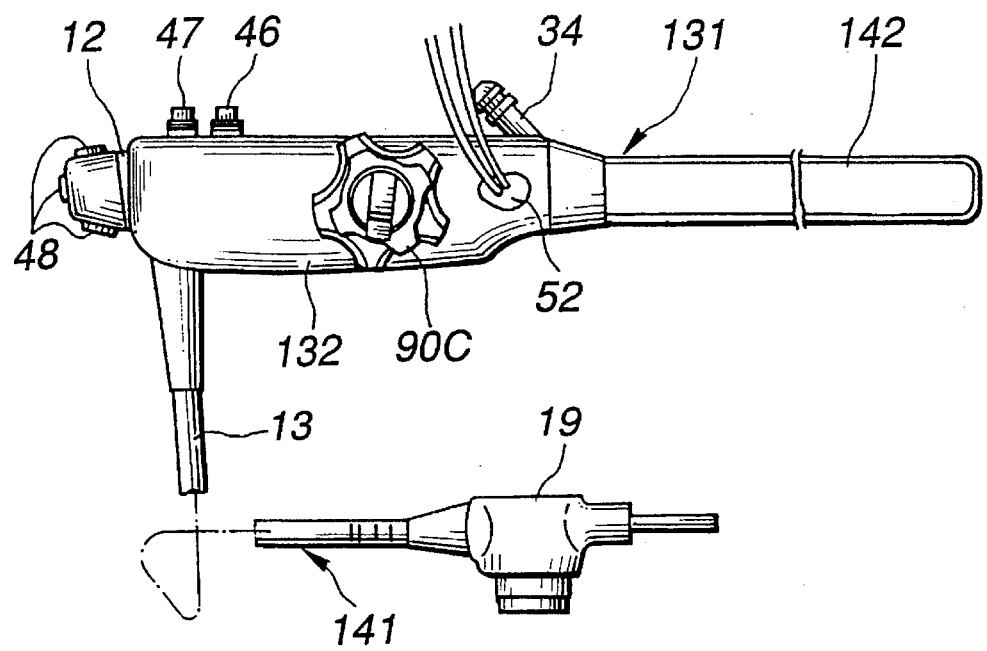
Figure 33:
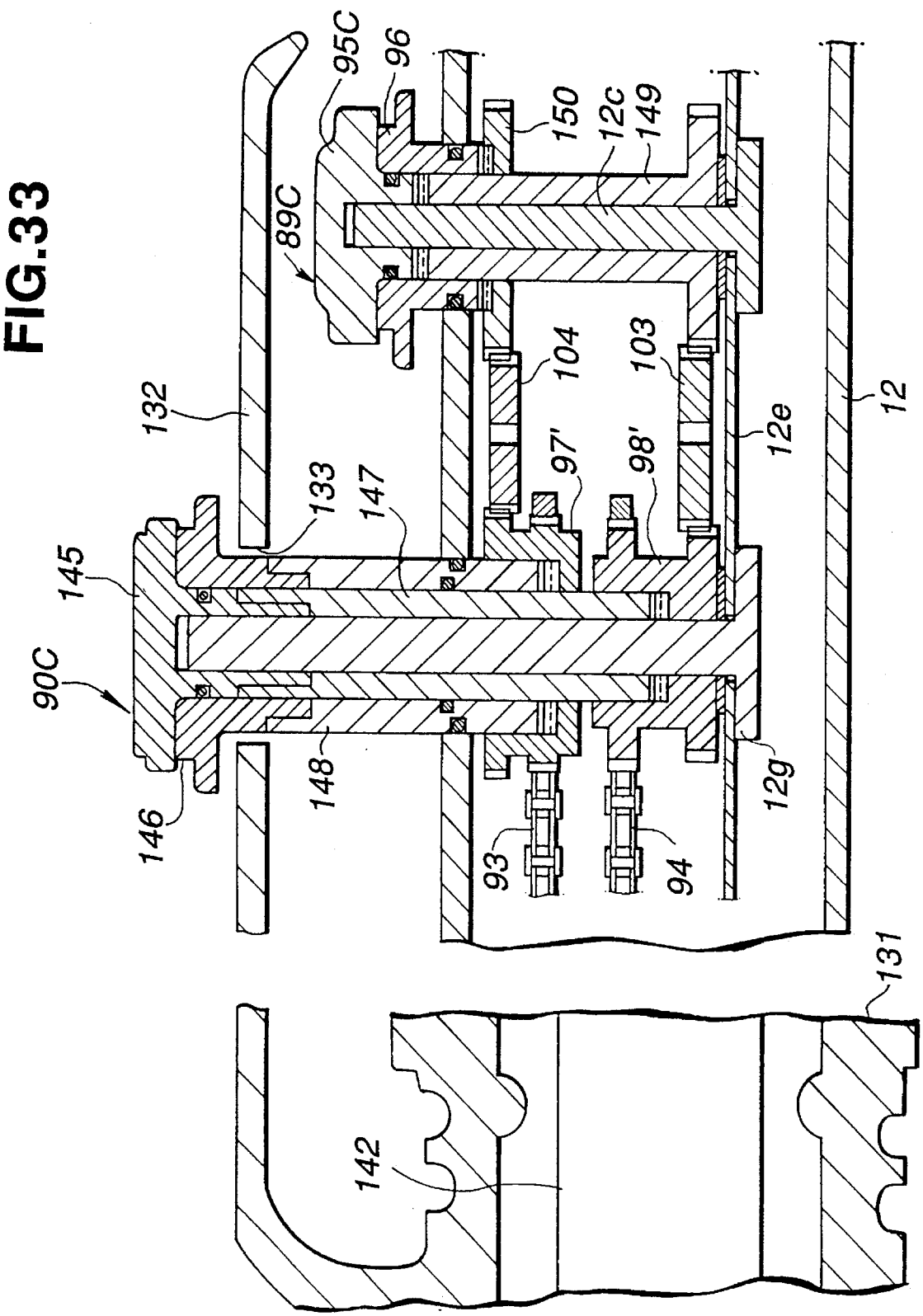
Figure 34:
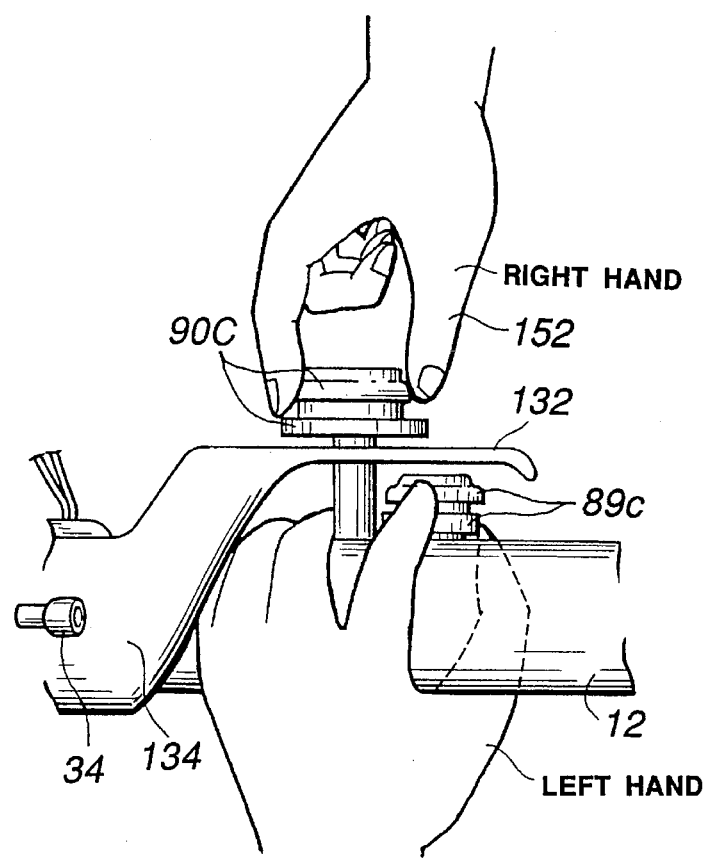
Figure 35:
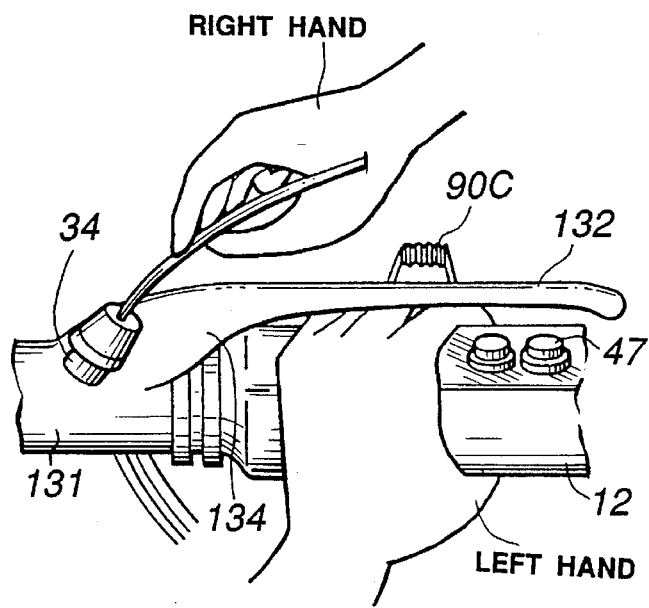

FIGS. 31 to 35 relate to a seventh embodiment of the present invention. FIG. 31 is a schematic view which illustrates an insert cover portion. FIG. 32 is a schematic view which illustrates a cover-system endoscope. FIG. 33 is a cross sectional view which illustrates the structure of a warp control mechanism. FIG. 34 illustrates the operation of the angle knob. FIG. 35 illustrates the action of the guard portion at the time of inserting/drawing a curing tool.

Although the sixth embodiment has the insulating member that is formed individually, the insert cover portion according to the seventh embodiment has an insulating means formed integrally. The same structures and the operations as those according to the sixth embodiment are given the same reference numerals, and their descriptions are omitted here. The description will be made about only the different portions.

An insert cover portion 131 shown in FIG. 31 covers an insert 142 of a cover-type endoscope 141 shown in FIG. 32. The disinfected insert cover portion 131 must be used at the time of an inspection.

The insert cover portion 131 has a guard portion 132 serving as an insulating means and projecting rearwards toward the operator. The guard portion 132 is disposed to cover the surface of the cover-type endoscope 141 to which the angle knob 90C is fastened. The guard portion 132 has a knob insertion hole 133 through which the disinfected angle knob 90C for the right hand pass.

The guard portion 132 has a forceps insertion guard portion 134 having, in at least a portion thereof, an L-shape formed from a position adjacent to the curing tool insertion port 34 toward the end portion adjacent to the operator.

The guard portion 132 may be individually formed from the insert cover portion 131.

FIG. 32 illustrates the shape realized when the insert cover portion 131 is fastened to the cover-type endoscope 141.

After the foregoing state of fastening has been realized, the guard portion 132 of the insert cover portion 131 is disposed between the angle knob 90C for the right hand and the control unit 12. The angle knob 90C for the right hand is allowed to pass through the knob insertion hole 133 and is attachably/detachably fastened to the knob shaft 12g.

FIG. 33 is a cross sectional view which illustrates a warp control mechanism including the guard portion 132 of the insert cover portion 131 and disposed in the control unit 12.

In contrast with the sixth embodiment having the arrangement that the warp control mechanism for the left hand is disposed in the leading portion, the seventh embodiment includes the warp control mechanism for the right hand that is disposed in the leading portion. The residual operations and effects are the same as those of the sixth embodiment. The same structures are given the same reference numerals, and the descriptions will be made about only the different structures.

The angle knob 90C for the right hand comprises a RL knob 145 for the right hand to which a RL shaft 147 is fastened and secured, and a UD knob 146 for the right hand to which a UD shaft 14 is fastened and secured. The RL knob 145 for the right hand and the UD knob 146 for the right hand are inserted into the insertion hole 133 formed in the guard portion 132 to be fastened.

The RL shaft 147 of the RL knob 145 for the right hand and the UD shaft 148 of the UD knob 146 for the right hand respectively are attachably/detachably engaged to a UD gear 97' for the right hand and a RL gear 98' for the right hand by, for example, a cam or a gear.

The UD gear 97' for the right hand and the RL gear 98' for the right hand respectively are attachably/detachably and rotatively fastened to the RL chain 94 and the UD chain 93.

The angle knob 98C for the left hand is engaged to the knob shaft 12c for the left hand. The angle knob 89C for the left hand has the RL knob 95C for the left hand to be engaged to the RL gear 149 for the left hand and the UD knob 96 for the left hand to be engaged to the UD gear 150 for the left hand.

The UD gear 150 for the left hand and the UD gear 97' for the right hand respectively are engaged to the tooth of the UD gear 104 to be synchronously rotated. The RL gear 149 for the left hand and the RL gear 98' for the right hand respectively are engaged to the tooth of the RL gear 103 to be synchronously rotated.

FIG. 34 illustrates a state where the angle operation is performed. FIG. 35 illustrates a state where a forceps 151 is being inserted or drawn from a forceps channel (omitted from illustration) by the right hand.

In the foregoing structure, when the RL knob 145 for the right hand and the UD knob 146 for the right hand are rotated by the right hand wearing a disinfected glove 152, rotational force is transmitted to the RL shaft 147 and the UD shaft 148. Furthermore, the rotational force is transmitted to the RL gear 98' for the right hand and the UD gear 97' for the right hand. As a result, the warp-enabled portion can be warped.

The contaminated left hand is used to hold the holding portion 12a of the control unit 12 to operate the angle knob 89 for the left hand. The clean right hand is used to operate the angle knob 90C for the right hand and is guarded by the guard portion 132 so that the touch of the right hand with the unclean control unit 12 is prevented.

At the time of inserting the forceps into the forceps channel through the curing tool insertion port 34, the touch of the clean right hand which is being used with the unclean control unit 12 is prevented by guarding the right hand with the forceps insertion guard portion 134.

According to this embodiment, the touch of the right hand, that holds the insert or the forceps, with the control unit which is the contaminated area can be prevented, and accordingly, cleanness can be kept. According to this embodiment, the touch of the hand, that holds the control unit for use in the contaminated area, with the curing tool insertion port, which is the clean area, and the curing tool can be prevented. The residual structures, operations and effects are the same as those according to the sixth embodiment, and therefore their descriptions are omitted here.

The structure may be arranged in such a manner that only the angle knob 89C is employed in place of the foregoing two angle knobs.

Figure 36:
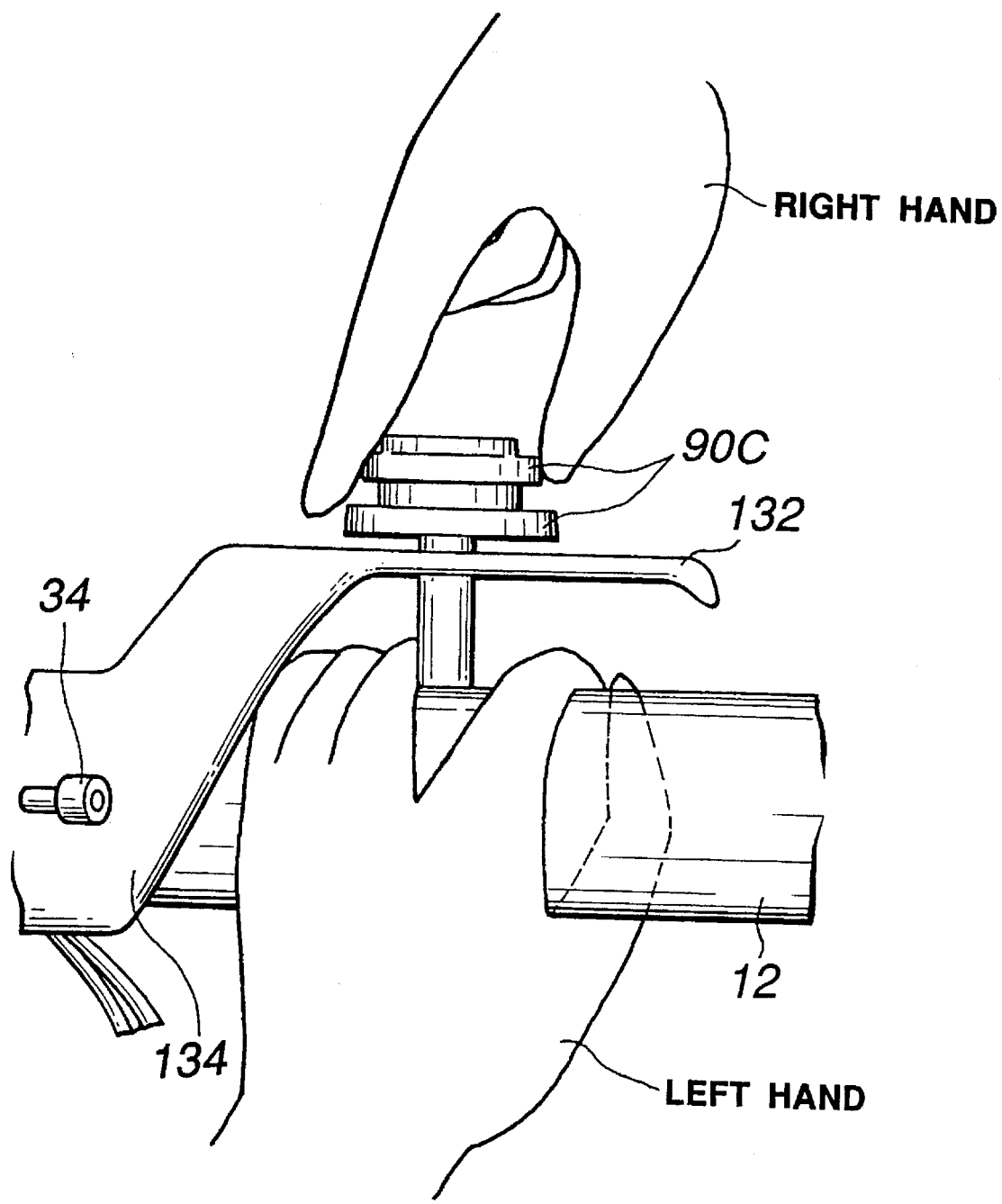
FIG. 36 illustrates the structure and a warping operation of the control unit according to an eighth embodiment.

FIG. 36 relates to an eighth embodiment and illustrates the operation of an endoscope to which an insert cover portion is fastened.

In this embodiment, the warp-enabled portion is warped by only the right hand. FIG. 36 illustrates a state where the warping operation is performed while fastening the insert cover portion 131 to the control unit 12.

The angle knob provided for the control unit 12 is only the angle knob 90C for the right hand. The angle knob 90C for the right hand is, similarly to the seventh embodiment, is allowed to pass through the insertion hole 133 formed in the guard portion 132 for the right hand.

Since the residual structures, operations and effects are the same as those according to the seventh embodiment, their descriptions are omitted here.

Although each of the foregoing embodiments is arranged in such manner that the insert is usually operated by the right hand and the control unit is also usually held by the left hand, the present invention is not limited to this. A similar structure can be constituted having an arrangement that the insert is handled with the left hand and the control unit is held by the right hand.

The cover-type endoscope according to the present invention is not limited to the foregoing electronic type endoscope. It may be an optical-type endoscope or an ultrasonic-type endoscope or the like without any particular limitation. The cover to be fastened to the cover-type endoscope according to the present invention is not limited to the cover having channels. A channel-less cover may be employed.

Figure 37:
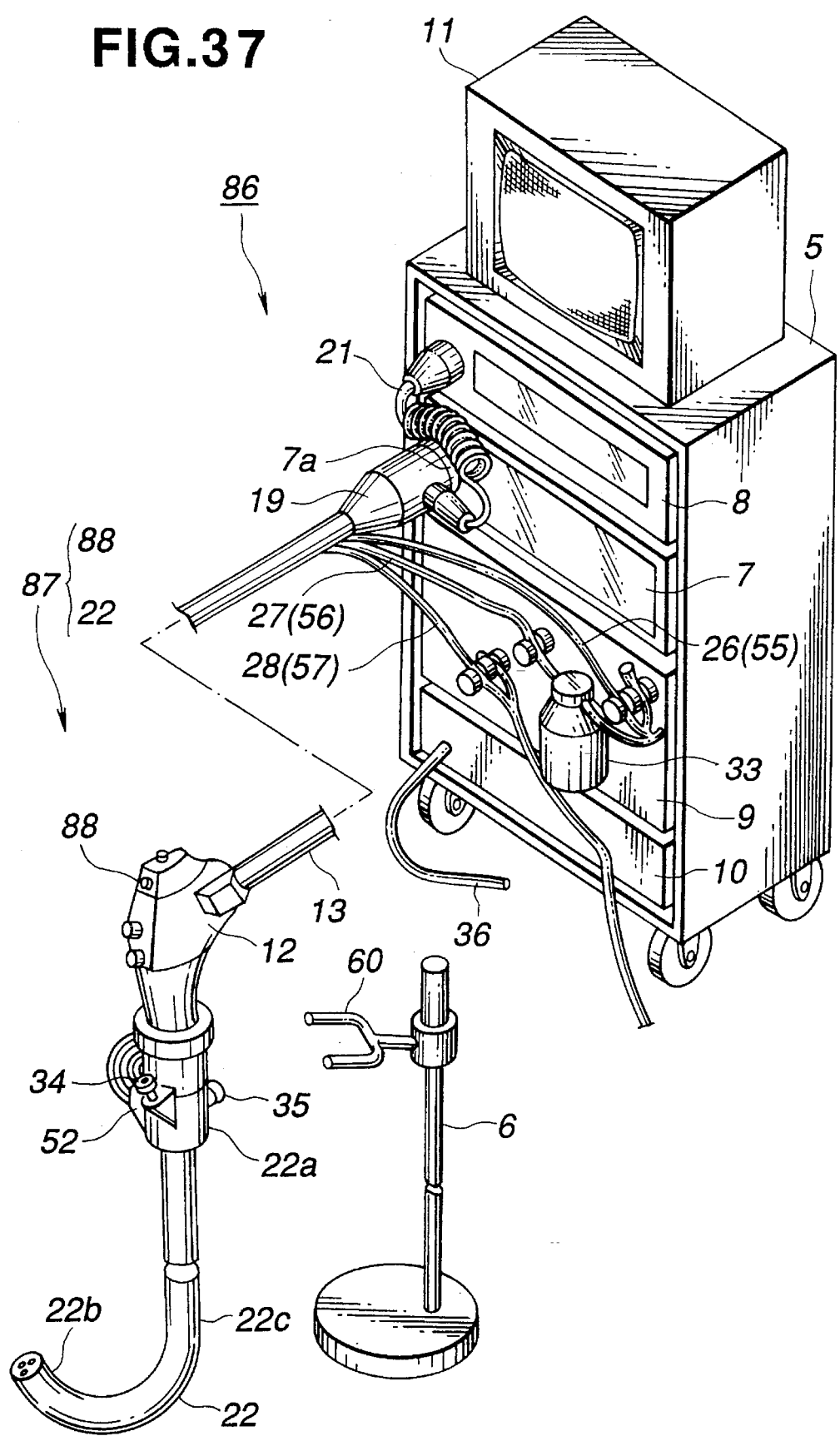
FIGS. 37 to 41 relate to a ninth embodiment of the present invention.
Figure 38:
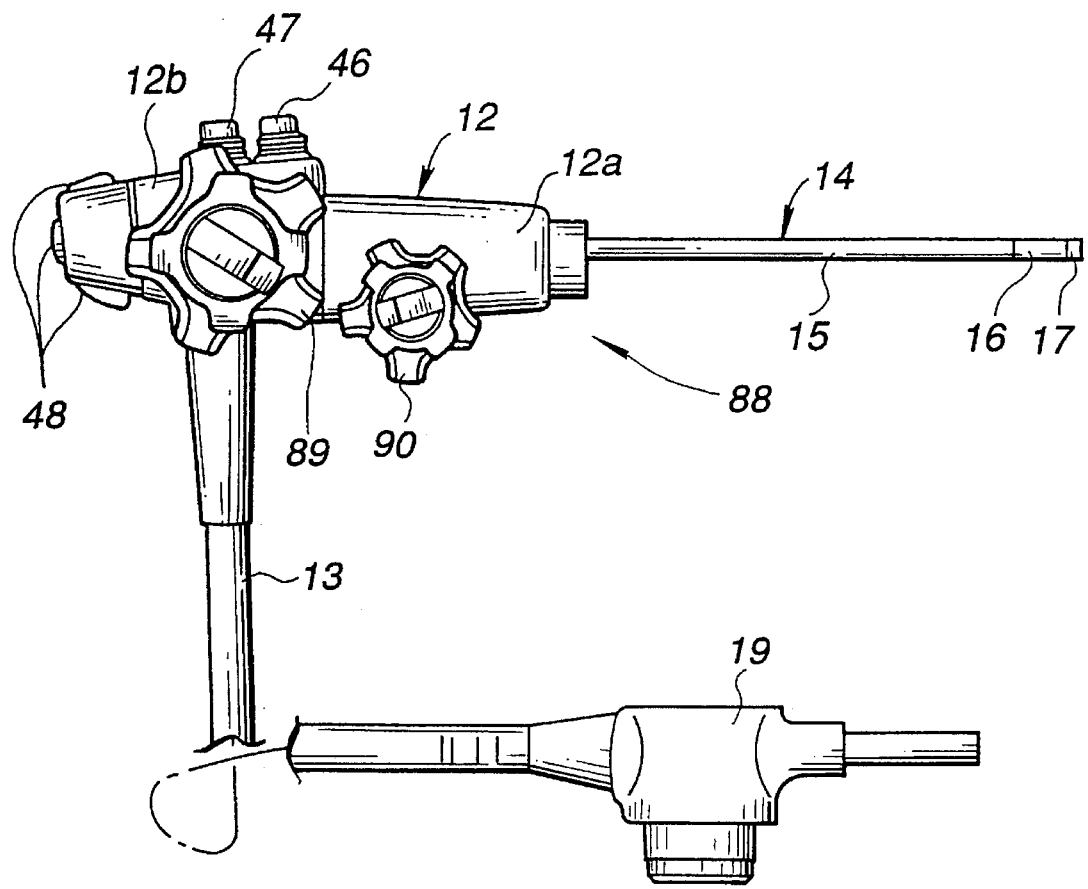
Figure 39:
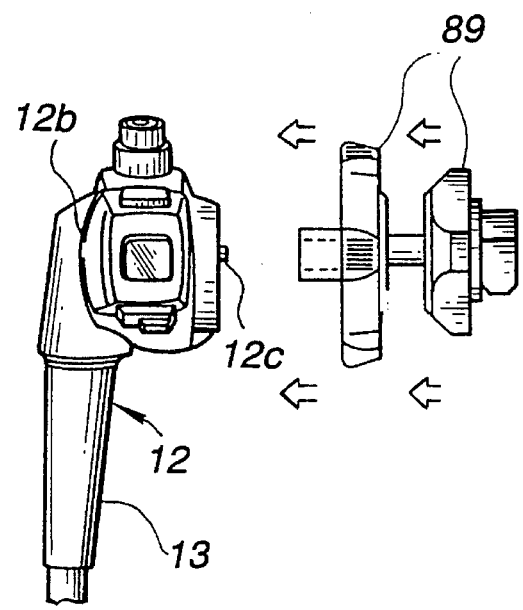
Figure 40:
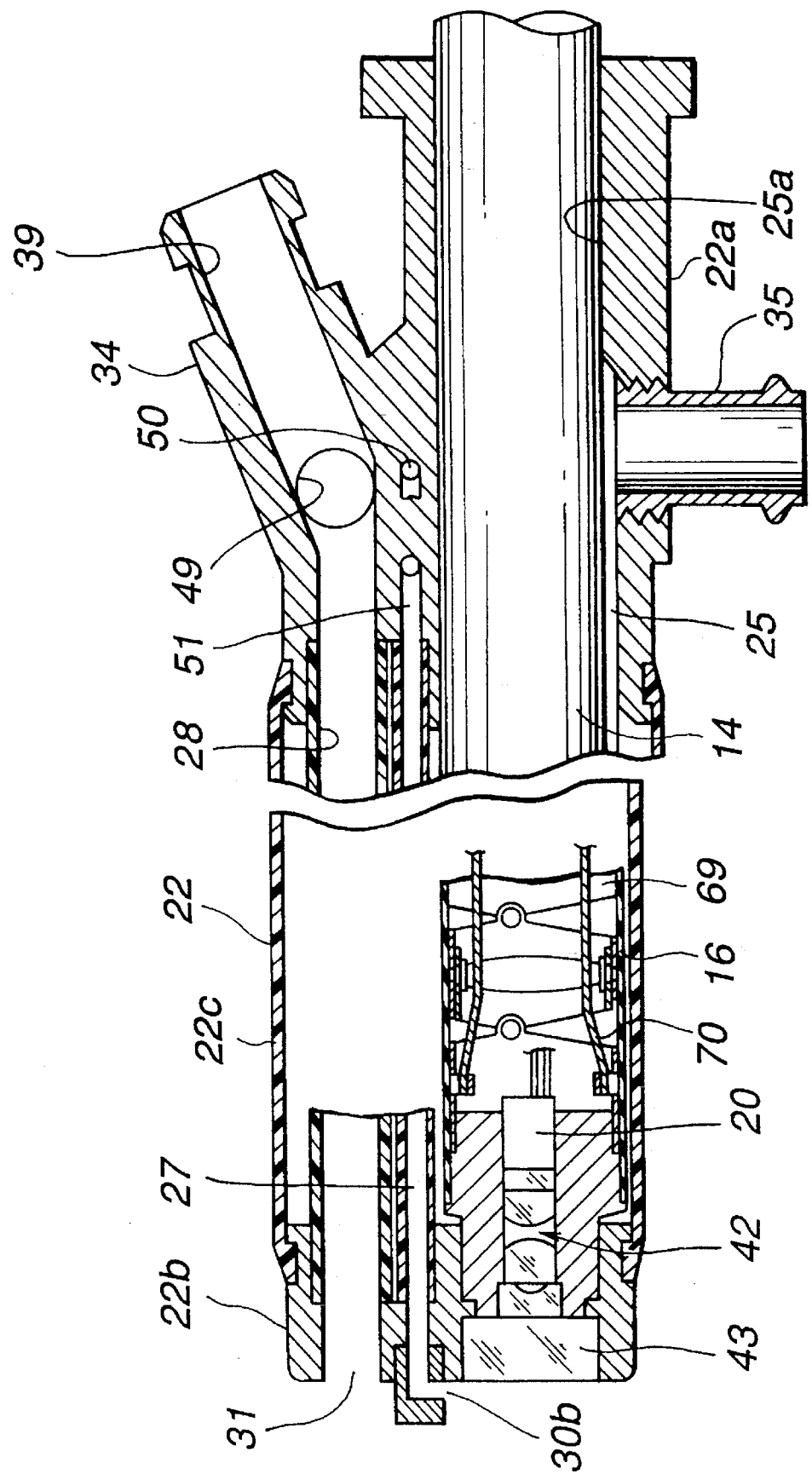
Figure 41:
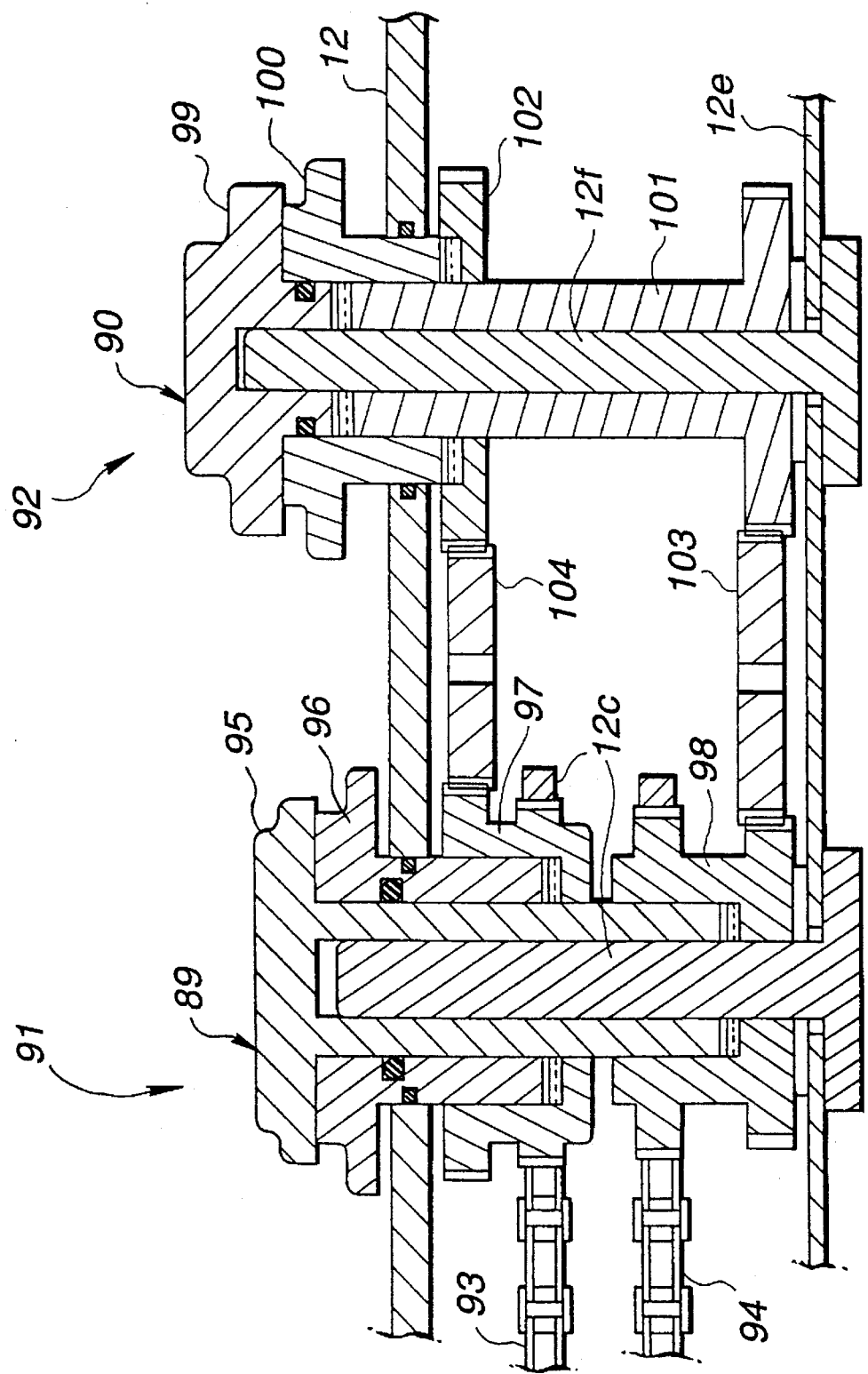

FIGS. 37 to 41 relate to a ninth embodiment of the present invention. FIG. 37 is an overall schematic view which illustrates an endoscope apparatus to which a cover-type endoscope is connected. FIG. 38 is a schematic view which illustrates the cover-type endoscope. FIG. 39 illustrates installation of an angle knob. FIG. 40 is a side elevational cross sectional view which illustrates the leading portion of the cover-system endoscope. FIG. 41 is a cross sectional view which illustrates the structure of a warp control mechanism.

An endoscope apparatus 86 shown in FIG. 37 is an apparatus to which an endoscope-cover-system endoscope (hereinafter abbreviated a "cover-system endoscope") 87 having channels can be attachably/detachably connected.

The cover-system endoscope 87 is constituted by combining an insert cover portion 22 and an endoscope-cover-type endoscope (hereinafter abbreviated to a "cover-type endoscope") 88 having channels. The cover-type endoscope 88 is an electronic-type endoscope.

The insert cover portion 22 covers an insert 14 of the cover-type endoscope 88 shown in FIG. 38 to eliminate the necessity of cleaning and disinfecting the endoscope to be performed after an inspection has been completed. The cover-type endoscope 88 is used in a state where the foregoing insert cover portion 22 is inserted into the insert and the cover-type endoscope 88 is covered hermetically against water.

The endoscope apparatus 86 comprises the cover-system endoscope 87, a cart 5 accommodating various peripheral devices to which the cover-system endoscope 87 is connected, and a cover holder 6 for holding the cover-system endoscope 87.

The cart 5 shown in FIG. 37 and accommodating the peripheral devices accommodates, for example, a light source apparatus 7, a video processor 8, a fluid control apparatus 9, and an expander (hereinafter abbreviated to an "expander") 10 for an endoscope cover having channels. The cart 5 holds a monitor 11 placed on the ceiling plate thereof.

The light source apparatus 7 supplies irradiation light to the cover-type endoscope 88 of the cover-system endoscope 87. The video processor 8 is connected to the electronic-type cover-type endoscope 88 to convert an electric signal supplied from the endoscope 88 into a standard video signal, followed by outputting the video signal to the monitor 11. The monitor 11 receives the video signal to display an image of the endoscope 4.

The fluid control apparatus 9 supplies air/water through tubular passages formed in the insert cover portion 22 and serving as channels to be described later. Therefore, the fluid control apparatus 9 has a water-supply source and an air-supply source (omitted from illustration). The tubular passages connected to the air-supply source and the water-supply source are controlled by electromagnetic valves to be opened/closed as desired.

The expander 10 supplies air into the insert cover portion 22 to expand it. As a result of the expansion, the cover-type endoscope 88 can easily be fastened to or removed from the insert cover portion 22.

As shown in FIG. 38, the cover-type endoscope 88 comprises a control unit 12, a universal cord 13 extending from the side portion of the control unit 12, and an insert 14 connected to the control unit 12. The insert 14 of the cover-type endoscope 88, as shown in FIG. 38, comprises a flexible tube portion 15, a warp-enabled portion 16 that can be warped, and a hard leading portion 17 when viewed from the base portion of the control unit 12 toward the leading portion.

The insert 14 of the cover-type endoscope 88 has a small diameter and has a D-shape cross sectional shape. The leading portion 17 of the cover-type endoscope 88 has irradiation optical system (omitted from illustration) and an objective optical system 42 shown in FIG. 40. It should be noted that the insert 14 of the endoscope 88 may be formed into a cylindrical shape.

At the rear ends of the irradiation optical system, light emission ends of light guide fibers (omitted from illustration) are disposed. The light guide fibers are allowed to pass through the insert 14, the control unit 12 and the universal cord 13.

The universal cord 13 has, at an end portion thereof, a connector 19. The connector 19 is attachably/detachably connected to a connector receptor 7a provided for the light source apparatus 7. As a result, irradiation light can be supplied from the light source apparatus 7 to the incidental ends of the light guide fibers.

As shown in FIG. 40, a solid-state image sensing device 20 for converting an incident optical image into an electric signal is disposed at the rear end of the objective optical system 42. The electric signal transmitted from the solid-state image sensing device 20 is received by the video processor 8 via a signal cord 21 extending from the side portion of the connector 19 shown in FIG. 37 and so forth.

The warp-enabled portion 16 of the cover-type endoscope 88 includes a plurality of warping blocks 69 combined rotatively. End portions of a pair of warp controlling wires 70 are secured to the leading block among the warping blocks 69, while the other end portions of the same are, in the portion adjacent to the control unit 12, fixed to a chain to be described later. Also another pair of warp controlling wires (omitted from illustration) penetrate the warping blocks 69 to be fixed there while being deviated from each other at an angle of 90° in the circumferential direction. Thus, the warp-enabled portion 16 can be warped in the vertical direction and the lateral direction.

As shown in FIG. 38, the control unit 12 has a holding portion 12a at the base portion thereof. Furthermore, a control unit body 12b is connected to the upper portion of the holding portion 12a. The control unit body 12b of the control unit 12 has an air-supply/water-supply control switch 46, a suction control switch 47, and a function switch 48 for taking a photograph each disposed therein.

The control unit body 12b has, on the side surface thereof, an angle knob 89 for the left hand that is attachably/detachably fastened to a knob shaft 12c projecting over the body 12b as shown in FIG. 39.

The holding portion 12a has, on the side surface thereof, an angle knob 90 for the right hand that is attachably/detachably fastened to an angle shaft to be described later. In particular, the angle knob 90 for the right hand is made of material, such as polysulfon or denatured PPO, that can be disinfected.

The cover holder 6 shown in FIG. 37 has an arm portion 6a that holds the insert cover portion 22 at the time of fastening the insert cover portion 22 to the cover-type endoscope 88. As a result, the endoscope 88 can sanitarily be held because the hand does not touch the insert cover portion 22. Furthermore, the operation can easily be performed.

FIG. 40 is a side elevational cross sectional view which illustrates a state where the cover-type endoscope 88 is inserted into the insert cover portion 22.

The insert cover portion 22 is used to isolate the insert 14 of the cover-type endoscope 88 from the external environment. The insert cover portion 22 is formed into an elongated shape, the insert cover portion 22 having a joint (hereinafter abbreviated to a "joint") 22a for fixing the control unit 12 of the endoscope 88, that is a unit adjacent to the operator, and a leading unit portion 22b that are made of hard material, for example, metal or resin.

The portion between the joint 22a of the insert cover portion 22 and the leading unit portion 22b is hermetically covered with an insert-cover coat 22c made of flexible material. The insert cover coat 22c is, at the leading portion thereof, connected to be received by an edge portion formed around the outer surface of the rear portion of the leading unit portion 22b. The insert cover coat 22c is similarly connected in a portion adjacent to the joint 22a.

The insert-cover coat 22c is made of resin, such as polyurethane, that exhibits excellent chemical resistance and that is relatively flexible.

The insert cover portion 22 includes an endoscope insertion channel 25 into which the insert 14 can be inserted, and an air-supply tubular passage 26, a water-supply tubular passage 27 and a suction tubular passage 28 serving as channels.

The endoscope insertion channel 25 has, in the base portion thereof, an opening 25a for inserting the insert 14 in the joint 22a. The opening 25a of the endoscope insertion channel 25 is arranged to receive the end portion of the insert 14 adjacent to the operator. It should be noted that the opening 25a may be arranged to receive the base portion of the endoscope control unit 12. The endoscope insertion channel 25 is closed in the leading unit portion 22b so that the insert 14 of the cover-type endoscope 88 can be hermetically isolated from the outer environment.

The air-supply tubular passage 26, the water-supply tubular passage 27 and the suction tubular passage 28 extend outwardly from the side portion of the joint 22a, while their end portions are respectively closed.

The air-supply tubular passage 26, the water-supply tubular passage 27 and the suction tubular passage 28 have their intermediate portions respectively formed into a suction connection tube 49, an air-supply connection tube 50 and a water-supply connection tube 51. The suction connection tube 49, the air-supply connection tube 50 and the water-supply connection tube 51 are communicated with a tubular passage integrating connector 52 fastened to the side portion of the joint 22a shown in FIG. 37. The suction, air-supply and water-supply connection tubes 49, 50 and 51 respectively are communicated with a suction external tube 57, an air-supply external tube 55 and a water-supply external tube 56 via the tubular passage integrating connector 52. The external tubes 55, 56 and 57 are connected to the air supply source, the water supply source and the suction source and the like.

A curing tool insertion port 34 and an expansion tube joint 35 project over the side portion of the joint 22a as shown in FIG. 40. The expansion tube joint 35 includes the internal tubular passage that is connected to the endoscope insertion channel 25. An expansion tube 36 connected to the expander 10 is attachably/detachably connected to the expansion tube joint 35.

The curing tool insertion port 34 projects diagonally rearwards with respect to a direction of the longitudinal axis of the insert cover portion 22. The internal tubular passage of the curing tool insert port 34 is opened at the end portion thereof, while another end portion is connected to the suction tubular passage 28. That is, the suction tubular passage 28 also serves as a tubular passage for the curing tool channel at the leading portion thereof. Therefore, the opening 31 is an outlet port for the curing tool. Reference numeral 39 represents a tubular passage of the rear portion of the curing channel.

The structure of the warp control mechanism will now be described.

FIG. 41 illustrates the control unit including the angle knob 89 for the left hand, the angle knob 90 for the right hand and their peripheral portions.

The warp control mechanism according to this embodiment comprises a warp control mechanism 91 for the left hand and a warp control mechanism 92 for the right hand as shown in FIG. 41.

The warp control mechanism 91 for the left hand and the warp control mechanism 92 for the right hand respectively include the angle knob 89 for the left hand and the angle knob 90 for the right hand. As a result, the warp-enabled portion 16 is warped upwards (hereinafter called "U"), downwards (hereinafter called "D")/rightwards (hereinafter called "R") and leftwards (hereinafter called "L").

The warp control mechanism 91 for the left hand and the warp control mechanism 92 for the right hand are operated synchronously via two gears to be described later. Furthermore, the warping blocks 69 are rotated vertically or laterally when a UD chain 93 or a RL chain 94 is moved forwards/rearwards. The end portions of the warp control wires 70 are connected to the two end portions of the UD chain 93 to warp the warp-enabled portion 16 in the UD direction.

The end portions of the warp control wires (omitted from illustration) are connected to the two end portions of the RL chain 94 to warp the warp-enabled portion 16 in the RL direction.

The knob shaft 12c for the left hand and the knob shaft 12f for the right hand are, while keeping a distance, fastened to an internal plate 12e disposed in the control unit 12. The head portions of the knob shaft 12c for the left hand and the knob shaft 12f for the right hand respectively project over the outer wall of the control unit 12. Furthermore, holes are formed around the knob shaft 12c for the left hand and the knob shaft 12f for the right hand, the holes being formed in the outer wall of the control unit 12 to allow the angle knobs 89 and 90 to pass through.

The angle knob 89 for the left hand has a RL knob 95 for the left hand and having a projecting fastening portion to be fastened to the knob shaft 12c for the left hand and a UD knob 96 for the left hand to be fastened around the fastening portion of the RL knob 95 for the left hand.

The RL knob 95 for the left hand and the UD knob 96 for the left hand respectively are engaged to a RL gear 98 for the left hand and a UD gear 97 for the left hand by gears. Furthermore, the RL gear 98 for the left hand and the UD gear for the left hand respectively are fastened to the RL chain 94 and the UD chain 93 attachably/detachably and rotatively.

Therefore, when the RL knob 95 for the left hand is rotated, the RL chain 94 is rotated. When the UD knob 96 for the left hand is rotated, the UD chain 93 is rotated.

Also the warp control mechanism 92 for the right hand is structured substantially similarly to the mechanism 91 for the left hand. The angle knob 90 for the right hand has a RL knob 99 for the right hand and having a projecting fastening portion to be fastened to the knob shaft 12f for the right hand and a UD knob 100 for the right hand to be fastened around the fastening portion of the RL knob 99 for the right hand.

The RL knob 99 for the right hand and the UD knob 100 for the right hand are respectively engaged to the RL gear 101 for the right hand and the UD gear 102 for the right hand by the gears.

The RL gear 98 for the left hand and the RL gear 101 for the right hand respectively are engaged to the RL gear 103 to be synchronously rotated.

The UD gear 97 for the left hand and the UD gear 102 for the right hand respectively are engaged to the UD gear 104 to be synchronously rotated.

In synchronization with the rotations of the RL knob 99 for the right hand and the UD knob 121 for the right hand, the RL chain 94 and the UD chain 93 are therefore rotated, respectively.

As a result of the foregoing arrangement of the structure, the left hand is used to hold the control unit 12, that is the unclean area. The left hand that can be contaminated is used to rotate the RL knob 95 for the left hand and the UD knob 96 for the left hand.

The RL knob 95 for the left hand transmits the rotational force to the RL gear 98 for the left hand, resulting in the RL chain 94 is pushed/pulled. The wire (omitted from illustration) is pulled by the RL chain 94, the traction causing the warping blocks 69 connected to the other end portions of the wire to be warped rightwards/leftwards. That is, the warp-enabled portion 16 is warped laterally.

When the UD knob 96 for the left hand is rotated, the rotation force is transmitted to the UD gear 97 for the left hand, the UD chain 93 and the wires 70. In accordance with the direction of the rotation operation, the warp-enabled portion 16 is vertically warped.

Since the right hand holds the insert cover portion 22 and the like that are the clean areas, the angle knob 90 for the right hand is used when the clean hand is used to perform the warping operation. When the RL knob 99 for the right hand is rotated by the right hand, the RL gear 101 for the right hand is rotated, causing the RL gear 103 to be rotated in a direction opposing the direction of the rotation of the RL gear 101 for the right hand. Furthermore, the RL gear 98 for the left hand is rotated in the same direction of the rotation of the RL gear 101 for the right hand. The foregoing rotations cause the RL chain 94 to be pulled, resulting in the warp-enabled portion 16 to be warped laterally.

Similarly, the clean right hand rotates the UD knob 100 for the right hand, the rotational force being transmitted to the UD gear 102 for the right hand, the UD gear 104 and the UD gear 97 for the left hand in this sequential order. As a result, the warp-enabled portion 16 is warped vertically.

In the case where, for example, the UD knob 96 for the left hand of the foregoing structure is rotated to downwards warp the warp-enabled portion 16, the rightward rotation of the UD knob 100 for the right hand causes the warp-enabled portion 16 to be warped downwards similarly.

Similarly, the rotation of the RL knob 95 for the left hand in the same direction of the rotation of the RL knob 99 for the right hand causes the warp-enabled portion 16 to perform the similar operation.

That is, the lateral/vertical warping operation is performed in such a manner that the warp-enabled portion 16 is warped in the same warping direction if the angle knob 89 for the left hand and the angle knob 90B for the right hand are rotated in the same direction.

The angle knob 90B for the right hand may be used repeatedly or made be made disposable. If the angle knob 90B for the right hand is made disposable, it must be made a medical waste.

According to this embodiment, the unclean left hand does not hold the angle knob 90 for the right hand, and the right and the left knobs can be individually operated as desired to cause a similar warping operation to be performed. As a result, the clean right hand can be protected from contamination occurring via the foregoing knob.

According to this embodiment, the necessity of operating the angle knob by only the hand that holds the control unit. Therefore, the warping operation can be performed without a necessity of great skill.

According to this embodiment, the angle knob 90 for the right hand and the angle knob 89 for the left hand are arranged to be operated in the same direction and causing the same warping direction to be realized. Therefore, the operator is able to operate them without inconvenience regardless of the hand that holds the foregoing knobs.

Figure 42:
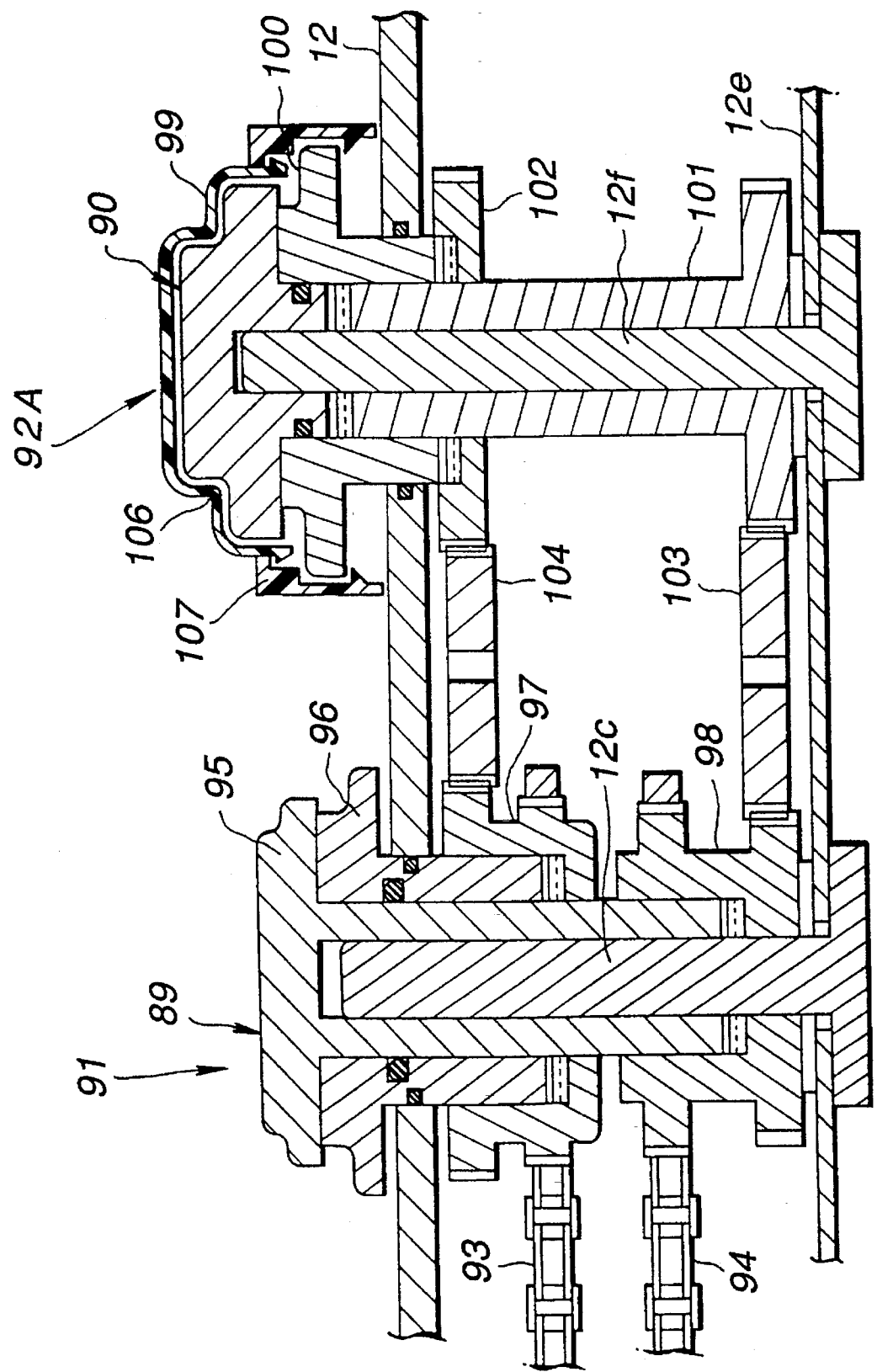
FIG. 42 is a cross sectional view which illustrates the structure of a warp control mechanism according to a tenth embodiment of the present invention.

FIG. 42 is a cross sectional view which illustrates the structure of a warp control mechanism according to a tenth embodiment of the present invention.

The warp control mechanism shown in FIG. 42 has an arrangement that a cover for the angle knob is provided in addition to the mechanism according to the ninth embodiment. The same structures and the operations similar to those of the ninth embodiment are given the same reference numerals, and their descriptions and drawings are omitted here. Then, only different structures will now be described.

This embodiment has an arrangement that the cover for the angle knob is provided for a warp control mechanism 90A for the right hand, the cover comprising a RL knob cover 106 and a UD knob cover 107.

The RL knob cover 106 covers the front surface and the side outer surface of the RL knob 99 for the right hand. The UD knob cover 107 covers the portion from the side outer surface of the UD knob 100 for the right hand to a position adjacent to the outer wall of the control unit 12.

The RL knob cover 106 is rotatively fastened to the UD knob cover 107. The UD knob cover 107 is attachably/detachably fastened to the UD knob 100 for the right hand by, for example, snap fit.

The foregoing RL knob cover 106 and the UD knob cover 107 are made to be disposable products.

When the right hand is used to realize lateral warping with the foregoing structure, the RL knob 99 for the right hand is operated via the UD knob cover 107.

After the operation has been completed, the UD knob cover 107 is removed from the UD knob 100 for the right hand. As a result, also the RL knob cover 106 can be removed.

According to this embodiment, the clean right hand is not contaminated, resulting in prevention of invasion of a germ into the body of a patient.

Although each of the foregoing embodiment is described so that the insert is operated by the right hand and the control unit is operated by the left hand in accordance with the ordinary manner, the present invention is not limited to this. The structure may be similarly arranged if the insert is handled by the left hand and the control unit is held by the right hand.

The cover-type endoscope according to the present invention is not limited to the foregoing electronic type endoscope. It may be an optical-type endoscope or an ultrasonic-type endoscope or the like without any particular limitation. The cover to be fastened to the cover-type endoscope according to the present invention is not limited to the cover having channels. A channel-less cover may be employed.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

What claimed is:

1. An endoscope apparatus comprising:

an endoscope-cover-type endoscope having a universal cord;

peripheral devices connected to said endoscope-cover-type endoscope via a connector disposed at an end portion of said universal cord nearest said peripheral devices;

an endoscope cover formed into a cylindrical shape and made to be contractive to cover said universal cord; and a cover accommodating case in which cord cover portions for a plurality of operations are accommodated while being contracted in such a manner that said cord cover portions can be ejected as desired, wherein said cover accommodating case is disposed adjacent a position at which said peripheral devices and said universal cord are connected.

2. An endoscope apparatus comprising:

an endoscope-cover-type endoscope having a universal cord;

peripheral devices connected to said endoscope-cover-type endoscope via a connector disposed at an end portion of said universal cord nearest said peripheral devices;

an endoscope cover formed into a cylindrical shape and made to be contractive to cover said universal cord; and a cover accommodating case in which cord cover portions for a plurality of operations are accommodated while being contracted in such a manner that said cord cover portions can be ejected as desired, wherein said cover accommodating case is made attachable/detachable to and from said peripheral devices.

3. An endoscope apparatus comprising:

an endoscope-cover-type endoscope having a universal cord;

peripheral devices connected to said endoscope-cover-type endoscope via a connector disposed at an end portion of said universal cord nearest said peripheral devices;

an endoscope cover formed into a cylindrical shape and made to be contractive to cover said universal cord; and a cover accommodating case in which cord cover portions for a plurality of operations are accommodated while being contracted in such a manner that said cord cover portions can be ejected as desired, wherein said cover accommodating case is disposed in a connector connection portion of a light source apparatus for supplying irradiation light to said endoscope-cover-type endoscope.

4. An endoscope apparatus comprising:

an endoscope-cover-type endoscope having a universal cord;

peripheral devices connected to said endoscope-cover-type endoscope via a connector disposed at an end portion of said universal cord nearest said peripheral devices;

an endoscope cover formed into a cylindrical shape and made to be contractive to cover said universal cord; and a cover accommodating case in which cord cover portions for a plurality of operations are accommodated while being contracted in such a manner that said cord cover portions can be ejected as desired, wherein said cord cover portion is formed to be easily separated from said universal cord, and a plurality of said cord covers are accommodated in said cover accommodating case while being contracted.

5. An endoscope apparatus comprising:

an endoscope-cover-type endoscope from which a universal cord extends;

peripheral devices connected to said endoscope-cover-type endoscope via a connector disposed at an end portion of said universal cord nearest said peripheral devices; and an endoscope cover having an insert cover portion for covering an insert portion of said endoscope-cover-type endoscope, and a cord cover portion formed into a cylindrical bellows shape and made to be contractive to cover said universal cord, wherein said cord cover portion includes a joint portion at one end which is made attachable/detachable to and from said connector and the body of said endoscope-cover-type endoscope.

* * * * *